US008507531B2

(12) United States Patent
Magda et al.

(10) Patent No.: US 8,507,531 B2
(45) Date of Patent: Aug. 13, 2013

(54) WATER-SOLUBLE ZINC IONOPHORES, ZINC CHELATORS, AND/OR ZINC COMPLEXES AND USE FOR TREATING CANCER

(75) Inventors: Darren Magda, Cupertino, CA (US); Jonathan L. Sessler, Austin, TX (US)

(73) Assignee: Jonathan L. Sessler, Austin, TX (US)

( * ) Notice: Subject to any disclaimer, the term of this patent is extended or adjusted under 35 U.S.C. 154(b) by 483 days.

(21) Appl. No.: 12/905,823

(22) Filed: Oct. 15, 2010

(65) Prior Publication Data

US 2011/0034431 A1 Feb. 10, 2011

Related U.S. Application Data

(60) Continuation of application No. 12/410,392, filed on Mar. 24, 2009, now Pat. No. 7,838,536, which is a division of application No. 11/688,789, filed on Mar. 20, 2007, now Pat. No. 7,528,125.

(60) Provisional application No. 60/743,588, filed on Mar. 20, 2006.

(51) Int. Cl.
*A61K 31/444* (2006.01)
*C07D 401/12* (2006.01)

(52) U.S. Cl.
USPC .................. 514/334; 546/257; 546/261

(58) Field of Classification Search
USPC .................. 514/334; 546/257, 261
See application file for complete search history.

(56) References Cited

U.S. PATENT DOCUMENTS

| 2,786,847 | A | 3/1957 | Cislak |
| 2,809,971 | A | 10/1957 | Bernstein et al. |
| 3,236,733 | A | 2/1966 | Karsten et al. |
| 3,589,999 | A | 6/1971 | McRae et al. |
| 3,590,035 | A | 6/1971 | Danico |
| 3,753,196 | A | 8/1973 | Kurtz et al. |
| 3,761,418 | A | 9/1973 | Parran et al. |
| 3,773,770 | A | 11/1973 | Danico |
| 3,862,305 | A | 1/1975 | Bouillon et al. |
| 4,345,080 | A | 8/1982 | Bolich, Jr. |
| 4,379,753 | A | 4/1983 | Bolich, Jr. |
| 4,470,982 | A | 9/1984 | Winkler |
| 5,252,720 | A | 10/1993 | Sessler et al. |
| 6,825,186 | B1 | 11/2004 | Sessler et al. |
| 7,528,125 | B2 | 5/2009 | Magda et al. |
| 2001/0002251 | A1 | 5/2001 | Woodburn et al. |

OTHER PUBLICATIONS

Harris, J.M. and Chess, R.B., "Effect of Pegylation on Pharmaceuticals," Nature Reviews. Drug Discovery 2:214-221 (2003).
PCT/US07/06960 Search Report dated Jan. 23, 2008.

*Primary Examiner* — Charanjit Aulakh
(74) *Attorney, Agent, or Firm* — Wilson, Sonsini, Goodrich & Rosati

(57) ABSTRACT

Disclosed herein are novel zinc ionophores, zinc chelators and/or zinc complexes with enhanced aqueous solubility. Methods of treating cancer using at least one zinc ionophore and/or zinc chelator are also disclosed. Also disclosed herein are compositions and methods for treating cancer with combination therapy using at least one texaphyrin metal complex and at least one zinc ionophore or the respective pharmaceutically acceptable derivatives or salts thereof.

22 Claims, 51 Drawing Sheets

DPM3

DPM1

WATER-SOLUBLE ZINC IONOPHORES, ZINC CHELATORS, AND/OR ZINC COMPLEXES AND USE FOR TREATING CANCER

RELATED APPLICATIONS

This application is a continuation of U.S. Ser. No. 12/410,392, filed Mar. 24, 2009 and issued as U.S. Pat. No. 7,838,536, which is a divisional application of U.S. Ser. No. 11/688,789, filed Mar. 20, 2007 which issued as U.S. Pat. No. 7,528,125, which claims the benefit of U.S. Provisional Application No. 60/743,588, filed Mar. 20, 2006, each of which are herein incorporated by reference in their entirety.

FIELD OF THE INVENTION

Described herein are compounds, methods of making such compounds, pharmaceutical compositions and medicaments containing such compounds, and methods of using such compounds and compositions that are zinc ionophores, zinc chelators and/or zinc complexes with enhanced aqueous solubility.

BACKGROUND OF THE INVENTION

The importance of zinc in living systems has long been recognized. Zinc ions serve multiple biological functions that may be classified as catalytic, structural, or regulatory. The catalytic activity of zinc is due to its Lewis acidity, which serves to activate reactants as in well-described enzymatic mechanisms such as that of carboxypeptidase. Zinc plays a structural role in supporting higher order protein structure by coordinate interactions with cysteine or histidine residues, and examples such as those found in "zinc finger" type transcription factors are also well-known. However, the regulatory function of zinc, which relates to the effect of "free" zinc (defined here as loosely- and non-protein bound zinc) on processes such as cellular metabolism and transcription, remains a complex subject of considerable recent interest and discovery. For example, under oxidative stress conditions, cellular zinc release results in a multitude of pathologies on the organismal level.

Zinc ionophores are capable of transporting zinc ions (hereinafter, simply referred to as zinc) between the extracellular environment and the intracellular environment. One example of a zinc ionophore is ZnHPT, 1-hydroxypyridine-2-thione, also known as pyrithione. ZnHPT has poor aqueous solubility.

SUMMARY OF THE INVENTION

Described herein are zinc ionophores, zinc chelators and/or zinc complexes with enhanced aqueous solubility. Zinc ionophores, zinc chelators and/or zinc complexes with enhanced aqueous solubility have increased bioavailability upon administration as compared to zinc ionophores, zinc chelators and/or zinc complexes with poor aqueous solubility. Also described herein are methods for synthesizing zinc ionophores, zinc chelators and/or zinc complexes. Described herein are also methods of treating cancer using at least one zinc ionophore, zinc chelator and/or zinc complex. In an aspect described herein, zinc ionophores can be used to treat cancer by delivering zinc to cancer cells. In another aspect described herein, zinc chelators can be used to treat cancer due to zinc chelation within the cancer cells by the unbound ligand. Also described herein are compositions and methods for treating cancer with combination of an expanded porphyrin metal complex and at least one zinc ionophore, zinc chelator and/or zinc complex or their respective pharmaceutically acceptable derivatives. In certain embodiments, the expanded porphyrin metal complex is a texaphyrin metal complex. In certain embodiments, the texaphyrin metal complex is a texaphyrin gadolinium complex. In certain embodiments, the texaphyrin is motexafin gadolinium (MGd).

One aspect described herein relates to zinc ionophores or zinc complexes, comprising Formula (I):

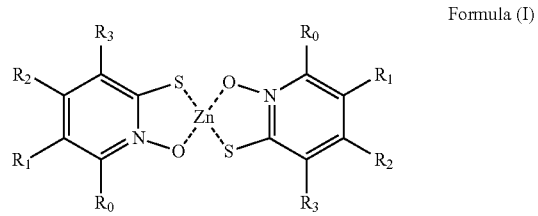

Formula (I)

wherein:

each $R_0$, each $R_1$, each $R_2$, and each $R_3$ on each side of Formula (I) is independently H, OH, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-; provided that at least one of the $R_0$, $R_1$, $R_2$, or $R_3$ groups is $L_1X_nL_2$-;

each $L_1$ is independently H, OH, $NH_2$, halogen, —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20;

each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R)—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

optionally, at least one of $R_0$, $R_1$, $R_2$, or $R_3$ on one side of Formula (I) may be attached by L or -$L_1X_nL_2$- to at least one of $R_0$, $R_1$, $R_2$, or $R_3$ on the other side of Formula (I);

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')-, —CON(R')-(alkylene or substituted alkylene)-, -(alkylene or substituted alkylene)-CON(R)-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

In one embodiment is a compound of Formula (I) wherein each of $R_0$, $R_1$, $R_2$, and $R_3$ is independently H, alkyl, (CH$_2$)$_v$—OR$_y$, OR$_y$, NHR$_y$, C(O)NHR$_y$, wherein R$_y$ is PEG or PPG; wherein PEG or PPG is —(O-alkylene or O-substituted alkylene)$_x$-O—R$_z$ or -(alkylene-O or substituted alkylene-O)$_x$—R$_z$; wherein R$_z$ is H or alkyl; v and x are independently 1, 2, 3, 4, 5, 6, 7, 8, 9, 10, 11, 12, 13, 14, 15, 16, 17, 18, 19, or 20; and pharmaceutically acceptable salts, pharmaceutically acceptable atropisomers, pharmaceutically active metabolites, pharmaceutically acceptable prodrugs, and pharmaceutically acceptable solvates.

In one embodiment is a compound of Formula (I) wherein each $R_0$, $R_1$, $R_2$, and $R_3$ are the same on each side of Formula (I).

In another embodiment is a compound of Formula (I) wherein $R_3$ is OPEG; wherein x is 3; and $R_0$, $R_1$, and $R_2$ are H.

In a further embodiment is a compound of Formula (I) wherein $R_1$ is C(O)NHPEG; wherein x is 3; and $R_0$, $R_2$, and $R_3$ are H.

In yet a further embodiment is a compound of Formula (I) wherein $R_1$ is CH$_2$—OPEG; wherein x is 3; and $R_0$, $R_2$, and $R_3$ are H. In another embodiment is a compound of Formula (I) wherein $R_1$ is CH$_2$—OPEG; wherein x is 2; and $R_0$, $R_2$, and $R_3$ are H.

In one embodiment is a compound of Formula (I) wherein $R_1$ is CH$_2$—OPEG; wherein x is 1; and $R_0$, $R_2$, and $R_3$ are H. In another embodiment is a compound of Formula (I) wherein $R_0$ is CH$_3$ and $R_3$ is OPEG; wherein x is 1; and $R_1$ and $R_2$ are H. In a further embodiment is a compound of Formula (I) wherein $R_0$ is CH$_3$ and $R_3$ is OPEG; wherein x is 2; and $R_1$ and $R_2$ are H. In yet a further embodiment is a compound of Formula (I) wherein $R_0$ is CH$_3$ and $R_3$ is OPEG; wherein x is 3; and $R_1$ and $R_2$ are H.

In one aspect is a compound, comprising Formula (Ib):

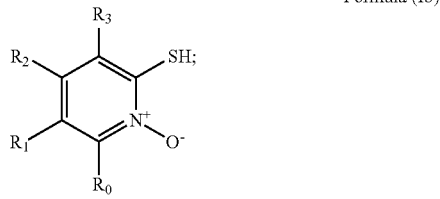

Formula (Ib)

wherein:

each $R_0$, each $R_1$, each $R_2$, and each $R_3$ is independently H, OH, NH$_2$, NO$_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-; provided that at least one of the $R_0$, $R_1$, $R_2$, or $R_3$ groups is $L_1X_nL_2$-;

each $L_1$ is independently H, OH, NH$_2$, halogen, —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20; and each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

In one aspect is a compound comprising Formula (II):

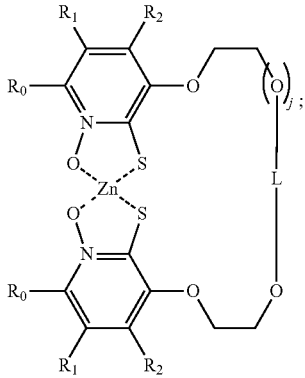

Formula (II)

wherein:
each $R_0$, each $R_1$, and each $R_2$, on each side of Formula (II) is independently H, OH, NH$_2$, NO$_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-;

each $L_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20;
j is 0 or 1;

each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and L is selected from the group consisting of a bond, alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)$_m$-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R') C(O)N(R')—, —N(R')C(O)N(R')-(alkylene or substituted alkylene)-, -(alkylene or substituted alkylene)-N(R')C(0)N(R)-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; m is an integral number selected from 1 to 20; and pharmaceutically acceptable salts, pharmaceutically acceptable atropisomers, pharmaceutically active metabolites, pharmaceutically acceptable prodrugs, and pharmaceutically acceptable solvates.

In one embodiment is a compound of Formula (II) wherein j is 0; L is a bond; and $R_0$, $R_1$, and $R_2$ are H. In another embodiment is a compound of Formula (II) wherein L is (CH$_2$OCH$_2$)$_m$, wherein m is an integral number from 0-4; j is 1, and $R_0$, $R_1$, and $R_2$ are H.

In one embodiment is a pharmaceutical composition comprising a compound of Formula (I) and a pharmaceutically acceptable excipient. In another embodiment is a pharmaceutical composition comprising a compound of Formula (II) and a pharmaceutically acceptable excipient.

In one aspect is a method of treating cancer comprising administering to a patient in need a therapeutically effective amount of at least one compound having the structure of Formula (I):

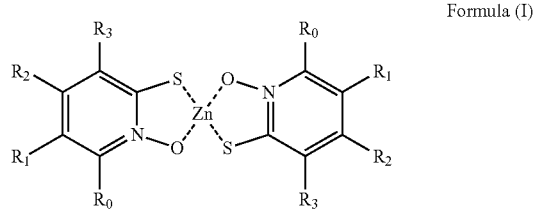

Formula (I)

wherein:

each $R_0$, each $R_1$, each $R_2$, and each $R_3$ on each side of Formula (I) is independently OH, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-; provided that at least one of the $R_0$, $R_1$, $R_2$, or $R_3$ groups is $L_1X_nL_2$—;

each $L_1$ is independently H, OH, $NH_2$, halogen, —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20;

each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

optionally, at least one of $R_0$, $R_1$, $R_2$, or $R_3$ on one side of Formula (I) may be attached by L or -$L_1X_nL_2$- to at least one of $R_0$, $R_1$, $R_2$, or $R_3$ on the other side of Formula (I);

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R)-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R)-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R') C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

In one embodiment is a method of treating cancer further comprising the step of administering to a patient in need a therapeutically effective amount of motexafin gadolinium or a pharmaceutically acceptable texaphrin derivative. In one embodiment is a method of treating cancer comprising administering to a patient in need a compound of Formula (I) wherein the cancer is selected from the group consisting of adrenal cortical cancer, anal cancer, aplastic anemia, bile duct cancer, bladder cancer, bone cancer, bone metastasis, adult CNS brain tumors, pediatric CNS brain metastases, brain metastases, breast cancer, Castleman Disease, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, hematological malignancies, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sarcoma, vaginal cancer, vulvar cancer, and Waldenstrom's macroglobulinemia. In one embodiment, the cancers are selected from the group consisting of metastatic brain cancer, lung cancer, glioblastoma, lymphomas, leukemia, renal cell cancer (kidney cancer), head and neck cancer, breast cancer, prostrate cancer, and ovarian cancer.

Another aspect described herein are pharmaceutical compositions comprising at least one zinc ionophore and/or zinc complex having a structure selected from Formula (I), Formula (II), or Formula (III); and a pharmaceutically acceptable excipient. In one embodiment, the pharmaceutical composition is suitable for intravenous administration or administration by injection. In one embodiment, the pharmaceutical composition comprises water. In another embodiment the pharmaceutical composition comprises a cyclodextrin.

Another aspect described herein are zinc chelators having the structure of the group coordinating the zinc ion in structures of Formula (I), Formula (II), or Formula (III). Such zinc chelators include neutral structures or salt structures, wherein the counterion is any cation other than zinc. Thus, in any of the examples described herein (which describe the use of a zinc chelator) are included zinc chelators coordinated to a labile ion, such as sodium, potassium, or calcium, in which the labile ion can be replaced by zinc following adminstration of the non-zinc coordinated zinc chelator to the patient. Further, for zinc chelators or zinc ionophores capable of binding to multiple zinc ions are included mixed metal complexes in which the zinc chelator binds to different metal ions, or in the case of a zinc ionophore, binds to at least one zinc ion and one other metal ion.

Another aspect described herein are pharmaceutical compositions comprising at least one such zinc chelator; and a pharmaceutically acceptable excipient. In one embodiment, the pharmaceutical composition is suitable for intravenous administration or administration by injection. In one embodiment, the pharmaceutical composition comprises water.

Another aspect described herein relates to methods of enhancing solubility of an ionophore and/or chelator comprising the step of modifying at least one group of the ionophore and/or chelator with an optionally substituted PEG group or hydroxylated group. In some embodiments, the ionophore is a zinc ionophore. In some embodiments, the ionophore is an ionophore for a first row transition metal. In some embodiments, the ionophore for a first row transition metal is an ionophore for Mn(II), Mn(III), Fe(II), Fe(III), Co(II), Co(III), Cu(I), or Cu(II). In some embodiments, the zinc ionophore has a structure of Formula (I). In some embodiments the unmodified zinc ionophore is ZnHPT. In some embodiments, the modification with polyethylene glycol increases bioavailability of the zinc ionophore as compared to unmodified zinc ionophore.

Another aspect described herein relates to methods of enhancing the biological activity of an ionophore and/or chelator comprising the step of modifying at least one group of the ionophore and/or chelator with an electron-withdrawing or electron-donating (more likely) group. In some embodiments, the ionophore is a zinc ionophore. In some embodiments, the ionophore is an ionophore for a first row transition metal. In some embodiments, the ionophore for a first row transition metal is an ionophore for Mn(II), Mn(III), Fe(II), Fe(III), Co(II), Co(III), Cu(I), or Cu(II). In some embodiments, the zinc ionophore has a structure of Formula (I). In some embodiments, the unmodified zinc ionophore is ZnHPT.

An aspect also described herein relates to a method of treating cancer comprising the step of administering a therapeutically effective amount of at least one ionophore and/or chelator or their respective pharmaceutically acceptable derivatives, wherein the ionophore has at least one functional group selected from polyalkylene oxide, hydroxylated group, or a group having at least one amine, ammonium salt, carboxylate, sulfanyl, sulfinyl, sulfonyl, phosphate, phosphonate, phosphite; or combinations thereof. In some embodiments, the ionophore is an ionophore for a first row transition metal. In some embodiments, the ionophore for a first row transition metal is an ionophore for Mn(II), Mn(III), Fe(II), Fe(III), Co(II), Co(III), Cu(I), or Cu(II).

An aspect also described herein relates to a method of treating cancer comprising the step of administering a therapeutically effective amount of at least one zinc ionophore and/or zinc chelator or their respective pharmaceutically acceptable derivatives (including, for example chelate complexes of a zinc chelator, in which the zinc chelator coordinates a labile ion, e.g., sodium, potassium or calcium ions), wherein the zinc ionophore and/or zinc chelator has at least one functional group selected from polyalkylene oxide, hydroxylated group, or a group having at least one amine, ammonium salt, carboxylate, sulfanyl, sulfinyl, sulfonyl, phosphate, phosphonate, phosphite; or combinations thereof. In some embodiments, the zinc ionophore has the structure of any compound having the structure of Formula (I), Formula (II), Formula (III), or Formula (IV). In some embodiments, the zinc chelator has the structure of the group coordinating zinc in the structures of Formula (I), Formula (II), Formula (III), or Formula (IV). In some embodiments, the zinc ionophore has a mixed structure in which it is chelated by two different zinc chelators, at least one of which has the structure of the group coordinating zinc in the structures of Formula (I), Formula (II), Formula (III), or Formula (IV).

In some embodiments, the zinc ionophore and/or chelator has an aqueous solubility greater than about 1 millimolar, greater than about 2 millimolar, greater than about 3 millimolar, greater than about 4 millimolar, greater than about 5 millimolar or greater than about 6 millimolar. In some embodiments, the zinc ionophore and/or zinc chelator increases intracellular zinc concentration. In some embodiments, the zinc ionophore and/or zinc chelator chelates zinc within the cancer cells. In some embodiments, the zinc ionophore and/or zinc chelator functions to modulate zinc homeostasis in vivo. In some embodiments, the zinc ionophore and/or zinc chelator is modified with at least one polyethylene glycol group. In some embodiments, the zinc ionophore and/or zinc chelator is modified with at least one hydroxylated group. In some embodiments, the zinc ionophore is ZnHPT modified with at least one polyethylene glycol group. In some embodiments, the zinc ionophore is ZnHPT modified with at least one hydroxylated group. In some embodiments, the zinc ionophore and/or zinc chelator comprises a disulfide bond. In some embodiments, the disulfide bond is reduced within cancer cells.

Another aspect described herein relates to a method of treating cancer comprising administering to a patient in need thereof: (a) a therapeutically effective amount of motexafin gadolinium or a pharmaceutically acceptable texaphyrin derivative; and (b) a therapeutically effective amount of at least one zinc ionophore and/or zinc chelator or their respective pharmaceutically acceptable derivatives. In some embodiments, the motexafin gadolinium and the zinc ionophore and/or zinc chelator are sequentially administered to the patient. In some embodiments, the motexafin gadolinium and the zinc ionophore and/or zinc chelator are simultaneously administered to the patient. In some embodiments, the motexafin gadolinium and the zinc ionophore and/or zinc chelator are in a single formulation. In some embodiments, there is a synergistic combination between the motexafin gadolinium and the zinc ionophore and/or zinc chelator or their respective pharmaceutically acceptable derivatives. In some embodiments, the administration is performed using an intravenous injection or infusion.

Another aspect described herein relates to pharmaceutical compositions comprising (a) a therapeutically effective amount of motexafin gadolinium or a pharmaceutically acceptable texaphyrin derivative; and (b) a therapeutically effective amount of at least one zinc ionophore and/or zinc chelator or their respective pharmaceutically acceptable derivatives.

Another aspect described herein relates to an anticancer agent comprising an expanded porphyrin metal complex chemically linked via a linker group to a zinc ionophore and/or zinc chelator. In some embodiments, the zinc ionophore has the structure of the compounds of Formula (I), Formula (II), or Formula (III). In some embodiments, the zinc chelator has the structure of the group coordinating to the zinc ion in the compounds of Formula (I), Formula (II), or Formula (III). In some embodiments, the expanded porphyrin metal complex is a texaphyrin metal complex.

In another aspect, the zinc ionophore and/or zinc complex is a dipyrromethene (including derivatives thereof) bound to a zinc cation, or the zinc chelator is a dipyrromethene (includes derivatives thereof) that can bind a zinc cation. Further, any of the methods described herein, including methods for treating cancer can be used with such a zinc ionophore and/or zinc chelator.

INCORPORATION BY REFERENCE

Unless stated otherwise, all publications and patent applications mentioned in this specification are herein incorporated by reference to the same extent as if each individual publication or patent application was specifically and individually indicated to be incorporated by reference.

DETAILED DESCRIPTION OF THE INVENTION

Figure 1:
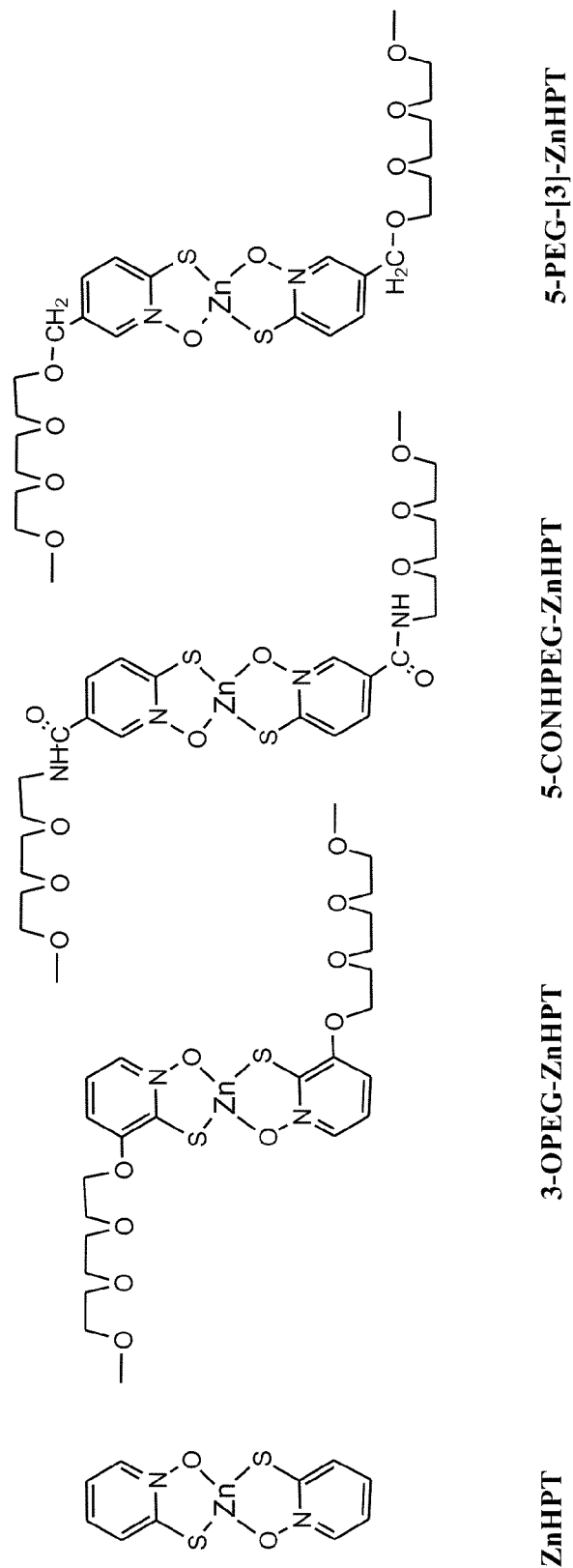
FIG. 1 presents non-limiting examples of zinc ionophores.

Zinc exists exclusively in the divalent state, and is therefore intrinsically redox-inactive. Zinc is nonetheless an active participant in redox chemistry as a consequence of its coordination environment: Wherever bound by two or more thiol ligands, the potential exists for ligand oxidation to form a disulfide with concomitant zinc release. Normally, the concentration of intracellular free zinc is maintained at a vanishingly low value. However, it is significantly increased by the release of zinc under conditions of oxidative stress. For example, increased free zinc has been measured in cells treated with hydrogen peroxide or nitric oxide. Thus, the level of intracellular free zinc is intimately connected to the redox state of the cell, although this level may be altered by other processes, including the exogenous administration of zinc.

This is particularly evident in neurological indications such as stroke, ALS, and AD. In animal models of stroke, for example, administration of zinc-binding chelators has been reported to reduce the degree of tissue damage surrounding induced ischemic lesions. In oncology, efforts are being made to correlate tumor metallothionein levels with clinical outcomes. This approach may be particularly germane in prostate and pancreatic cancer, given the unusually high zinc levels normally found in these tissues. It is now known that increased levels of free zinc are, inevitably, a by-product of oxidative stress. Increased free zinc can impact cellular metabolic and signaling functions, and appears to be involved in several human diseases, including cancer.

The cellular response to free zinc on the transcriptional level is mediated by the metal responsive transcription factor MTF-1, which induces the expression of metallothioneins and zinc transporters. Metallothioneins (or more properly, thioneins) are zinc-binding proteins that serve to chaperone zinc, restoring a low free zinc level. Zinc transporters also help to maintain homeostasis, by transporting zinc across plasma or other cellular membranes.

Described herein are zinc ionophores, zinc chelators and/or zinc complexes which modulate intracellular free zinc to deliver therapeutic benefit by inducing oxidative stress or altering energy metabolism. In general, the following criteria are important in the design of a zinc ionophore for treating cancer: (1) aqueous solubility—to facilitate administration and bioavailability; (2) lipid solubility—to facilitate cell entry; (3) high binding affinity to zinc—the complex does not lose an appreciable portion of bound zinc to serum proteins present in the plasma or interstitial fluid; (4) lability—sufficiently low stability within cells to release zinc.

We had previously found that MGd increased intracellular free zinc in cancer cells, presumably as a consequence of oxidation reactions involving thiols coordinated to zinc, and had observed synergistic inhibition of thioredoxin reductase in cells that were co-treated with ZnHPT, a known zinc ionophore. ZnHPT has been reported to inhibit the growth of cancer cells in culture, but is not appropriate for in vivo administration due to its limited solubility in aqueous media.

Certain Definitions

The phrase "pharmaceutical agent" as used herein, refers to any agent which imparts a therapeutic effect and is used or indicated for use as a pharmaceutical. Pharmaceutical agents may be used in the treatment, diagnosis, modulation, or prevention of a diseased state or symptom thereof. One of skill in the art is able to select appropriate pharmaceutical agents when addressing a particular disease or symptom. Exemplary pharmaceutical agents contemplated within the scope of the present disclosure are provided in the following references (the disclosures of all of which are hereby incorporated by reference): Lippincott et al., *Remington's Pharmaceutical Sciences: The Science and Practice of Pharmacy*, 20th Ed., Williams and Wilkins Publishing, Baltimore (2000); and Lewis et al., *Hawley's Condensed Chemical Dictionary*, 14th Ed., John Wiley Publishing, New York (2001).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), noncrystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizcers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

"Diluents" increase bulk of the composition to facilitate compression or create sufficient bulk for homogenous blend for capsule filling. Such compounds include e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); mannitol, hydroxypropylmethylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

The terms "pharmaceutically effective amount" or "effective amount" as used herein, refers to a nontoxic but sufficient amount of the agent to provide the desired biological, therapeutic, and/or prophylactic result. The desired results include reduction and/or alleviation of the signs, symptoms, or causes of a disease, or any other desired alteration of a biological system. An effective amount in any individual case may be determined by one of ordinary skill in the art using routine experimentation. In relation to a pharmaceutical agent, effective amounts can be dosages that are recommended in the modulation of a diseased state or symptom thereof. Effective amounts differ depending on the pharmaceutical agent used and the route of administration employed. Effective amounts are routinely optimized taking into consideration various factors of a particular patient, such as age, weight, gender, etc.

The term "pharmaceutically acceptable" or "pharmacologically acceptable" as used herein, refers a material which is not biologically active or otherwise undesirable, i.e., the material may be administered to an individual without causing any undesirable biological effects or interacting in a deleterious manner with any of the components of the composition in which it is contained. "Pharmaceutically acceptable" also refers to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio. "Pharmaceutically acceptable" also means that in a formulation containing the compound of Formula (I), Formula (Ia), Formula (Ib), Formula (II), Formula (IIa), Formula (III), Formula (IV), Formula (V), and Formula (Va), the carrier, diluent, excipients, and salt must be compatible with the other ingredients of the formulation, and not deleterious to the recipient thereof.

As used herein, "pharmaceutically acceptable carrier" or "pharmaceutically acceptable excipient" includes any and all solvents, dispersion media, coatings, antibacterial and antifungal agents, isotonic and absorption delaying agents, stabilizing agents, dispersing agents, viscosity-increasing agents, additives, and the like, depending on the dosage form used. Exemplary carrier or excipient materials include, e.g., binders, suspending agents, disintegration agents, filling agents, surfactants, solubilizers, stabilizers, lubricants, wetting agents, diluents, and the like. "Pharmaceutically compatible carrier materials" may comprise, but are not limited to, acacia, gelatin, colloidal silicon dioxide, calcium glycerophosphate, calcium lactate, cyclodextrin, amino acid carriers, protein carriers, detergents, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999). The use of such agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable derivatives" of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

Pharmaceutically acceptable salts include salts which retain the biological effectiveness and properties of the compounds of the present disclosure and which are not biologically or otherwise undesirable. In many cases, the compounds disclosed herein are capable of forming acid and/or base salts by virtue of the presence of amino and/or carboxyl groups or groups similar thereto. Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as by way of example only, alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amines, trisubstituted cycloalkyl amines, cycloalkenyl amines, di(cycloalkenyl) amines, tri(cycloalkenyl) amines, substituted cycloalkenyl amines, disubstituted cycloalkenyl amines, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Pharmaceutically acceptable acid addition salts may be prepared from inorganic and organic acids. The inorganic acids that can be used include, by way of example only, hydrochloric acid, hydrobromic acid, sulfuric acid, nitric acid, phosphoric acid, and the like. The organic acids that can be used include, by way of example only, acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The pharmaceutically acceptable salts of the compounds useful in the present disclosure can be synthesized from the parent compound, which contains a basic or acidic moiety, by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's *Pharmaceutical Sciences*, 17th ed., Mack Publishing Company, Easton, Pa. (1985), p. 1418, the disclosure of which is hereby incorporated by reference. Examples of such pharmaceutically acceptable salts are the iodide, acetate, phenyl acetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, γ-hydroxybutyrate, β-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-I-sulfonate, naphthalene-2-sulfonate, p-toluenesulfonate, xylenesulfonate, tartarate, and the like.

Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C (OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

The term "chemotherapy" as used herein, refers to the administration of one or more anti-cancer drugs and/or other agents to a cancer patient by various methods, including intravenous, intramuscular, intraperitoneal, intravesical, parenteral, or subcutaneous.

The term "treating" and its grammatical equivalents as used herein, refer to achieving, or attempting to achieve, a therapeutic benefit and/or a prophylactic benefit. By therapeutic benefit is meant eradication or amelioration, at least in part, of the underlying disorder being treated. For example, in a cancer patient, therapeutic benefit includes eradication or amelioration, at least in part, of the underlying cancer. Also, a therapeutic benefit includes the eradication or amelioration, at least in part, of one or more of the physiological symptoms associated with the underlying disorder such that an improvement is observed in the patient, notwithstanding the fact that the patient may still be afflicted with the underlying disorder. For prophylactic benefit, a method disclosed herein may be performed on, or a composition disclosed herein administered to, a patient at risk of developing cancer, or to a patient reporting one or more of the physiological symptoms of such conditions, even in the absence of a diagnosis of the condition. Specifically, the term "treatment" or "treating" includes: a) preventing the disease, that is, causing the clinical symptoms of the disease not to develop; b) inhibiting the disease, that is, arresting the development of clinical symptoms; and/or c) relieving the disease, that is, causing the regression of clinical symptoms.

The term "therapeutically effective amount" is intended to include an amount of a compound useful in the present disclosure or an amount of the combination of compounds claimed. The combination of compounds is preferably a synergistic combination. Synergy, as described for example by Chou and Talalay, *Adv. Enzyme Regul.* 22:27-55 (1984), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components. The term "synergistic combination" refers to a synergistic effect of a combination of compounds for enabling administration at a lower amount of any compound than its full strength amount without the combination for achieving a similar therapeutic effect. Alternatively, "synergistic combination" also refers to a compound's capability to mitigate adverse effects associated with another compound. Accordingly, the compound with mitigated adverse effects can be administered to provide a stronger therapeutic effect at a similar level of adverse effect without the combination.

The term "acyl" refers to moieties having the formula R—C(O)—, wherein such moieties include, but are not limited to HC(O)—, alkyl-C(O)—, substituted alkyl-C(O)—, amino-C(O)—, substituted amino-C(O)—, cycloalkyl-C(O)—, substituted cycloalkyl-C(O)—, cycloalkenyl-C(O)—, substituted cycloalkenyl-C(O)—, alkenyl-C(O)—, substituted alkenyl-C(O)—, aryl-C(O)—, substituted aryl-C(O)—, heteroaryl-C(O)—, substituted heteroaryl-C(O)—, heterocyclic-C(O)—, substituted heterocyclic-C(O)—; where alkyl, substituted alkyl, cycloalkyl, substituted cycloalkyl, cycloalkenyl, substituted cycloalkenyl, amino, substituted amino, aryl, substituted aryl, heteroaryl, substituted heteroaryl, heterocyclic and substituted heterocyclic are as defined herein. Aminoacyl groups are sometimes also referred to as amides.

The term "acyloxy" refers to moieties having the formula R—C(O)O—, wherein such moieties include, but are not limited to HC(O)—, alkyl-C(O)O—, substituted alkyl-C(O)O—, amino-C(O)O—, substituted amino-C(O)O—, cycloalkyl-C(O)O—, substituted cycloalkyl-C(O)O—, cycloalkenyl-C(O)O—, substituted cycloalkenyl-C(O)O—, alkenyl-C(O)O—, substituted alkenyl-C(O)O—, aryl-C(O)O—, substituted aryl-C(O)O—, heteroaryl-C(O)O—, substituted heteroaryl-C(O)O—, heterocyclic-C(O)O—, substituted heterocyclic-C(O)O—; where alkyl, substituted alkyl, cycloalkyl, substituted cycloalkyl, cycloalkenyl, substituted cycloalkenyl, amino, substituted amino, aryl, substituted aryl, heteroaryl, substituted heteroaryl, heterocyclic and substituted heterocyclic are as defined herein.

The term "alkaryl" refers to the groups -optionally substituted alkylene-optionally substituted aryl, where alkylene, substituted alkylene, aryl and substituted aryl are defined herein. Such alkaryl groups are exemplified by benzyl, phenethyl and the like.

The term "alkenyl" refers to a monoradical of a branched or unbranched unsaturated hydrocarbon group having from 2 to 20 carbon atoms, having 2 to 10 carbon atoms and 2 to 6 carbon atoms and having at least from 1-6 sites of vinyl unsaturation. Alkenyl groups include ethenyl (—CH=CH$_2$), 1-propylene (—CH$_2$CH=CH$_2$), isopropylene [—C(CH$_3$)=CH$_2$], and the like.

The term "optionally substituted alkenyl" refers to an alkenyl group in which at least 1 hydrogen atom has been replaced by a substituent selected from =O, =S, acyl, acyloxy, alkoxy, substituted alkoxy, amino, substituted amino, aryl, substituted aryl, aryloxy, substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, halogen, hydroxyl, nitro, phosphine, phosphonato, phosphono, sulfanyl, sulfinyl, sulfonyl, substituted phosphine, substituted phosphonato, substituted phosphono, substituted sulfanyl, substituted sulfinyl, substituted sulfonyl, cycloalkyl, substituted cycloalkyl, cycloalkenyl, substituted cycloalkenyl, acylamino, acyloxy, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, substituted heteroaryl, heteroaryloxy, substituted heteroaryloxy, heterocyclyl, substituted heterocyclyl, heterocyclooxy, substituted heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkenylene" refers to a diradical derived from the above-defined monoradical, alkenyl. This term is exemplified by groups such as ethenylene (—CH=CH—), the propenylene isomers (e.g., —CH$_2$CH=CH— and —C(CH$_3$)=CH—) and the like.

The term "substituted alkenylene" refers to an alkenylene group as defined herein having from 1 to 5 substituents, and from 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

The term "alkoxy" refers to moieties having the formula —O—R, wherein such moieties include, but are not limited to, —O-alkyl, —O-alkenyl, —O-cycloalkyl, —O-cycloalkenyl, —O-alkynyl. In addition, non-limiting examples of such —O-alkyl groups are methoxy, ethoxy, n-propoxy, iso-propoxy, n-butoxy, tert-butoxy, sec-butoxy, n-pentoxy, n-hexoxy, 1,2-dimethylbutoxy, and the like.

The term "substituted alkoxy" refers to moieties having the formula —O-(substituted alkyl), —O-(substituted alkenyl), —O-(substituted cycloalkyl), —O-(substituted cycloalkenyl), —O-(substituted alkynyl), —O-(substituted alkylene)-alkoxy. Non-limiting examples of such —O-(substituted alkylene)-alkoxy, also referred to as "polyalkoxy", are —OCH$_2$CH$_2$OCH$_3$, and polyethylene glycol (PEG) groups such as —O(CH$_2$CH$_2$O)$_x$CH$_3$, where x is an integer of about 1-20. Non-limiting examples of such —O-(substituted alkyl) groups are —OCH$_2$(CH$_2$)$_y$OH, where y is an integer of about 1-10. In other examples, y is an integer of about 1-4.

The term "alkoxyalkylene" refers to the groups: alkyl-O-alkylene-, (substituted alkyl)-O-alkylene-, alkyl-O-substituted alkylene-, (substituted alkyl)-O-(substituted alkylene). A non-limiting examples of such alkoxyalkylene group is -alkylene-O-alkyl and include, by way of example, methoxymethylene (—CH$_2$OCH$_3$), methoxyethylene (—CH$_2$CH$_2$OCH$_3$), n-(iso-propoxy)propylene [—CH$_2$CH$_2$CH$_2$OCH(CH$_3$)$_2$] and the like.

The term "alkyl" refers to a monoradical branched, cyclic, or unbranched saturated hydrocarbon chain having from 1 to 20 carbon atoms, 1 to 10 carbon atoms, or 1 to 6 carbon atoms. This term is exemplified by groups such as methyl, ethyl, n-propyl, iso-propyl, n-butyl, iso-butyl, n-hexyl, n-decyl, tetradecyl, and the like.

The term "substituted alkyl" refers to an alkyl group as defined herein, having at least 1 substituent selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl; or an alkyl group as defined herein that is interrupted by 1-20 atoms independently chosen from oxygen, sulfur and NR$^a$—, where R$^a$ is chosen from hydrogen, or optionally substituted alkyl, cycloalkyl, alkenyl, cycloalkenyl, alkenyl, cycloalkenyl, alkynyl, aryl, heteroaryl and heterocyclic; or an alkyl group as defined herein that has both from 1 to 5 substituents as defined herein and is also interrupted by 1-20 atoms as defined herein.

A non-limiting example of an alkyl substituent is hydroxy, exemplified by hydroxyalkyl groups, including but not limited to, 2-hydroxyethyl, 3-hydroxypropyl, 3-hydroxybutyl, 4-hydroxybutyl, and the like; dihydroxyalkyl groups (glycols), such as 2,3-dihydroxypropyl, 3,4-dihydroxybutyl, 2,4-dihydroxybutyl, and the like; and those compounds known as polyethylene glycols, polypropylene glycols and polybutylene glycols, and the like.

The term "alkylalkoxy" refers to the groups -alkylene-O-alkyl, alkylene-O-substituted alkyl, substituted alkylene-O-alkyl and substituted alkylene-O-substituted alkyl wherein alkyl, substituted alkyl, alkylene and substituted alkylene are as defined herein. Examples of alkylalkoxy groups are alkylene-O-alkyl and include, by way of example, methylenemethoxy (—CH$_2$OCH$_3$), ethylenemethoxy (—CH$_2$CH$_2$OCH$_3$), n-propylene-iso-propoxy (—CH$_2$CH$_2$CH$_2$OCH(CH$_3$)$_2$), methylene-t-butoxy (—CH$_2$—O—C(CH$_3$)$_3$) and the like.

The term "alkylene" refers to a diradical of a branched, cyclic, or unbranched saturated hydrocarbon chain, having from 1 to 20 carbon atoms, 1-10 carbon atoms, 1-6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group as defined herein having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where two substituents on the alkylene group are fused to form one or more cycloalkyl, substituted cycloalkyl, cycloalkenyl, substituted cycloalkenyl, aryl, heterocyclic or heteroaryl groups fused to the alkylene group; or an alkylene group as defined herein that is interrupted by 1-20 atoms independently chosen from oxygen, sulfur and NR$^a$—, where R$^a$ is chosen from hydrogen, optionally substituted alkyl, cycloalkyl, alkenyl, cycloalkenyl, alkenyl, cycloalkenyl, alkynyl, aryl, heteroaryl and heterocyclic, or groups selected from carbonyl, carboxyester, carboxyamide and sulfonyl; or an alkylene group as defined herein that has both from 1 to 5 substituents as defined herein and is also interrupted by 1-20 atoms as defined herein.

Examples of substituted alkylenes are chloromethylene (—CH(Cl)—), aminoethylene (—CH(NH$_2$)CH$_2$—), 2-carboxypropylene isomers (—CH$_2$CH(CO$_2$H)CH$_2$—), ethoxyethyl (—CH$_2$CH$_2$O—CH$_2$CH$_2$—), ethylmethylaminoethyl (—CH$_2$CH$_2$N(CH$_3$)CH$_2$CH$_2$—), 1-ethoxy-2-(2-ethoxyethoxy)ethane (—CH$_2$CH$_2$O—CH$_2$CH$_2$—OCH$_2$CH$_2$—OCH$_2$CH$_2$—), and the like.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein. Alkylthioalkoxy groups include alkylene-S-alkyl, by way of example, methylenethiomethoxy (—CH$_2$SCH$_3$), ethylenethiomethoxy (—CH$_2$CH$_2$SCH$_3$), n-propylene-iso-thiopropoxy (—CH$_2$CH$_2$CH$_2$SCH(CH$_3$)$_2$), methylene-t-thiobutoxy (—CH$_2$SC(CH$_3$)$_3$) and the like.

The term "alkynyl" refers to a monoradical of an unsaturated hydrocarbon, having from 2 to 20 carbon atoms, 2 to 10 carbon atoms and 2 to 6 carbon atoms and having at least from 1-6 sites of acetylene (triple bond) unsaturation. Examples of alkynyl groups include ethynyl, (—C≡CH), propargyl, (—C≡CCH$_3$), and the like.

The term "substituted alkynyl" refers to an alkynyl group as defined herein having from 1 to 5 substituents, and preferably 1 to 3 substituents, selected from the group consisting of:

=O, =S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, phosphonato, phosphono, sulfanyl, sulfinyl, sulfonyl, cycloalkenyl, substituted cycloalkenyl, acylamino, aminoacyl, aminoacyloxy, oxyaminoacyl, azido, keto, thioketo, carboxyl, carboxylalkyl, thioaryloxy, thioheteroaryloxy, thioheterocyclooxy, thiol, thioalkoxy, substituted thioalkoxy, alkoxyamino, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "alkynylene" refers to a diradical of an unsaturated hydrocarbon preferably having from 2 to 20 carbon atoms, more preferably 2 to 10 carbon atoms and even more preferably 2 to 6 carbon atoms and having at least 1 and preferably from 1-6 sites of acetylene (triple bond) unsaturation. Examples of alkynylene groups include ethynylene (—C≡C—), propargylene (—CH$_2$—C≡C—) and the like.

The term "substituted alkynylene" refers to an alkynylene group as defined herein having from 1 to 5 substituents, and preferably 1 to 3 substituents, selected from the group consisting of: =O, =S, acyl, acyloxy, optionally substituted alkoxy, optionally substituted amino, optionally substituted aryl, optionally substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, optionally substituted cycloalkyl, halogen, optionally substituted heteroaryl, optionally substituted heteroaryloxy, optionally substituted heterocyclyl, optionally substituted heterocyclooxy, hydroxyl, nitro, optionally substituted phosphine, phosphonato, phosphono, sulfanyl, sulfinyl, sulfonyl, cycloalkenyl, substituted cycloalkenyl, acylamino, aminoacyl, aminoacyloxy, oxyaminoacyl, azido, keto, thioketo, carboxyl, carboxylalkyl, thioaryloxy, thioheteroaryloxy, thioheterocyclooxy, thiol, thioalkoxy, substituted thioalkoxy, alkoxyamino, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "acylamino" or "aminocarbonyl" refers to the group —C(O)NRR or —NRC(O)R where each R is independently hydrogen, alkyl, substituted alkyl, aryl, heteroaryl, heterocyclic or where both R groups are joined to form a heterocyclic group (e.g., morpholino) wherein alkyl, substituted alkyl, aryl, heteroaryl and heterocyclic are as defined herein.

The term "amino" refers to the group —NH$_2$.

The term "substituted amino" refers to the group —NHR or —NRR where each R is independently selected from the group: hydrogen, acyl, optionally substituted alkenyl, optionally substituted alkyl, optionally substituted alkoxy, optionally substituted alkoxycarbonyl, optionally substituted alkynyl, optionally substituted aminocarbonyl, optionally substituted aryl, carboxy, optionally substituted cycloalkyl, optionally substituted cycloalkenyl, optionally substituted cycloalkenyl, optionally substituted heteroaryl, and optionally substituted heterocyclyl. Examples of amino substituents include optionally substituted alkyl, aryl, optionally substituted alkoxycarbonyl, optionally substituted aminocarbonyl, and heteroaryl.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" or "alkoxycarbonylamino" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "apical ligand" refers to an anion that binds to the core metal of the metallotexaphyrin, e.g., with de-localized electrostatic or weak coordinate-covalent bonds. The number of apical ligands (n) is defined as an integer of 1-5. It should be noted that the apical ligands act to neutralize the charge on the metallotexaphyrin. Thus, typically n is 1 when M is a divalent cation, and n is 2 when M is a trivalent cation (because the core itself neutralizes one unit charge). However, if any of $R^1, R^{1'}, R^2, R^3, R^4, R^{4'}, R^5, R^6, R^7, R^8, R^9, R^{10}, R^{11}$ and $R^{12}$ is capable of forming an acid addition salt, for example a carboxylate or a phosphate, then n can decrease appropriately. It is also possible that the apical ligands could have two functionalities capable of forming an anion, for example a dicarboxylic acid, and such ligands are intended to be within the scope of the present disclosure. In general, any molecule containing a carboxylic acid or phosphate may be used as an apical ligand, for example biomolecules, including lipoproteins, estradiol and amino acids, carboxylates of sugar derivatives, such as gluconic acid or glucoronic acid, cholesterol derivatives such as cholic acid and deoxycholic acid, PEG acids, PPG acids, organophosphates, such as methylphosphonic acid and phenylphosphonic acid, and phosphoric acid or other inorganic acids, and the like, or sulfonic acid derivatives such as methanesulfonic acid, ethanesulfonic acid. or "carboxylic acid derivatives", which term refers to compounds of the formula R—CO$_2$H, in which R is optionally substituted alkyl, optionally substituted alkenyl, optionally substituted alkynyl, or optionally substituted aryl, as defined above. Examples include gluconic and glucuronic acid, and those carboxylic acid derivatives where R is optionally substituted alkyl, for example acids of 1-20 carbon atoms, such as formic acid, acetic acid, propionic acid, butyric acid, pentanoic acid, 3,6,9-trioxodecanoic acid, 3,6-dioxoheptanoic acid, methylvaleric acid, glycolic acid, pyruvic acid, oxalic acid, malic acid, malonic acid, succinic acid, maleic acid, fumaric acid, tartaric acid, citric acid, and the like. Also applicable are those carboxylic acid derivatives where R is aryl, in particular where R is optionally substituted phenyl, for example benzoic acid, salicylic acid, 3-fluorobenzoic acid, 4-aminobenzoic acid, cinnamic acid, mandelic acid, p-toluene-sulfonic acid, and the like. Other examples of apical ligands include: OH$^-$, AcO$^-$, Cl$^-$, Br$^-$, I$^-$, F$^-$, H$_2$PO$_4^-$, ClO$^-$, ClO$_2^-$, ClO$_3^-$, ClO$_4^-$, HCO$_3^-$, HSO$_4^-$, NO$_3^-$, N$_3^-$, CN$^-$, SCN$^-$, and OCN$^-$.

The term "aromatic" refers to a cyclic or polycyclic moiety having a conjugated unsaturated (4n+2) π-electron system (where n is a positive integer), sometimes referred to as a delocalized π-electron system.

The term "aryl" refers to an unsaturated aromatic carbocyclic group of from 6 to 20 carbon atoms having a single ring (e.g., phenyl) or multiple condensed (fused) rings (e.g., naphthyl or anthryl). Examples of aryls include phenyl, naphthyl and the like.

Unless otherwise constrained by the definition for the aryl substituent, such aryl groups can optionally be substituted with from 1 to 5 substituents, 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocloxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Examples of aryl substituents include alkyl, alkoxy, halo, cyano, nitro, trihalomethyl, and thioalkoxy.

The term "aralkyl" refers to the moiety "-arylene-alkyl," each subpart having the meaning as defined herein.

The term "substituted aralkyl" refers to the moiety "-(optionally substituted arylene)-(optionally substituted alkyl)", each having the meaning as defined herein.

The term "aryloxy" refers to the group aryl-O— wherein the aryl group is as defined herein including optionally substituted aryl groups as also defined herein.

The term "arylene" refers to the diradical derived from aryl (including substituted aryl) as defined herein and is exemplified by 1,2-phenylene, 1,3-phenylene, 1,4-phenylene, 1,2-naphthylene and the like.

The term "carbonyl" refers to the di-radical "—C(=O)—" which is also written as "—C(O)—".

The terms "optionally substituted" or "substituted" refers to a group (unless otherwise specificied elsewhere herein) in which at least 1 hydrogen atom has been replaced by a substituent selected from =O, =S, acyl, acyloxy, alkoxy, substituted alkoxy, amino, substituted amino, aryl, substituted aryl, aryloxy, substituted aryloxy, carboxyl, (optionally substituted alkoxy)carbonyl, (optionally substituted amino)carbonyl, (optionally substituted alkoxy)carbonyloxy, (optionally substituted amino)carbonyloxy, cyano, halogen, hydroxyl, nitro, phosphine, phosphonato, phosphono, sulfanyl, sulfinyl, sulfonyl, substituted phosphine, substituted phosphonato, substituted phosphono, substituted sulfanyl, substituted sulfinyl, substituted sulfonyl, cycloalkyl, substituted cycloalkyl, cycloalkenyl, substituted cycloalkenyl, acylamino, acyloxy, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocloxy, thiol, thioalkoxy, substituted thioalkoxy, aryl, aryloxy, heteroaryl, substituted heteroaryl, heteroaryloxy, substituted heteroaryloxy, heterocyclyl, substituted heterocyclyl, heterocloxy, substituted heterocloxy, hydroxyamino, alkoxyamino, nitro, polyether, hydroxylated group, saccharide, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

The term "(optionally substituted alkoxy)carbonyl" refers to the groups: —C(O)O-(optionally substituted alkyl), —C(O)O-(optionally substituted cycloalkyl), —C(O)O-(optionally substituted alkenyl), and —C(O)O-(optionally substituted alkynyl). These moieties are also referred to as esters, carboxylalkyls or alkoxycarbonyls.

The term "(optionally substituted amino)carbonyl" refers to the group —C(O)-(optionally substituted amino). This moiety is also referred to as an amide, or a primary, secondary or tertiary carboxamide.

The term "(optionally substituted alkyl)carbonyloxy" refers to the group —O—C(O)-(optionally substituted alkyl).

The term "(optionally substituted amino)carbonyloxy" refers to the group —O—C(O)-(optionally substituted amino).

The term "carboxy" or "carboxyl" refers to the moiety "—C(O)OH", which is also illustrated as "—COOH".

The term "catalytic group" means a chemical functional group that assists catalysis by acting as a general acid, Bronsted acid, general base, Bronsted base, nucleophile, or any other means by which the activation barrier to reaction is lowered. Exemplary catalytic groups contemplated include, but are not limited to, imidazole; guanidine; substituted saccharides such as D-glucosamine, D-mannosamine, D-galactosamine, D-glucamine and the like; amino acids such as L-histidine and L-arginine; derivatives of amino acids such as histamine; polymers of amino acids such as poly-L-lysine, (LysAla), (LysLeuAla)$_n$ where n is from 1-30 or 1-10 or 2-7 and the like; derivatives thereof; and metallotexaphyrin complexes.

The term "carboxyalkyl" or "alkoxycarbonyl" refers to the groups "—C(O)O-alkyl", "—C(O)O-substituted alkyl", "—C(O)O-cycloalkyl", "—C(O)O-substituted cycloalkyl", "—C(O)O-alkenyl", "—C(O)O-substituted alkenyl", "—C(O)O-alkynyl" and "—C(O)O-substituted alkynyl" where alkyl, substituted alkyl, cycloalkyl, substituted cycloalkyl, alkenyl, substituted alkenyl, alkynyl and substituted alkynyl are as defined herein.

The term "carboxyamides" include primary carboxyamides (CONH$_2$), secondary carboxyamides (CONHR') and tertiary carboxyamides (CONR'R"), where R' and R" are the same or different substituent groups chosen from alkyl, alkenyl, alkynyl, alkoxy, aryl, a heterocyclic group, a functional group as defined herein, and the like, which themselves may be substituted or unsubstituted.

"Carboxyamidealkyl" means a carboxyamide as defined herein attached to an optionally substituted alkylene group as defined herein.

The term "chemotherapy" as described herein, refers to the administration of one or more anti-cancer drugs and/or other agents to a cancer patient by various methods, including intravenous, oral, intramuscular, intraperitoneal, intravesical, subcutaneous, transdermal, buccal, or inhalation or in the form of a suppository.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "cycloalkylene" refers to the diradical derived from cycloalkyl as defined herein and is exemplified by 1,1-cyclopropylene, 1,2-cyclobutylene, 1,4-cyclohexylene and the like.

The term "substituted cycloalkyl" refers to cycloalkyl groups having from 1 to 5 substituents, and preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocloxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Examples of aryl substituents include alkyl, alkoxy, halo, cyano, nitro, trihalomethyl, and thioalkoxy.

The term "substituted cycloalkylene" refers to the diradical derived from substituted cycloalkyl as defined herein.

The term "cycloalkenyl" refers to cyclic alkenyl groups of from 4 to 20 carbon atoms having a single cyclic ring and at least one point of internal unsaturation. Examples of suitable cycloalkenyl groups include, for instance, cyclobut-2-enyl, cyclopent-3-enyl, cyclooct-3-enyl and the like.

The term "cycloalkenylene" refers to the diradical derived from cycloalkenyl as defined herein and is exemplified by 1,2-cyclobut-1-enylene, 1,4-cyclohex-2-enylene and the like.

The term "substituted cycloalkenyl" refers to cycloalkenyl groups having from 1 to 5 substituents, and preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Embodiments disclosed herein having aryl substituents include alkyl, alkoxy, halo, cyano, nitro, trihalomethyl, and thioalkoxy.

The term "substituted cycloalkenylene" refers to the diradical derived from substituted cycloalkenyl as defined herein.

The term "dipyrromethene" refers to compounds having the core structure:

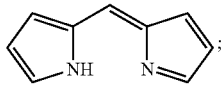 [SMILES: C1=C/C(=C/c2ccc[nH]2)N=C1]

having from 0 to 5 substituents, and 0 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

The term "halo" or "halogen" refers to fluoro, chloro, bromo and iodo.

The term "heteroaryl" refers to an aromatic group comprising 1 to 15 carbon atoms and 1 to 4 heteroatoms selected from oxygen, nitrogen and sulfur within at least one ring (if there is more than one ring). Unless otherwise constrained by the definition for the heteroaryl substituent, such heteroaryl groups can be optionally substituted with 1 to 5 substituents, preferably 1 to 3 substituents, selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl. Examples of aryl substituents include alkyl, alkoxy, halo, cyano, nitro, trihalomethyl, and thioalkoxy. Such heteroaryl groups can have a single ring (e.g., pyridyl or furyl) or multiple condensed rings (e.g., indolizinyl or benzothienyl). Embodiments disclosed herein include heteroaryls, such as by way of example only, pyridyl, pyrrolyl and furyl.

The term "heteroaryloxy" refers to the group heteroaryl-O—.

The term "heteroarylene" refers to the diradical group derived from heteroaryl (including substituted heteroaryl), as defined herein, and is exemplified by the groups 2,6-pyridylene, 2,4-pyridiylene, 1,2-quinolinylene, 1,8-quinolinylene, 1,4-benzofuranylene, 2,5-pyridnylene, 2,5-indolenyl and the like.

The term "heterocycle" or "heterocyclic" refers to a monoradical saturated or unsaturated group having a single ring or multiple condensed rings, having from 1 to 40 carbon atoms and from 1 to 10 hetero atoms, 1 to 4 heteroatoms, selected from nitrogen, sulfur, phosphorus, and/or oxygen within the ring. Unless otherwise constrained by the definition for the heterocyclic substituent, such heterocyclic groups can be optionally substituted with 1 to 5, and 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. Such heterocyclic groups can have a single ring or multiple condensed rings. Examples of heterocyclics include morpholino, piperidinyl, and the like.

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

The term "heterocyclooxy" refers to the group heterocyclic-O—.

The term "heterocyclene" refers to the diradical group formed from a heterocycle, as defined herein, and is exemplified by the groups 2,6-morpholino, 2,5-morpholino and the like.

The term "isomers" as used herein refers to molecules with the same chemical formula, but possessing different properties. By way of example only, isomers can include structural isomers, geometric isomers, optical isomers, and stereoisomers, such as by way of example only, diastereomers, enantiomers, and atropisomers. Generally, atropisomers result from hindered rotation about single bonds where the steric strain barrier to rotation is high enough to allow for the isolation of the conformers.

The term "linker" as used herein means a covalent connection of a functional group (e.g., a site directing group, a catalytic group or a neuroprotective agent) to a metallotexaphyrin, and may be, for example, a covalent bond or an alkylene, alkenylene, alkynylene, arylene, ethers, PEG moieties, PPG moieties, and the like, all of which may be optionally substituted. Examples of reactions to form a covalent link include reaction between an amine (on either the functional group or the linker precursor) with a carboxylic acid (on the other) to form an amide link. Similar reactions well known in the art are described in standard organic chemistry texts such as J. March, "Advanced Organic Chemistry", 4$^{th}$ Edition, (Wiley-Interscience (New York), 1992.

The term "on each side of Formula" refers to each aryl group of a zinc ionophore, zinc complex and/or zinc chelator having independently substituted groups, such as by way of example only, each $R_0$ of Formula (I) may be substituted independently by different substituents or the same substituent, such that for example, one $R_0$ may be substituted by H and the other $R_0$ may be subsituted by OH or for example, both $R_0$ substituents may be substituted by H.

The term "phosphate" refers to the group —O—PO$_3$H$_2$. One or more of the hydrogen atoms on the phosphate group may be substituted with alkyl, alkenyl, alkynyl, aryl, heteroaryl, or heterocycyle.

The term "phosphine" refers to the group —PH$_2$.

The term "substituted phosphine" refers to the group —PR'R" where R' and R" are selected from the group: hydrogen, alkyl, alkoxy and aryl, and at least one of R' or R" is not hydrogen.

The term "oxyacylamino" or "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

The term "phosphonato" refers to the group —P(O)(O$^-$)$_2$, which, depending upon whether one or more of the oxygen anions is linked to another moiety (such as ribose, in the case of RNA) is sometimes also referred to as a phosphodiester linkage.

The term "phosphono" refers to the group —P(O)(OH)$_2$, which is sometimes also referred to as a phosphate. One or more of the hydrogen atoms on the phosphate group may be substituted with alkyl, alkenyl, alkynyl, aryl, heteroaryl, or heterocycyle.

A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. An example, without limitation, of a prodrug would be a compound of Formula (I), Formula (Ia), Formula (Ib), Formula (II), Formula (IIa), Formula (III), Formula (IV), Formula (V), and Formula (Va) which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety.

The term "protecting group" refers to chemical moieties that block some or all reactive moieties and prevent such groups from participating in chemical reactions until the protective group is removed. It is preferred that each protective group be removable by a different means. Protective groups that are cleaved under totally disparate reaction conditions fulfill the requirement of differential removal. Protective groups can be removed by acid, base, light, microwaves, and hydrogenolysis. Groups such as trityl, dimethoxytrityl, acetal and t-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as t-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be protected by conversion to simple ester derivatives as exemplified herein, or they may be blocked with oxidatively-removable protective groups such as 2,4-dimethoxybenzyl, while co-existing amino groups may be blocked with fluoride labile silyl carbamates.

Allyl blocking groups are useful in then presence of acid- and base-protecting groups since the former are stable and can be subsequently removed by metal or pi-acid catalysts. For example, an allyl-blocked carboxylic acid can be deprotected with a Pd$_0$-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typically blocking/protecting groups may be selected from:

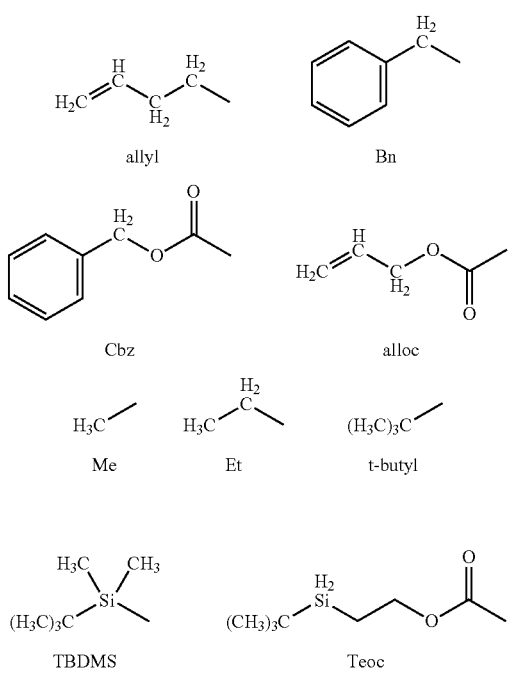

-continued

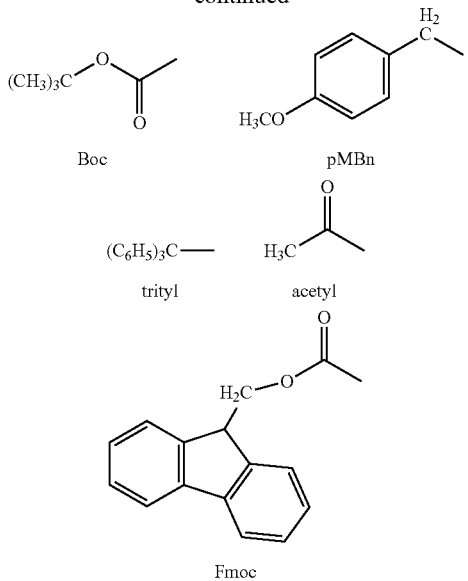

Other protecting groups are described in Greene and Wuts, Protective Groups in Organic Synthesis, 3rd Ed., John Wiley & Sons, New York, N.Y., 1999, which is incorporated herein by reference in its entirety.

The term "site-directing group" refers to a functional group having an affinity for a biological receptor or for a nucleic acid sequence. Exemplary site-directing groups useful herein include, but are not limited to, polydeoxyribonucleotides, oligodeoxyribonucleotides, polyribonucleotide analogs, oligoribonucleotide analogs, polyamides including peptides having affinity for a biological receptor and proteins such as antibodies, steroids and steroid derivatives, hormones such as estradiol or histamine, hormone mimics such as morphine, and further macrocycles such as sapphyrins and rubyrins. The oligonucleotides may be derivatized at the bases, the sugars, the ends of the chains, or at the phosphate groups of the backbone to promote in vivo stability. Modifications of the phosphate groups are preferred in one embodiment since phosphate linkages are sensitive to nuclease activity. Presently preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include groups, such as halo, alkyl, alkenyl or alkoxy groups, attached to an oxygen of a ribose moiety in a ribonucleotide. In a preferred embodiment, the group will be attached to the 2' oxygen of the ribose. In particular, halogen moieties such as fluoro may be used. The alkoxy group may be methoxy, ethoxy or propoxy. In one embodiment the alkenyl group is allyl. In another embodiment, the alkyl group is a methyl group and the methyl group is attached to the 2' oxygen of the ribose. Other alkyl groups may be ethyl or propyl. It is understood that the terms "nucleotide", "polynucleotide" and "oligonucleotide", as used herein, refer to both naturally-occurring and synthetic nucleotides, poly- and oligonucleotides and to analogs and derivatives thereof such as methylphosphonates, phosphotriesters, phosphorothioates, phosphoramidates and the like. Deoxyribonucleotides, deoxyribonucleotide analogs and ribonucleotide analogs are contemplated as site-directing groups in the present disclosure. The term "texaphyrin-oligonucleotide conjugate" means that an oligonucleotide is attached to the texaphyrin in a 5' or a 3' linkage, or in both types of linkages to allow the texaphyrin to be an internal residue in the conjugate. It can also refer to a texaphyrin that is linked to an internal base of the oligonucleotide. The oligonucleotide or other site-directing group may be attached either directly to the texaphyrin or to the texaphyrin via a linker or a couple of variable length.

The term "sulfanyl" refers to the groups: —S-(optionally substituted alkyl), —S-(optionally substituted aryl), —S-(optionally substituted heteroaryl), —S-(optionally substituted heterocyclyl). Examples of sulfanyl groups include, by way of example, methylsulfanyl (—$SCH_3$), n-(iso-propylsulfanyl) (—$SCH(CH_3)_2$) and the like.

The term "sulfinyl" refers to the groups: —S(O)-(optionally substituted alkyl), —S(O)-optionally substituted aryl), —S(O)-(optionally substituted heteroaryl), —S(O)-(optionally substituted heterocyclyl). Examples of sulfinyl groups include, by way of example, methylsulfinyl (—S(O)—$CH_3$) and the like.

The term "sulfonyl" refers to the groups: —$S(O_2)$-(optionally substituted alkyl), —$S(O_2)$-optionally substituted aryl), —$S(O_2)$-(optionally substituted heteroaryl), —$S(O_2)$-(optionally substituted heterocyclyl). Examples of sulfonyl groups include, by way of example, methylsulfonyl (—$S(O_2)$—$CH_3$) and the like.

"Texaphyrin" means an aromatic pentadentate macrocyclic expanded porphyrins, also described as an aromatic benzannulene containing both $18\pi$- and $22\pi$-electron delocalization pathways. Texaphyrins and water-soluble texaphyrins, methods of preparation and various uses and the like have been described, for example, in U.S. Pat. Nos. 4,935,498, 5,162,509, 5,252,720, 5,256,399, 5,272,142, 5,292,414, 5,369,101, 5,432,171, 5,439,570, 5,451,576, 5,457,183, 5,475,104, 5,504,205, 5,525,325, 5,530,122, 5,559,207, 5,565,552, 5,567,687, 5,569,759, 5,580,543, 5,583,220, 5,587,371, 5,587,463, 5,591,422, 5,594,136, 5,595,726, 5,599,923, 5,599,928, 5,601,802, 5,607,924, 5,622,946, 5,714,328, 5,733,903, 5,744 302, 5,756,726, 5,763,172, 5,775,339, 5,776,925, 5,798,491, 5,801,229, 5,808,059, 5,817,017, 5,837,866, 5,886,173, 5,888,997, 5,955,586, 5,969,111, 5,994,935, 6,022,526, 6,022,959, 6,069,140, 6,072,038 6,096,030, 6,207,660, 6,270,749, 6,375,930, 6,638,924, 6,657,058, 6,825,186, 6,919,327, 7,112,671, in PCT publications WO 90/10633, 94/29316, 95/10307, 95/21845, 96/09315, 96/40253, 96/38461, 97/26915, 97/35617, 97/46262, 98/07733, 98/25648, 99/09411, 99/15236, 99/62551, 00/01413, 00/01414, 03/37888; 05/112759; and in pending U.S. patent application Ser. Nos. 10/160,205, 10/659,499, 10/310,592, 10/362,964, 10/318, 659, 10/911,284, 11/241,549, 11/235,475, and 60/737,601, each of which are herein incorporated by reference in their entirety.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclic-S—.

The term "saccharide" includes oxidized, reduced or substituted saccharides, including hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosaccharides; as well as closed and open chain forms of sugars, and the like. Examples of amine-derivatized sugars are galactosamine, glucosamine, and sialic acid.

The term "optionally substituted polyether" refers to any group of the formula O-(alkylene-O)$_n$-alkyl, where n is a number between 1 and 100, 1 and 10, and wherein the alkylene and alkyl groups are optionally substituted as defined herein.

The term "substituted hydroxylated group" refers to any chemical group defined herein in which one or more —OH groups are present; further optional substituents on such a hydroxylated group are permitted as defined herein for each chemical group, e.g., a substituted hydroxylated alkyl group has at least one —OH group, but also has other substituents on other portions of the alkyl group (e.g., —CHClCH$_2$OH).

The term "zinc," "free zinc" or the like, unless specifically stated otherwise, refers to the zinc dication, i.e., $Zn^{2+}$.

The term "zinc chelator," as used herein, refers to a multidentate ligand that can coordinate to a zinc ion to form a zinc complex.

The term "zinc complex," as used herein, refers to at least one zinc ion chelated by at least one multi-dentate ligand (i.e., bidentate, tridentate, tetradentate, etc.). The zinc complex can include mono-dentate ligands. The multi-dentate ligand of a zinc complex can be replaced by other ligands to form a new zinc complex, or a zinc ion having only mono-dentate zinc ligands.

The term "zinc ionophore" refers to a zinc complex that effects transport of zinc from the extracellular space to the intracellular space, or vice versa.

The term "zinc ligand" as used herein refers to a ligand, monodentate or multidentate that can coordinate to zinc.

The term "bioavailability," as used herein, refers to the rate and extent to which a substance or its active moiety is delivered from a pharmaceutical dosage form and becomes available at the site of action or in the general circulation. Increases in bioavailability refers to increasing the rate and extent a substance or its active moiety is delivered from a pharmaceutical dosage form and becomes available at the site of action or in the general circulation. By way of example, an increase in bioavailability may be indicated as an increase in concentration of the substance or its active moiety in the blood when compared to other substances or active moieties.

Zinc Ionophores/Zinc Complexes/Zinc Chelators

Zinc ionophores, zinc chelators and/or zinc complexes with enhanced aqueous solubility have increased bioavailability upon administration as compared to zinc ionophores, zinc chelators and/or zinc complexes with poor aqueous solubility.

One aspect described herein relates to zinc ionophores or zinc complexes, comprising the structure of Formula (I):

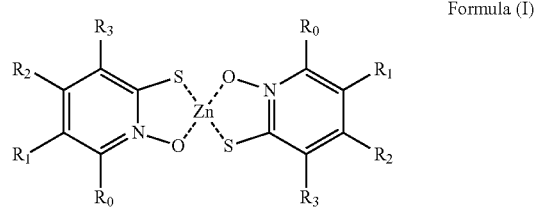

Formula (I)

wherein:

each $R_0$, each $R_1$, each $R_2$, and each $R_3$ on each side of Formula (I) is independently H, OH, NH$_2$, NO$_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or L$_1$X$_n$L$_2$-; provided that at least one of the R$_0$, R$_1$, R$_2$, or R$_3$ groups is L$_1$X$_n$L$_2$-;

each L$_1$ is independently H, OH, NH$_2$, halogen, —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20; and each L$_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R)—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

optionally, one of R$_0$, R$_1$, R$_2$, or R$_3$ on one side of Formula (I) may be attached by L to one of R$_0$, R$_1$, R$_2$, or R$_3$ on the other side of Formula (I);

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

For zinc ionophores or zinc complexes having a structure of Formula (I), in some embodiments described herein, each of $R_0$, $R_1$, $R_2$, and $R_3$ are the same on each side of Formula (I), lower alkyl, (CH$_2$)$_v$—OR$_y$, OR$_y$, NHR$_y$, C(O)NHR$_y$, wherein R$_y$ is PEG or PPG; wherein PEG or PPG is —(O-alkylene or O-substituted alkylene)$_x$-O—R$_z$ or -(alkylene-O or substituted alkylene-O)$_x$—R$_z$, where R$_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H ; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, R$_1$ is CH$_2$—OPEG; and R$_0$R$_2$, and R$_3$ are H. In some embodiments, R$_3$ is OPEG; and R$_0$, R$_1$, and R$_2$ are H. In some embodiments, R$_2$ is OPEG; and R$_0$, R$_1$, and R$_3$ are H. In some embodiments, R$_2$ and R$_3$ are OPEG; and R$_0$ and R$_1$ are H. In some embodiments, R$_2$ is NHPEG; and R$_0$, R$_1$, and R$_3$ are H. In some embodiments, R$_1$ is OPEG; and R$_0$, R$_2$, and R$_3$ are H. In some embodiments, R$_1$ is CH$_2$—OPPG; and R$_0$, R$_2$, and R$_3$ are H. In some embodiments, R$_3$ is OPPG; and R$_0$, R$_1$, and R$_2$ are H. In some embodiments, R$_0$ is CH$_3$, R$_1$, R$_2$ is H and R$_3$ is OCH$_2$CH$_2$OCH$_3$. In one embodiment, R$_0$ is CH$_3$, R$_1$, R$_2$ is H; and R$_3$ is OCH$_2$CH$_2$OCH$_2$CH$_2$OCH$_3$. In some embodiments, R$_2$ is OPPG; and R$_0$, R$_1$, and R$_3$ are H. In some embodiments, R$_2$ and R$_3$ are OPPG; and R$_0$ and R$_1$ are H. In some embodiments, R$_2$ is NHPPG; and R$_0$, R$_1$, and R$_3$ are H. In some embodiments, R$_1$ is OPPG; and R$_0$, R$_2$, and R$_3$ are H. In one embodiment, R$_1$, R$_2$, and R$_3$ are H; and R$_0$ is OPEG-(C$_6$H$_5$). In another embodiment, R$_1$, R$_2$, and R$_3$ are H; and R$_0$ is OPPG-(C$_6$H$_5$). In one embodiment is a zinc ionophore or zinc complex of compound 50a-50c. In some embodiments, R$_1$ is C(O)NHR$_y$, R$_0$, R$_2$, and R$_3$ are H. In another embodiment is a zinc ionophore or zinc complex of compound 17.

For zinc ionophores or zinc complexes having a structure of Formula (I), in some embodiments described herein, each of $R_0$, $R_1$, $R_2$, and $R_3$ is independently the same on each side of Formula (I), or an optionally substituted group selected from a mono-hydroxylated group, a dihydroxylated group, a tri-hydroxylated group, a tetra-hydroxylated group, a penta-hydroxylated group, or a saccharide.

For zinc ionophores or zinc complexes having a structure of Formula (I), in some embodiments described herein, each of $R_0$, $R_1$, $R_2$, and $R_3$ is independently the same on each side of Formula (I), L, wherein L is PEG or PPG; wherein PEG or PPG is —(O-alkylene or O-substituted alkylene)$_x$-O—R$_z$ or -(alkylene-O or substituted alkylene-O)$_x$R$_z$, where R$_z$ is H, alkyl, R$_0$, R$_1$, R$_2$, or R$_3$; and x is 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OR$_z$ or —(CH$_2$CH$_2$O)$_x$R$_z$. In some embodiments, PPG is —(OCH$_2$CH$_2$CH$_2$)$_x$OR$_z$; —(CH$_2$CH$_2$CH$_2$O)$_x$R$_z$; —(OCH(CH$_3$)CH$_2$)$_x$OR$_z$; —(CH(CH$_3$)CH$_2$)$_x$R$_z$; —(OCH$_2$CH(CH$_3$))$_x$OR$_z$; or —(OCH$_2$CH(CH$_3$))$_x$R$_z$. In some embodiments, one R$_0$ is attached to another R$_0$ on the other side of Formula (I) via OPEGO; and R$_1$, R$_2$, and R$_3$ are H. In some embodiments, one R$_1$ is attached to another R$_1$ on the other side of Formula (I) via OPEGO; and R$_0$, R$_2$, and R$_3$ are H. In some embodiments, R$_2$ is attached to another R$_2$ on the other side of Formula (I) via OPEGO; and R$_0$, R$_1$, and R$_3$ are H. In some embodiments, one R$_2$ is attached to one R$_3$ on the other side of Formula (I) via OPEGO; and R$_0$ and R$_1$ and the other R$_2$ and R$_3$ are H. In some embodiments, one R$_1$ is attached to one R$_3$ on the other side of Formula (I) via OPEGO; and R$_0$ and R$_2$ and the other R$_1$ and R$_3$ are H. In some embodiments, one R$_0$ is attached to one R$_3$ on the other side of Formula (I) via OPEGO; and R$_2$ and R$_1$ and the other R$_0$ and R$_3$ are H. In some embodiments, one R$_0$ is attached to one R$_1$ on the other side of Formula (I) via OPEGO; and R$_2$ and R$_3$ and the other R$_0$ and R$_1$ are H. In some embodiments, one R$_1$ is attached to one R$_2$ on the other side of Formula (I) via OPEGO; and R$_0$ and R$_3$ and the other R$_1$ and R$_2$ are H. In some embodiments, one R$_0$ is attached to one R$_2$ on the other side of Formula (I) via OPEGO; and R$_1$ and R$_3$ and the other R$_0$ and R$_2$ are H. In some embodiments, are the compounds 37a-37e. In other embodiments the PEG group is substituted with the PPG group.

In one embodiment, at least one R$_0$, R$_1$, R$_2$, R$_3$ on one side of Formula (I) is attached to at least one R$_0$, R$_1$, R$_2$, R$_3$ of the other side of Formula (I) via OPEGO. In some embodiments, one R$_0$ is attached to another R$_0$ on the other side of Formula (I) via OPEGO; and one R$_3$ is attached to another R$_3$ on the other side of Formula (I) via OPEGO; and R$_1$, and R$_2$ are H. In some embodiments, one R$_0$ is attached to another R$_0$ on the other side of Formula (I) via OPEGO; and one R$_2$ is attached to another R$_2$ on the other side of Formula (I) via OPEGO; and R$_1$, and R$_3$ are H. In some embodiments, one R$_0$ is attached to another R$_0$ on the other side of Formula (I) via OPEGO; and one R$_1$ is attached to another R$_1$ on the other side of Formula (I) via OPEGO; and R$_2$, and R$_3$ are H. In some embodiments, one R$_3$ is attached to another R$_3$ on the other side of Formula (I) via OPEGO; and one R$_1$, is attached to another R$_1$ on the other side of Formula (I) via OPEGO; and R$_0$, and R$_2$ are H. In some embodiments, one R$_3$ is attached to another R$_3$ on the other side of Formula (I) via OPEGO; and one R$_2$ is attached to another R$_1$ on the other side of Formula (I) via OPEGO; and R$_2$, and R$_3$ are H. In one embodiment, R$_0$, R$_1$ is attached to R$_1$, R$_0$ on the other side of Formula (I) respectively, via OPEGO; and R$_2$ and R$_3$ are H. In another embodiment, R$_1$, R$_2$ is attached to R$_2$, R$_1$ on the other side of Formula (I) respectively, via OPEGO; and R$_0$ and R$_3$ are H. In a further embodiment, R$_0$, R$_2$ is attached to R$_2$, R$_0$ on the other side of Formula (I) respectively, via OPEGO; and R$_1$ and R$_3$ are H. In another embodiment, R$_0$, R$_3$ is attached to R$_3$, R$_0$ on the other side of Formula (I) respectively, via OPEGO; and R$_1$ and R$_2$ are H. In yet a further embodiment, $R_1$, $R_3$ is attached to $R_3$, $R_1$ on the other side of Formula (I) respectively, via OPEGO; and $R_0$ and $R_2$ are H. In one embodiment, $R_2$, $R_3$ is attached to $R_3$, $R_2$ on the other side of Formula (I) respectively, via OPEGO; and $R_0$ and $R_1$ are H. In some embodiments, are the compounds 42a-42o. In other embodiments the PEG group is substituted with the PPG group.

In one embodiment is an ionophore or complex comprising Formula (I) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (I) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (I) forms a 1:1 complex, a 2:1 complex, or a 3:1 complex wherein the Zn cation is replaced with Cu or Au cation. In one embodiment, the compound of Formula (I) forms a 1:1 complex, a 2:1 complex, or a 3:1 complex wherein the Zn cation is replaced with Cu cation.

In one aspect is a pharmaceutical composition comprising the compound of Formula (I) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (I) further comprises a cyclodextrin.

In one embodiment is a zinc ionophore or zinc complex having a structure of Formula (Ia), wherein the structure of Formula (Ia) is an atropisomer of the structure of Formula (I). In another embodiment, is a zinc ionophore or zinc complex having the structure of Formula (Ia):

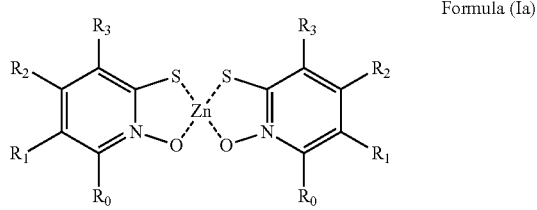

Formula (Ia)

wherein:

each $R_0$, each $R_1$, each $R_2$, and each $R_3$ on each side of Formula (Ia) is independently H, OH, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-; provided that at least one of the $R_0$, $R_1$, $R_2$, or $R_3$ groups is $L_1X_nL_2$-;

each $L_1$ is independently H, OH, $NH_2$, halogen, —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20; and each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

optionally, one of $R_0$, $R_1$, $R_2$, or $R_3$ on one side of Formula (Ia) may be attached by L to one of $R_0$, $R_1$, $R_2$, or $R_3$ on the other side of Formula (Ia);

L is selected from the group consisting of alkylene, substituted alkylene, alkenylene, substituted alkenylene, alkynylene, substituted alkynylene, —O—, —O—(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

For zinc ionophores or zinc complexes having a structure of Formula (Ia), in some embodiments described herein, each of $R_0$, $R_1$, $R_2$, and $R_3$ is independently the same on each side of Formula (Ia), lower alkyl, $(CH_2)_v$—$OR_y$, $OR_y$, $NHR_y$, $C(O)NHR_y$, wherein $R_y$ is PEG or PPG; wherein PEG or PPG is —(O-alkylene or O-substituted alkylene)$_x$—O—$R_z$ or -(alkylene-O or substituted alkylene-O)$_x$—$R_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, $R_1$ is CH$_2$—OPEG; and $R_0$, $R_2$, and $R_3$ are H. In some embodiments, $R_3$ is OPEG; and $R_0$, $R_1$, and $R_2$ are H. In some embodiments, $R_2$ is OPEG; and $R_0$, $R_1$, and $R_3$ are H. In some embodiments, $R_2$ and $R_3$ are OPEG; and $R_0$ and $R_1$ are H. In some embodiments, $R_2$ is NHPEG; and $R_0$, $R_1$, and $R_3$ are H. In some embodiments, $R_1$ is OPEG; and $R_0$, $R_2$, and $R_3$ are H. In some embodiments, $R_1$ is CH$_2$—OPPG; and $R_0$, $R_2$, and $R_3$ are H. In some embodiments, $R_3$ is OPPG; and $R_0$, $R_1$, and $R_2$ are H. In some embodiments, $R_2$ is OPPG; and $R_0$, $R_1$, and $R_3$ are H. In some embodiments, $R_2$ and $R_3$ are OPPG; and $R_0$ and $R_1$ are H. In some embodiments, $R_2$ is NHPPG; and $R_0$, $R_1$, and $R_3$ are H. In some embodiments, $R_1$ is OPPG; and $R_0$, $R_2$, and $R_3$ are H. In one embodiment, $R_1$, $R_2$, and $R_3$ are H; and $R_0$ is OPEG-(C$_6$H$_5$). In another embodiment, $R_1$, $R_2$, and $R_3$ are H; and $R_0$ is OPPG-(C$_6$H$_5$).

For zinc ionophores or zinc complexes having a structure of Formula (Ia), in some embodiments described herein, each of $R_0$, $R_1$, $R_2$, and $R_3$ is independently the same on each side of Formula (Ia), or an optionally substituted group selected from a mono-hydroxylated group, a dihydroxylated group, a tri-hydroxylated group, a tetra-hydroxylated group, a penta-hydroxylated group, or a saccharide.

For zinc ionophores or zinc complexes having a structure of Formula (Ia), in some embodiments described herein, each of $R_0$, $R_1$, $R_2$, and $R_3$ is independently the same on each side of Formula (Ia), L, wherein L is PEG or PPG; wherein PEG or PPG is —(O-alkylene or O-substituted alkylene)$_x$—O—$R_z$ or -(alkylene-O or substituted alkylene-O)$_x$$R_z$, where $R_z$ is H, alkyl, $R_0$, $R_1$, $R_2$, or $R_3$; and x is 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OR$_z$ or —(CH$_2$CH$_2$O)$_x$R$_z$. In some embodiments, PPG is —(OCH$_2$CH$_2$CH$_2$)$_x$OR$_z$; —(CH$_2$CH$_2$CH$_2$O)$_x$R$_z$; —(OCH(CH$_3$)CH$_2$)$_x$OR$_z$; —(CH(CH$_3$)CH$_2$)$_x$R$_z$; —(OCH$_2$CH(CH$_3$))$_x$OR$_z$; or —(OCH$_2$CH(CH$_3$))$_x$R$_z$. In some embodiments, one $R_0$ is attached to another $R_0$ on the other side of Formula (Ia) via OPEGO; and $R_1$, $R_2$, and $R_3$ are H. In some embodiments, one $R_1$ is attached to another $R_1$ on the other side of Formula (Ia) via OPEGO; and $R_0$, $R_2$, and $R_3$ are H. In some embodiments, $R_2$ is attached to another $R_2$ on the other side of Formula (Ia) via OPEGO; and $R_0$, $R_1$, and $R_3$ are H. In some embodiments, one $R_2$ is attached to one $R_3$ on the other side of Formula (Ia) via OPEGO; and $R_0$ and $R_1$ and the other $R_2$ and $R_3$ are H. In some embodiments, one $R_1$ is attached to one $R_3$ on the other side of Formula (Ia) via OPEGO; and $R_0$ and $R_2$ and the other $R_1$ and $R_3$ are H. In some embodiments, one $R_0$ is attached to one $R_3$ on the other side of Formula (Ia) via OPEGO; and $R_2$ and $R_1$ and the other $R_0$ and $R_3$ are H. In some embodiments, one $R_0$ is attached to one $R_1$ on the other side of Formula (Ia) via OPEGO; and $R_2$ and $R_3$ and the other $R_0$ and $R_1$ are H. In some embodiments, one $R_1$ is attached to one $R_2$ on the other side of Formula (Ia) via OPEGO; and $R_0$ and $R_3$ and the other $R_1$ and $R_2$ are H. In some embodiments, one $R_0$ is attached to one $R_2$ on the other side of Formula (Ia) via OPEGO; and $R_1$ and $R_3$ and the other $R_0$ and $R_2$ are H. In other embodiments the PEG group is substituted with the PPG group. In another embodiment, $R_1$, $R_2$, and $R_3$ are H; and $R_D$ is OPPG-(C$_6$H$_5$). In one embodiment is a zinc ionophore or zinc complex of the atropisomer of compound 50a-50c. In some embodiments, $R_1$ is C(O)NHR$_y$, $R_0$, $R_2$, and $R_3$ are H. In another embodiment is a zinc ionophore or zinc complex of the atropisomer of compound 17.

For zinc ionophores or zinc complexes having a structure of Formula (Ia), in some embodiments described herein, each of $R_0$, $R_1$, $R_2$, and $R_3$ is independently H, or an optionally substituted group selected from a mono-hydroxylated group, a dihydroxylated group, a tri-hydroxylated group, a tetra-hydroxylated group, a penta-hydroxylated group, or a saccharide.

In one embodiment is an ionophore or complex comprising Formula (Ia) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (Ia) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (Ia) forms a 1:1 complex, a 2:1 complex, or a 3:1 complex wherein the Zn cation is replaced with Cu or Au cation. In one embodiment, the compound of Formula (Ia) forms a 1:1 complex, a 2:1 complex, or a 3:1 complex wherein the Zn cation is replaced with Cu cation.

In one aspect is a pharmaceutical composition comprising the compound of Formula (Ia) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (Ia) further comprises a cyclodextrin.

In one aspect is a zinc chelator having the structure of Formula (Ib):

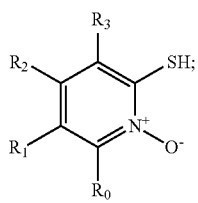

Formula (Ib)

wherein:

each $R_0$, each $R_1$, each $R_2$, and each $R_3$ is independently H, OH, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-; provided that at least one of the $R_0$, $R_1$, $R_2$, or $R_3$ groups is $L_1X_nL_2$-;

each $L_1$ is independently H, OH, $NH_2$, halogen, —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20; and each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$—where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON (R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

For zinc ionophores or zinc complexes having a structure of Formula (Ib), in some embodiments described herein, each of $R_0$, $R_1$, $R_2$, and $R_3$ is independently H, provided that at least one of $R_0$, $R_1$, $R_2$, or $R_3$ is not H, lower alkyl, $(CH_2)_v$—$OR_y$, $OR_y$, $NHR_y$, C(O)$NHR_y$, wherein $R_y$ is PEG or PPG; wherein PEG or PPG is —(O-alkylene or O-substituted alkylene)$_x$—O—$R_z$ or -(alkylene-O or substituted alkylene-O)$_x$—$R_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, $R_1$ is CH$_2$—OPEG; and $R_0$, $R_2$, and $R_3$ are H. In some embodiments, $R_3$ is OPEG; and $R_0$, $R_1$, and $R_2$ are H. In some embodiments, $R_2$ is OPEG; and $R_0$, $R_1$, and $R_3$ are H. In some embodiments, $R_2$ and $R_3$ are OPEG; and $R_0$ and $R_1$ are H. In some embodiments, $R_2$ is NHPEG; and $R_0$, $R_1$, and $R_3$ are H. In some embodiments, $R_1$ is OPEG; and $R_0$, $R_2$, and $R_3$ are H. In some embodiments, $R_1$ is CH$_2$—OPPG; and $R_0$, $R_2$, and $R_3$ are H. In some embodiments, $R_3$ is OPPG; and $R_0$, $R_1$, and $R_2$ are H. In some embodiments, $R_2$ is OPPG; and $R_0$, $R_1$, and $R_3$ are H. In some embodiments, $R_2$ and $R_3$ are OPPG; and $R_0$ and $R_1$ are H. In some embodiments, $R_2$ is NHPPG; and $R_0$, $R_1$, and $R_3$ are H. In some embodiments, $R_1$ is OPPG; and $R_0$, $R_2$, and $R_3$ are H. In one embodiment, $R_1$, $R_2$, and $R_3$ are H; and $R_0$ is OPEG-($C_6H_5$). In another embodiment, $R_1$, $R_2$, and $R_3$ are H; and $R_0$ is OPPG—($C_6H_5$).

For zinc ionophores or zinc complexes having a structure of Formula (Ib), in some embodiments described herein, each of $R_0$, $R_1$, $R_2$, and $R_3$ is independently the same on each side of Formula (Ib), or an optionally substituted group selected from a mono-hydroxylated group, a dihydroxylated group, a tri-hydroxylated group, a tetra-hydroxylated group, a penta-hydroxylated group, or a saccharide.

In one aspect is a pharmaceutical composition comprising the compound of Formula (Ib) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (Ib) further comprises a cyclodextrin.

In one embodiment, the compound of Formula (Ib) forms a 1:1 complex, a 2:1 complex, or a 3:1 complex with a transition metal cation. In some embodiments, the transition metal cation is selected from the cation of transition metals, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, and Uub. In one embodiment the compound of Formula (Ib) forms a 1:1 complex, a 2:1 complex, or a 3:1 complex with Cu or Au cation. In one embodiment, the compound of Formula (Ib) forms a 1:1 complex, a 2:1 complex, or a 3:1 complex with Cu cation.

An aspect described herein relates to novel zinc ionophores or zinc complexes, comprising Formula (II):

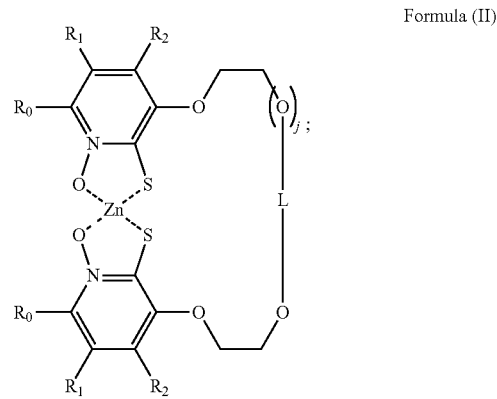

Formula (II)

wherein:

each $R_0$, each $R_1$, and each $R_2$, on each side of Formula (II) is independently H, OH, —O—, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-;

each $L_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20;

j is 0 or 1;

each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independent H, alkyl, or substituted alkyl; and L is selected from the group consisting of a bond, alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)$_m$-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; m is an integral number selected from 1 to 20; and pharmaceutically acceptable salts, pharmaceutically acceptable atropisomers, pharmaceutically active metabolites, pharmaceutically acceptable prodrugs, and pharmaceutically acceptable solvates.

For zinc ionophores or zinc complexes having a structure of Formula (II), in some embodiments, each of $R_0$, $R_1$, and $R_2$ is independently H, lower alkyl, or substituted lower alkyl; and L is selected from the group consisting of alkylene, substituted alkylene, —O—, —O-(alkylene or substituted alkylene)-, -(alkylene or substituted alkylene)-O-(alkylene or substituted alkylene)$_m$-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, and -(alkylene or substituted alkylene)-O-(alkylene or substituted alkylene)-S—S-(alkylene or substituted alkylene)-O-(alkylene or substituted alkylene. In some embodiments, $R_0$, $R_1$, and $R_2$ are H.

For zinc ionophores or zinc complexes having a structure of Formula (II), in some embodiments described herein, at least one of $R_0$, $R_1$, and $R_2$ is an optionally substituted group selected from a mono-hydroxylated group, a dihydroxylated group, a tri-hydroxylated group, a tetra-hydroxylated group, a penta-hydroxylated group, or a saccharide.

For zinc ionophores or zinc complexes having a structure of Formula (II), in some embodiments described herein, each of $R_0$, $R_1$, and $R_2$, is independently H, lower alkyl, $(CH_2)_v$—$OR_y$, $OR_y$, $NHR_y$, $C(O)NHR_y$, wherein $R_y$ is PEG or PPG; wherein PEG or PPG is —(O-alkylene or O-substituted alkylene)$_x$-O—$R_z$ or -(alkylene-O or substituted alkylene-O)$_x$—$R_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, $R_1$ is CH$_2$—OPEG; and $R_0$, and $R_2$ are H. In some embodiments, $R_2$ is OPEG; and $R_0$, and $R_1$, are H. In some embodiments, $R_2$ is NHPEG; and $R_0$, and $R_1$ are H. In some embodiments, $R_1$ is OPEG; and $R_0$, and $R_2$, are H. In some embodiments, $R_1$ is $CH_2$—OPPG; and $R_D$, and $R_2$ are H. In some embodiments, $R_2$ is OPPG; and $R_0$, $R_1$, and $R_3$ are H. In some embodiments, $R_2$ is NHPPG; and $R_0$, and $R_1$ are H. In some embodiments, $R_1$ is OPPG; and $R_0$, and $R_2$ are H. In one embodiment, $R_1$, and $R_2$ are H; and $R_0$ is OPEG-$(C_6H_5)$. In another embodiment, $R_1$, and $R_2$ are H; and $R_0$ is OPPG-$(C_6H_5)$.

In one aspect is a pharmaceutical composition comprising the compound of Formula (II) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (II) further comprises a cyclodextrin.

In one embodiment is an ionophore or complex comprising Formula (II) wherein the Zn is replaced by another transition metal cation, such as by way of example only, cations of Sc, Ti, V, Cr, Mn, Fe, Co, Ni, Cu, Zn, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (II) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (II) forms a 1:1 complex, a 2:1 complex, or a 3:1 complex wherein the Zn cation is replaced with Cu or Au cation. In one embodiment, the compound of Formula (II) forms a 1:1 complex, a 2:1 complex, or a 3:1 complex wherein the Zn cation is replaced with Cu cation.

In some embodiments of zinc ionophores or zinc complexes having a structure of Formula (II), L is selected from the group consisting of —S—S—,

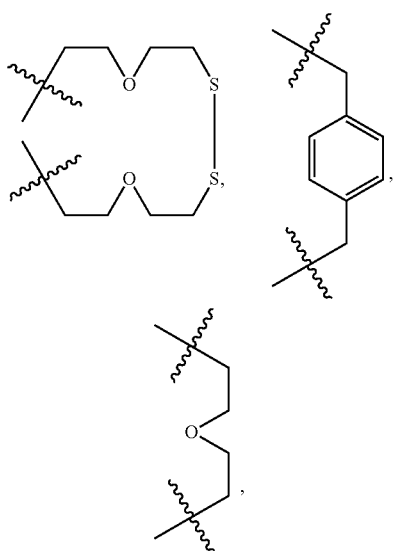

$CH_2CH_2$, —$(CH_2CH_2O)_2CH_2CH_2$—, and —$(CH_2CH_2O)_4CH_2CH_2$—. In one embodiment is the compound of Formula (II) wherein j is 0; L is a bond; and $R_0$, $R_1$, and $R_2$ are H. In another embodiment is the compound of Formula (II)

wherein L is $(CH_2OCH_2)_m$,; m is an integral number from 0-4; j is 1, and $R_0$, $R_1$, and $R_2$ are H.

For zinc ionophores or zinc complexes having a structure of Formula (II), in some embodiments described herein, each of $R_0$, $R_1$, and $R_2$, is independently H, or an optionally substituted group selected from a mono-hydroxylated group, a dihydroxylated group, a tri-hydroxylated group, a tetra-hydroxylated group, a penta-hydroxylated group, or a saccharide.

In another embodiment, is a zinc ionophore or zinc complex having the structure of Formula (IIa):

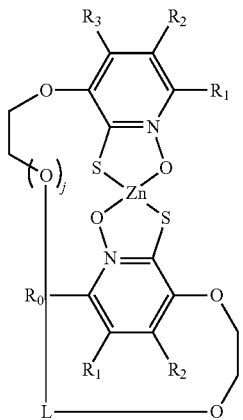

Formula (IIa)

wherein:

$R_0$, $R_1$, and $R_2$, on one side of Formula (IIa) and $R_1$, $R_2$, and $R_3$, on the other side of Formula (IIa) is independently H, OH, —O—, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —$S(O)_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or $L_1X_nL_2$-; provided that at least one of the $R_0$, $R_1$, $R_2$ or $R_3$, groups is $L_1X_nL_2$-;

each $L_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —$S(O)_k$ (alkylene or substituted alkylene)-, where k is 1, 2, or 3;

each n is an integral number selected from 1 to 20;

j is 0 or 1;

each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R)C(S)N(R')—, —N(R')S(O)$_k$N(R')—, and —C(R')$_2$—N(R')—N(R')—; where each R' is independently H, alkyl, or substituted alkyl; and L is selected from the group consisting of a bond, alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)$_m$-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; m is an integral number selected from 1 to 20; and pharmaceutically acceptable salts, pharmaceutically acceptable atropisomers, pharmaceutically active metabolites, pharmaceutically acceptable prodrugs, and pharmaceutically acceptable solvates.

For zinc ionophores or zinc complexes having a structure of Formula (IIa), in some embodiments, $R_0$, $R_1$, and $R_2$, on one side of Formula (IIa) and $R_1$, $R_2$, and $R_3$, on the other side of Formula (IIa) is independently H, lower alkyl, or substituted lower alkyl; and L is selected from the group consisting of alkylene, substituted alkylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, and -(alkylene or substituted alkylene)-O-(alkylene or substituted alkylene)-S—S-(alkylene or substituted alkylene)-O-(alkylene or substituted alkylene. In some embodiments, $R_0$, $R_1$, $R_2$, and $R_3$ are H.

For zinc ionophores or zinc complexes having a structure of Formula (IIa), in some embodiments described herein, at least one of $R_0$, $R_1$, $R_2$, and $R_3$ is an optionally substituted group selected from a mono-hydroxylated group, a dihydroxylated group, a tri-hydroxylated group, a tetra-hydroxylated group, a penta-hydroxylated group, or a saccharide.

For zinc ionophores or zinc complexes having a structure of Formula (IIa), in some embodiments described herein, each of $R_0$, $R_1$, and $R_2$, on one side of Formula (IIa) and $R_1$, $R_2$, and $R_3$ on the other side of Formula (IIa) is independently H, lower alkyl, $(CH_2)_v$—$OR_y$, $OR_y$, $NHR_y$, $C(O)NHR_y$, wherein $R_y$ is PEG or PPG; wherein PEG or PPG is —(O-alkylene or O-substituted alkylene)$_x$-O—$R_z$ or -(alkylene-O or substituted alkylene-O)$_x$—$R_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, $R_1$ is CH$_2$—OPEG; and $R_0$, $R_2$, and $R_3$ are H. In some embodiments, $R_2$ is OPEG; and $R_0$, $R_1$, and $R_3$ are H. In some embodiments, $R_2$ is NHPEG; and $R_0$, $R_1$, and $R_3$ are H. In some embodiments, $R_1$ is OPEG; and $R_0$, $R_2$, and $R_3$ are H. In some embodiments, $R_1$ is CH$_2$—OPPG; and $R_0$, $R_2$, and $R_3$ are H. In some embodiments, $R_2$ is OPPG; and $R_0$, $R_1$, and $R_3$ are H. In some embodiments, $R_2$ is NHPPG; and $R_0$, $R_1$, and $R_3$ are H. In some embodiments, $R_1$ is OPPG; and $R_0$, $R_2$, and $R_3$ are H. In one embodiment, $R_1$, $R_2$, and $R_3$ are H; and $R_0$ is OPEG-(C$_6$H$_5$). In another embodiment, $R_1$, $R_2$, and $R_3$ are H; and $R_0$ is OPPG-(C$_6$H$_5$).

In one aspect is a pharmaceutical composition comprising the compound of Formula (IIa) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (IIa) further comprises a cyclodextrin.

In one embodiment is a zinc chelator of Formula (II) wherein the metal cation, such as by way of example only, Zn is not bound to the compound of Formula (II). In another embodiment is a zinc chelator of Formula (IIa) wherein the metal cation, such as by way of example only, Zn is not bound to the compound of Formula (IIa).

In one aspect is a pharmaceutical composition comprising the compound of Formula (II) wherein the metal cation, such as by way of example only, Zn is not bound to the compound of Formula (II) and a pharmaceutically acceptable excipient, amino acid excipient, detergent, micelle, and dendrimer. In one embodiment, the pharmaceutical composition comprising the compound of Formula (II) wherein the metal cation, such as by way of example only, Zn is not bound to the compound of Formula (II) further comprises a cyclodextrin.

In another aspect is a pharmaceutical composition comprising the compound of Formula (IIa) wherein the metal cation, such as by way of example only, Zn is not bound to the compound of Formula (IIa) and a pharmaceutically acceptable excipient, amino acid excipient, detergent, micelle, and dendrimer. In one embodiment, the pharmaceutical composition comprising the compound of Formula (IIa) wherein the metal cation, such as by way of example only, Zn is not bound to the compound of Formula (IIa) further comprises a cyclodextrin.

In one embodiment is an ionophore or complex comprising Formula (IIa) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (IIa) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (IIa) forms a 1:1 complex, a 2:1 complex, or a 3:1 complex wherein the Zn cation is replaced with Cu or Au cation. In one embodiment, the compound of Formula (IIa) forms a 1:1 complex, a 2:1 complex, or a 3:1 complex wherein the Zn cation is replaced with Cu cation.

An aspect described herein relates to novel zinc ionophores or zinc complexes, comprising Formula (III):

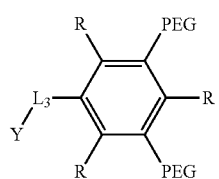

Formula (III)

wherein:

wherein PEG is —(O-alkylene or O-substituted alkylene)$_x$-O—R$_z$ or -(alkylene-O or substituted alkylene-O)$_x$—R$_z$, where R$_z$ is H or alkyl; and x is 1, 2, 3, 4, 5, 6, 7, 8, 9, 10, 11, 12, 13, 14, 15, 16, 17, 18, 19, or 20;

each R is independently H, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, or substituted aralkyl;

L$_3$ is selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

Y is selected from the group consisting of

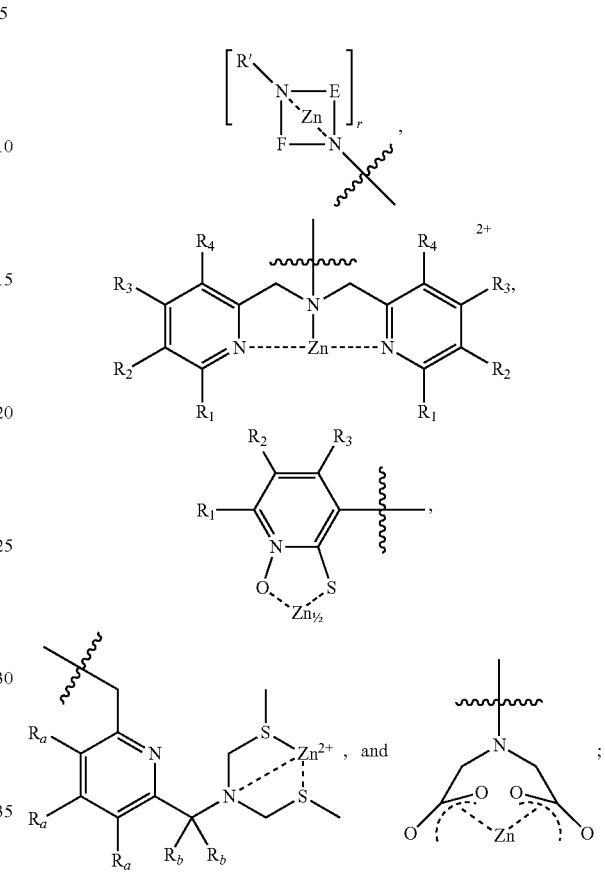

each of R' and R$_b$ is independently H, OH, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, or ester group;

each R$_0$, each R$_1$, each R$_2$, each R$_3$, each R$_4$, and each R$_a$ is independently H, OH, NH$_2$, NO$_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl; or L$_1$X$_a$L$_2$-; provided that at least one of the R$_0$, R$_1$, R$_2$, or R$_3$ groups is L$_1$X$_n$L$_2$-;

each L$_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$-(alkylene or substituted alkylene)-, where k is 1, 2, or 3;

each n is an integral number selected from 1 to 20;
E is ((CH$_2$)$_2$)$_p$ or C(O);
F is ((CH$_2$)$_2$)$_q$ or C(O);
p is an integral number selected from 1 to 4;
q is an integral number selected from 1 to 4;
r is an integral number selected from 1 to 5;
each L$_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

For zinc ionophores or zinc complexes having a structure of Formula (III), in some embodiments, each of R' and R$_b$ is independently H, CH$_3$, CH$_2$CH$_3$, CH$_2$C(O)OCH$_2$CH$_3$. In some embodiments PEG is substituted with PPG. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, each of R$_1$, R$_2$, R$_3$, R$_4$, and R$_a$ is H, CH$_3$, CH$_2$CH$_3$, (CH$_2$)$_v$—OR$_y$, OR$_y$, NHR$_y$, C(O)NHR$_y$, wherein R$_y$ is PEG or PPG; wherein PEG or PPG is —(O-alkylene or O-substituted alkylene)$_x$—O—R$_z$ or -(alkylene-O or substituted alkylene-O)$_x$—R$_z$, where R$_z$ is H or alkyl; v and x are independently 1, 2, 3, 4, 5, 6, 7, 8, 9, 10, 11, 12, 13, 14, 15, 16, 17, 18, 19, or 20. In some embodiments, R' is H. In some embodiments, R' is CH$_3$. In some embodiments, R' is CH$_2$CH$_3$. In some embodiments, R' is CH$_2$C(O)OCH$_2$CH$_3$.

When each of R$_1$, R$_2$, R$_3$, R$_4$, and R$_a$ is independently H, CH$_3$, CH$_2$CH$_3$, (CH$_2$)$_v$—OR$_y$, OR$_y$, NHR$_y$, C(O)NHR$_y$, in some embodiments, R$_1$, R$_3$, and/or R$_4$ are H. In some embodiments, R$_2$ is also H. In some embodiments, R$_2$ is CH$_3$. In some embodiments, R$_2$ is CH$_2$CH$_3$. In some embodiments, R$_2$ is OPEG. In other embodiments, R$_2$ is OPPG. In some embodiments, R$_a$ is H. In some embodiments, at least one of R$_1$, R$_2$, R$_3$, R$_4$, and R$_a$ is selected from (CH$_2$)$_y$—OR$_y$, OR$_y$, NHR$_y$, C(O)NHR$_y$. For zinc ionophores or zinc complexes having a structure of Formula (III), in some embodiments described herein, at least one of R$_1$, R$_2$, R$_3$, R$_4$, and R$_a$ is an optionally substituted group selected from a mono-hydroxylated group, a dihydroxylated group, a tri-hydroxylated group, a tetra-hydroxylated group, a penta-hydroxylated group, or a saccharide.

In another embodiment, is a zinc ionophore or zinc complex comprising the structure of Formula (III):

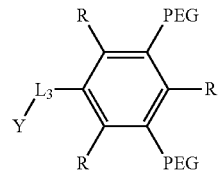

Formula (III)

wherein:
wherein PEG is —(O-alkylene or O-substituted alkylene)$_x$-O—R$_z$ or -(alkylene-O or substituted alkylene-O)$_x$—R$_z$, where R$_z$ is H or alkyl and x is 1, 2, 3, 4, 5, 6, 7, 8, 9, 10, 11, 12, 13, 14, 15, 16, 17, 18, 19, or 20;

each R is independently H, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, or substituted aralkyl;

L$_3$ is selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and 13 C(R')$_2$—N(R')—N(R')—; where each R' is independently H, alkyl, or substituted alkyl;

Y is

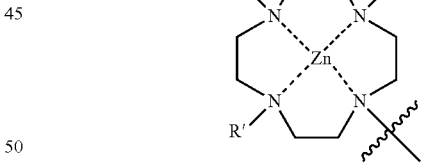

each R' is independently H, OH, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, or ester group; and pharmaceutically acceptable salts, pharmaceutically active metabolites, pharmaceutically acceptable prodrugs, and pharmaceutically acceptable solvates. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In other embodiments, PEG is —(OCH$_2$CH$_2$)$_x$OR$_z$ or —(CH$_2$CH$_2$O)$_x$R$_z$. In some embodiments, PEG is substituted with PPG. In some embodiments, PPG is —(OCH$_2$CH$_2$CH$_2$)$_x$OR$_z$; —(CH$_2$CH$_2$CH$_2$O)$_x$R$_z$; —(OCH(CH$_3$)CH$_2$)$_x$OR$_z$; —(CH(CH$_3$)CH$_2$)$_x$R$_z$; —(OCH$_2$CH(CH$_3$))$_x$OR$_z$; or —(OCH$_2$CH(CH$_3$))$_x$R$_z$.

In one aspect is a pharmaceutical composition comprising the compound of Formula (III) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (III) further comprises a cyclodextrin.

In one embodiment is a zinc chelator of Formula (III) wherein the metal cation, such as by way of example only, Zn is not bound to the compound of Formula (III). In another embodiment is a zinc chelator of Formula (III) wherein the metal cation, such as by way of example only, Zn is not bound to the compound of Formula (III).

In one aspect is a pharmaceutical composition comprising the compound of Formula (III) wherein the metal cation, such as by way of example only, Zn is not bound to the compound of Formula (III) and a pharmaceutically acceptable excipient, amino acid excipient, detergent, micelle, and dendrimer. In one embodiment, the pharmaceutical composition comprising the compound of Formula (III) wherein the metal cation, such as by way of example only, Zn is not bound to the compound of Formula (III) further comprises a cyclodextrin.

In one embodiment is an ionophore or complex comprising Formula (III) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (III) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (III) forms a 1:1 complex, a 2:1 complex, or a 3:1 complex wherein the Zn cation is replaced with Cu or Au cation. In one embodiment, the compound of Formula (III) forms a 1:1 complex, a 2:1 complex, or a 3:1 complex wherein the Zn cation is replaced with Cu cation.

Another aspect described herein relates to compounds having the structure of Formula (IV) thereof:

Formula (IV)

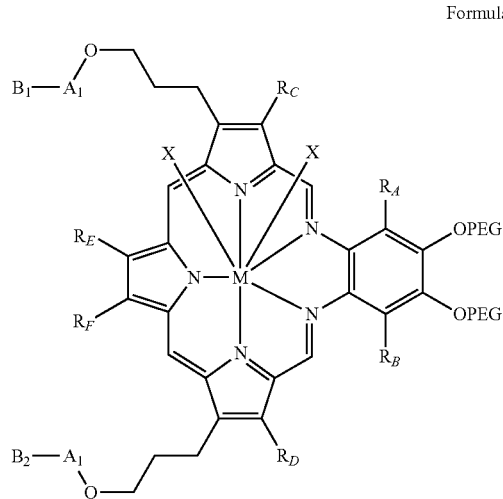

wherein:
M is a trivalent lanthanide metal cation;
each X is independently selected from the group consisting of $OH^-$, $AcO^-$, $Cl^-$, $Br^-$, $I^-$, $F^-$, $H_2PO_4^-$, $ClO^-$, $ClO_2^-$, $ClO_3^-$, $ClO_4^-$, $HCO_3^-$, $HSO_4^{4-}$, $NO_3^-$, $N_3^-$, $CN^-$, $SCN^-$, and $OCN^-$;
each of $R_A$ and $R_B$ is independently H or $C_1$-$C_6$ alkyl;
each of $R_C$, $R_D$, $R_E$, and $R_F$ is independently H, OH, $C_iH_{(2i+1)}O_y$, or $OC_iH_{(2i+1)}O_y$;
i is an integer number from 1 to 11;
y is zero or an integer number less than or equal to i.
each of $A_1$ and $A_2$ is optional, and when present is a linker independently selected from the group consisting of alkylene, substituted alkylene, —NHC(O)CH$_2$—, —OC(O)CH$_2$—, —SSCH$_2$CH$_2$OC(O)CH$_2$—, —SSCH$_2$CH$_2$NHC(O)CH$_2$—, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—;
where each R' is independently H, alkyl, or substituted alkyl;
each of $B_1$ and $B_2$ is independently selected from the group consisting of H, OH, PEG,

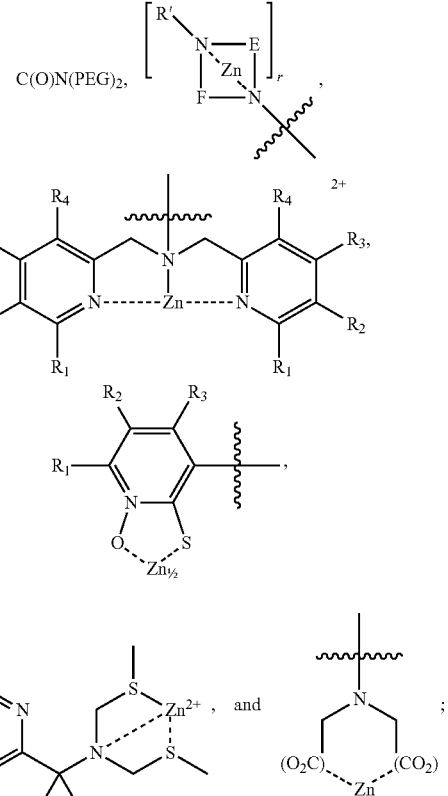

each of R' and $R_b$ is independently H, OH, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, or ester group;

each of $R_1$, $R_2$, $R_3$, $R_4$, and $R_a$ is independently H, OH, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, or $L_1(X)_nL_2$-;

each $L_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20;
E is ((CH$_2$)$_p$ or C(O);
F is ((CH$_2$)$_q$ or C(O);
p is an integral number selected from 1 to 4;
q is an integral number selected from 1 to 4;
r is an integral number selected from 1 to 5;

each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically acceptable atropisomers, pharmaceutically active metabolites, pharmaceutically acceptable prodrugs, and pharmaceutically acceptable solvates.

For compounds having a structure of Formula (IV), in some embodiments, M is a trivalent lanthanide metal cation selected from the group consisting of $La^{+3}$, $Ce^{+3}$, $Pr^{+3}$, $Nd^{+3}$, $Pm^{+3}$, $Sm^{+3}$, $Eu^{+3}$, $Gd^{+3}$, $Tb^{+3}$, $Dy^{+3}$, $Ho^{+3}$, $Er^{+3}$, $Tm^{+3}$, $Yb^{+3}$, and $Lu^{+3}$. In some embodiments, M is a trivalent lanthanide metal cation selected from the group $Sm^{+3}$, $Eu^{+3}$, $Gd^{+3}$, $Tb^{+3}$, $Dy^{+3}$, and $HO^{+3}$. In some embodiments, each of $A_1$ and $A_2$ is a linker selected from the group consisting of —NHC(O)CH$_2$—, —OC(O)CH$_2$—, —SSCH$_2$CH$_2$OC(O)CH$_2$—, and —SSCH$_2$CH$_2$NHC(O)CH$_2$—. In some embodiments, each of R' and $R_b$ is independently H, CH$_3$, CH$_2$CH$_3$, CH$_2$C(O)OCH$_2$CH$_3$. In some embodiments, each of $R_1$, $R_2$, $R_3$, $R_4$, and $R_a$ is H, CH$_3$, CH$_2$CH$_3$, (CH$_2$)$_v$—OR$_y$, OR$_y$, NHR$_y$, C(O)NHR$_y$, wherein $R_y$ is PEG or PPG; wherein PEG or PPG is —(O-alkylene or O-substituted alkylene)$_x$-O—R$_z$ or -(alkylene-O or substituted alkylene-O)$_x$—R$_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, R' is H. In some embodiments, R' is CH$_3$. In some embodiments, R' is CH$_2$CH$_3$. In some embodiments, R' is CH$_2$C(O)OCH$_2$CH$_3$. In some embodiments, $R_2$ is selected from the group consisting of H, OH, PEG, C(O)N(PEG)$_2$. In some embodiments PEG is substituted with PPG. In other embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H.

When each of $R_1$, $R_2$, $R_3$, $R_4$, and $R_a$ is independently H, CH$_3$, CH$_2$CH$_3$, CH$_2$—OPEG, OPEG, NHPEG, C(O)NHPEG, in some embodiments, $R_1$, $R_3$, and/or $R_4$ are H. In some embodiments, $R_2$ is also H. In some embodiments, $R_2$ is CH$_3$. In some embodiments, $R_2$ is CH$_2$CH$_3$. In some embodiments, $R_2$ is OPEG. In some embodiments, $R_a$ is H. In some embodiments, at least one of $R_1$, $R_2$, $R_3$, $R_4$, and $R_a$ is selected from CH$_2$—OPEG, OPEG, NHPEG, and C(O)NHPEG. For zinc ionophores, zinc chelators and/or zinc complexes having a structure of Formula (IV), in some embodiments described herein, at least one of $R_1$, $R_2$, $R_3$, $R_4$, and $R_a$ is an optionally substituted group selected from a mono-hydroxylated group, a dihydroxylated group, a tri-hydroxylated group, a tetra-hydroxylated group, a penta-hydroxylated group, or a saccharide. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H.

For zinc ionophores, zinc chelators and/or zinc complexes having a structure of Formula (IV), the number of X is not limited to 2 such that a person of ordinary skill in the art would appreciate that the X of Formula (IV) may be partially or completely dissociated, whereby the resulting texaphrin core bears an appropriate positive charge.

In one embodiment is the compound having the structure of Formula (IV) wherein $B_1$ or $B_2$ is

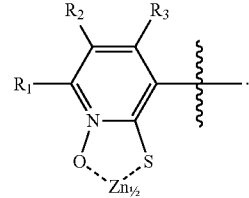

In another embodiment, is the compound having the structure of Formula (IV) wherein $B_1$ or $B_2$ is

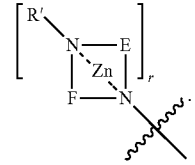

In yet another embodiment is the compound having the structure of Formula (IV) wherein $B_1$ or $B_2$ is

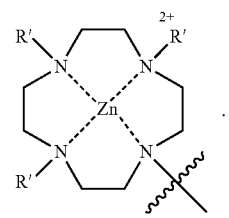

In one embodiment is a zinc chelator of Formula (IV) wherein the metal cation, such as by way of example only, Zn is not bound to the compound of Formula (IV).

In one aspect is a pharmaceutical composition comprising the compound of Formula (IV) wherein the metal cation, such as by way of example only, Zn is not bound to the compound of Formula (IV) and a pharmaceutically acceptable excipient, amino acid excipient, detergent, micelle, and dendrimer. In one embodiment, the pharmaceutical composition comprising the compound of Formula (IV) wherein the metal cation, such as by way of example only, Zn is not bound to the compound of Formula (IV) further comprises a cyclodextrin.

In another aspect is a pharmaceutical composition comprising the compound of Formula (IV) wherein the metal cation, such as by way of example only, Zn is not bound to the compound of Formula (IV) and a pharmaceutically acceptable excipient, amino acid excipient, detergent, micelle, and dendrimer. In one embodiment, the pharmaceutical composition comprising the compound of Formula (IV) wherein the metal cation, such as by way of example only, Zn is not bound to the compound of Formula (IV) further comprises a cyclodextrin.

In one embodiment is an ionophore or complex comprising Formula (IV) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (IV) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (IV) forms a 1:1 complex, a 2:1 complex, or a 3:1 complex wherein the Zn cation is replaced with Cu or Au cation. In one embodiment, the compound of Formula (IV) forms a 1:1 complex, a 2:1 complex, or a 3:1 complex wherein the Zn is replaced with Cu.

In one aspect is a compound having the structure of Formula (V):

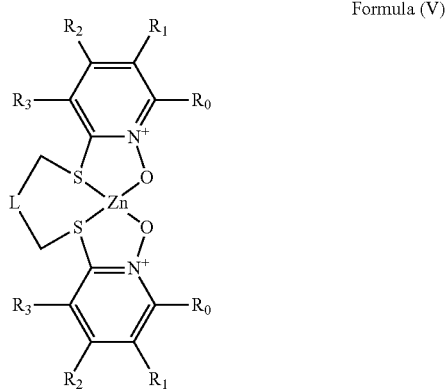

Formula (V)

wherein:
each of $R_0$, $R_1$, $R_2$, and $R_3$ is independently H, OH, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, or $L_1(X)_nL_2$-;

each $L_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20; and each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N (R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically active metabolites, pharmaceutically acceptable prodrugs, and pharmaceutically acceptable solvates.

For zinc ionophores or zinc complexes having a structure of Formula (V), in some embodiments described herein, each of $R_0$, $R_1$, $R_2$, and $R_3$ is independently H, lower alkyl, $(CH_2)_v$—$OR_y$, $OR_y$, $NHR_y$, $C(O)NHR_y$, wherein $R_y$ is PEG or PPG; wherein PEG or PPG is —(O-alkylene or O-substituted alkylene)$_x$-O—$R_z$ or -(alkylene-O or substituted alkylene-O)$_x$—$R_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$O)$_x$H; —(OCH(CH$_3$)CH$_2$)$_x$OH; —(CH(CH$_3$)CH$_2$)$_n$H; —(OCH$_2$CH(CH$_3$))$_x$OH; or —(OCH$_2$CH(CH$_3$))$_x$H. In some embodiments, $R_1$ is CH$_2$—OPEG; and $R_0$, $R_2$, and $R_3$ are H. In some embodiments, $R_3$ is OPEG; and $R_0$, $R_1$, and $R_2$ are H. In some embodiments, $R_2$ is OPEG; and $R_0$, $R_1$, and $R_3$ are H. In some embodiments, $R_2$ and $R_3$ are OPEG; and $R_0$ and $R_1$ are H. In some embodiments, $R_2$ is NHPEG; and $R_0$, $R_1$, and $R_3$ are H. In some embodiments, $R_1$ is OPEG; and $R_0$, $R_2$, and $R_3$ are H. In some embodiments, $R_1$ is CH$_2$—OPPG; and $R_0$, $R_2$, and $R_3$ are H. In some embodiments, $R_3$ is OPPG; and $R_0$, $R_1$, and $R_2$ are H. In some embodiments, $R_2$ is OPPG; and $R_0$, $R_1$, and $R_3$ are H. In some embodiments, $R_2$ and $R_3$ are OPPG; and $R_0$ and $R_1$ are H. In some embodiments, $R_2$ is NHPPG; and $R_0$, $R_1$, and $R_3$ are H. In some embodiments, $R_1$ is OPPG; and $R_0$, $R_2$, and $R_3$ are H. In one embodiment, $R_1$, $R_2$, and $R_3$ are H; and $R_0$ is OPEG—(C$_6$H$_5$). In another embodiment, $R_1$, $R_2$, and $R_3$ are H; and $R_0$ is OPPG-(C$_6$H$_5$).

For zinc ionophores or zinc complexes having a structure of Formula (V), in some embodiments described herein, each of $R_0$, $R_1$, $R_2$, and $R_3$ is independently H, or an optionally substituted group selected from a mono-hydroxylated group, a dihydroxylated group, a tri-hydroxylated group, a tetra-hydroxylated group, a penta-hydroxylated group, or a saccharide.

For zinc ionophores or zinc complexes having a structure of Formula (V), in some embodiments described herein, each of $R_0$, $R_1$, $R_2$, and $R_3$ is independently H, a bond, L, wherein L is PEG or PPG; wherein PEG or PPG is —(O-alkylene or O-substituted alkylene)$_x$-O—$R_z$ or -(alkylene-O or substituted alkylene-O)$_x$$R_z$, where $R_z$ is H, alkyl, $R_0$, $R_1$, $R_2$, or $R_3$; and x is 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OR$_z$ or —(CH$_2$CH$_2$O)$_x$R$_z$. In some embodiments, PPG is —(OCH$_2$CH$_2$CH$_2$)$_x$OR$_z$; —(CH$_2$CH$_2$CH$_2$O)$_x$R$_z$; —(OCH(CH$_3$)CH$_2$)$_x$OR$_z$; —(CH(CH$_3$)CH$_2$)$_x$R$_z$; —(OCH$_2$CH(CH$_3$))$_x$OR$_z$; or —(OCH$_2$CH(CH$_3$))$_x$R$_z$. In some embodiments, one $R_0$ is attached to another $R_0$ on the other side of Formula (V) via OPEGO; and $R_1$, $R_2$, and $R_3$ are H. In some embodiments, one $R_1$ is attached to another $R_1$ on the other side of Formula (V) via OPEGO; and $R_0$, $R_2$, and $R_3$ are H. In some embodiments, $R_2$ is attached to another $R_2$ on the other side of Formula (V) via OPEGO; and $R_0$, $R_1$, and $R_3$ are H. In some embodiments, one $R_2$ is attached to one $R_3$ on the other side of Formula (V) via OPEGO; and $R_0$ and $R_1$ and the other $R_2$ and $R_3$ are H. In some embodiments, one $R_1$ is attached to one $R_3$ on the other side of Formula (V) via OPEGO; and $R_0$ and $R_2$ and the other $R_1$ and $R_3$ are H. In some embodiments, one $R_0$ is attached to one $R_3$ on the other side of Formula (V) via OPEGO; and $R_2$ and $R_1$ and the other $R_0$ and $R_3$ are H. In some embodiments, one $R_0$ is attached to one $R_1$ on the other side of Formula (V) via OPEGO; and $R_2$ and $R_3$ and the other $R_0$ and $R_1$ are H. In some embodiments, one $R_1$ is attached to one $R_2$ on the other side of Formula (V) via OPEGO; and $R_0$ and $R_3$ and the other $R_1$ and $R_2$ are H. In some embodiments, one $R_0$ is attached to one $R_2$ on the other side of Formula (V) via OPEGO; and $R_1$ and $R_3$ and the other $R_0$ and $R_2$ are H. In other embodiments the PEG group is substituted with the PPG group.

For zinc ionophores or zinc complexes having a structure of Formula (V), in some embodiments described herein, each of $R_0$, $R_1$, $R_2$, and $R_3$ is independently H, or an optionally substituted group selected from a mono-hydroxylated group, a dihydroxylated group, a tri-hydroxylated group, a tetra-hydroxylated group, a penta-hydroxylated group, or a saccharide.

In one embodiment, is a zinc chelator of Formula (V) wherein L is O-(alkylene or substituted alkylene)-O—. In another embodiment, is a zinc chelator of Formula (V) wherein L is PEG or PPG. In one embodiment, is a zinc chelator of Formula (V) wherein L is OPEGO or OPPGO. In another embodiment, is a zinc chelator of Formula (V) wherein L is (CH$_2$)$_x$PEG(CH$_2$)$_x$ or (CH$_2$)$_x$PPG(CH$_2$)$_x$. In a further embodiment is a zinc chelator of Formula (V) wherein L is (CH$_2$)$_x$OPEG(CH$_2$)$_x$ or (CH$_2$)$_x$OPPG(CH$_2$), In one embodiment is a zinc chelator of Formula (V) wherein the metal cation, such as by way of example only, Zn is not bound to the compound of Formula (V).

In one aspect is a pharmaceutical composition comprising the compound of Formula (V) wherein the metal cation, such as by way of example only, Zn is not bound to the compound of Formula (V) and a pharmaceutically acceptable excipient, amino acid excipient, detergent, micelle, and dendrimer. In one embodiment, the pharmaceutical composition comprising the compound of Formula (V) wherein the metal cation, such as by way of example only, Zn is not bound to the compound of Formula (V) further comprises a cyclodextrin.

In another aspect is a pharmaceutical composition comprising the compound of Formula (V) wherein the metal cation, such as by way of example only, Zn is not bound to the compound of Formula (V) and a pharmaceutically acceptable excipient, amino acid excipient, detergent, micelle, and dendrimer. In one embodiment, the pharmaceutical composition comprising the compound of Formula (V) wherein the metal cation, such as by way of example only, Zn is not bound to the compound of Formula (V) further comprises a cyclodextrin.

In one embodiment is an ionophore or complex comprising Formula (V) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (V) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (V) forms a 1:1 complex, a 2:1 complex, or a 3:1 complex wherein the Zn cation is replaced with Cu or Au cation. In one embodiment, the compound of Formula (V) forms a 1:1 complex, a 2:1 complex, or a 3:1 complex wherein the Zn cation is replaced with Cu cation.

In one embodiment is a compound having the structure of Formula (Va):

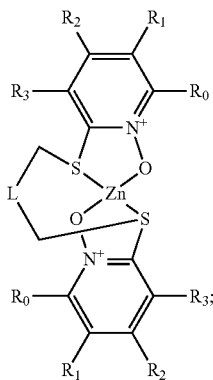

Formula (Va)

wherein:

each of $R_0$, $R_1$, and $R_2$ is independently H, OH, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, or $L_1(X)_nL_2$—;

each $L_1$ is independently H, OH, halogen, alkyl, substituted alkyl, alkenyl, alkoxy, substituted alkoxy, alkylalkoxy, substituted alkylalkoxy, polyalkylene oxide, a hydoxylated group, a substituted hydroxylated group, substituted polyalkylene oxide, aryl, substituted aryl, heteroaryl, substituted heteroaryl, alkaryl, substituted alkaryl, aralkyl, or substituted aralkyl;

each X is independently a hydroxylated group, a substituted hydroxylated group, —O-(alkylene or substituted alkylene)-, —S-(alkylene or substituted alkylene)-, or —S(O)$_k$(alkylene or substituted alkylene)-, where k is 1, 2, or 3;

each n is an integral number selected from 1 to 20; and each $L_2$ is independently selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R)-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts, pharmaceutically active metabolites, pharmaceutically acceptable prodrugs, and pharmaceutically acceptable solvates.

For zinc ionophores or zinc complexes having a structure of Formula (Va), in some embodiments described herein, each of $R_0$, $R_1$, $R_2$, and $R_3$ is independently H, lower alkyl, $(CH_2)_v$—$OR_y$, $OR_y$, $NHR_y$, $C(O)NHR_y$, wherein $R_y$ is PEG or PPG; wherein PEG or PPG is —(O-alkylene or O-substituted alkylene)$_x$-O—$R_z$ or -(alkylene-O or substituted alkylene-O)$_x$—$R_z$, where $R_z$ is H or alkyl; v and x are independently 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OCH$_3$ or —(CH$_2$CH$_2$O)$_x$CH$_3$. In other embodiments, PEG is —(OCH$_2$CH$_2$)$_x$OH or —(CH$_2$CH$_2$O)$_x$H. In some embodiments, PPG is —(OCH$_2$CH$_2$CH$_2$)$_x$OCH$_3$; —(CH$_2$CH$_2$CH$_2$O)$_x$CH$_3$; —(OCH(CH$_3$)CH$_2$)$_x$OCH$_3$; —(CH(CH$_3$)CH$_2$)$_x$CH$_3$; —(OCH$_2$CH(CH$_3$))$_x$OCH$_3$; or —(OCH$_2$CH(CH$_3$))$_x$CH$_3$. In other embodiments, PPG is —(OCH$_2$CH$_2$CH$_2$)$_x$OH, —(CH$_2$CH$_2$CH$_2$O)$_x$H; —(OCH(CH$_3$)CH$_2$)$_x$OH; —(CH(CH$_3$)CH$_2$)$_x$H; —(OCH$_2$CH(CH$_3$))$_x$OH; or —(OCH$_2$CH(CH$_3$))$_x$H. In some embodiments, $R_1$ is CH$_2$—OPEG; and $R_0$, $R_2$, and $R_3$ are H. In some embodiments, $R_3$ is OPEG; and $R_0$, $R_1$, and $R_2$ are H. In some embodiments, $R_2$ is OPEG; and $R_0$, $R_1$, and $R_3$ are H. In some embodiments, $R_2$ and $R_3$ are OPEG; and $R_0$ and $R_1$ are H. In some embodiments, $R_2$ is NHPEG; and $R_0$, $R_1$, and $R_3$ are H. In some embodiments, $R_1$ is OPEG; and $R_0$, $R_2$, and $R_3$ are H. In some embodiments, $R_1$ is CH$_2$—OPPG; and $R_0$, $R_2$, and $R_3$ are H. In some embodiments, $R_3$ is OPPG; and $R_0$, $R_1$, and $R_2$ are H. In some embodiments, $R_2$ is OPPG; and $R_0$, $R_1$, and $R_3$ are H. In some embodiments, $R_2$ and $R_3$ are OPPG; and $R_0$ and $R_1$ are H. In some embodiments, $R_2$ is NHPPG; and $R_0$, $R_1$, and $R_3$ are H. In some embodiments, $R_1$ is OPPG; and $R_0$, $R_2$, and $R_3$ are H. In one embodiment, $R_1$, $R_2$, and $R_3$ are H; and $R_0$ is OPEG-($C_6H_5$). In another embodiment, $R_1$, $R_2$, and $R_3$ are H; and $R_0$ is OPPG-($C_6H_5$).

For zinc ionophores or zinc complexes having a structure of Formula (Va), in some embodiments described herein, each of $R_0$, $R_1$, $R_2$, and $R_3$ is independently H, or an optionally substituted group selected from a mono-hydroxylated group, a dihydroxylated group, a tri-hydroxylated group, a tetra-hydroxylated group, a penta-hydroxylated group, or a saccharide.

For zinc ionophores or zinc complexes having a structure of Formula (Va), in some embodiments described herein, each of $R_0$, $R_1$, $R_2$, and $R_3$ is independently H, a bond, L, wherein L is PEG or PPG; wherein PEG or PPG is —(O-alkylene or O-substituted alkylene)$_x$-O—$R_z$ or -(alkylene-O or substituted alkylene-O)$_x R_z$, where $R_z$ is H, alkyl, $R_0$, $R_1$, $R_2$, or $R_3$; and x is 1, 2, 3, 4, 5, 6, 7, 8, 9, 10, 11, 12, 13, 14, 15, 16, 17, 18, 19, or 20. In some embodiments, PEG is —(OCH$_2$CH$_2$)$_x$OR$_z$ or —(CH$_2$CH$_2$O)$_x$R$_z$. In some embodiments, PPG is —(OCH$_2$CH$_2$CH$_2$)$_x$OR$_z$; —(CH$_2$CH$_2$CH$_2$O)$_x$R$_z$; —(OCH(CH$_3$)CH$_2$)$_x$OR$_z$; —(CH(CH$_3$)CH$_2$)$_x$R$_z$; —(OCH$_2$CH(CH$_3$))$_x$OR$_z$; or —(OCH$_2$CH(CH$_3$))$_x$R$_z$. In some embodiments, one $R_o$ is attached to another $R_0$ on the other side of Formula (Va) via OPEGO; and $R_1$, $R_2$, and $R_3$ are H. In some embodiments, one $R_1$ is attached to another $R_1$ on the other side of Formula (Va) via OPEGO; and $R_0$, $R_2$, and $R_3$ are H. In some embodiments, $R_2$ is attached to another $R_2$ on the other side of Formula (Va) via OPEGO; and $R_0$, $R_1$, and $R_3$ are H. In some embodiments, one $R_2$ is attached to one $R_3$ on the other side of Formula (Va) via OPEGO; and $R_0$ and $R_1$ and the other $R_2$ and $R_3$ are H. In some embodiments, one $R_1$ is attached to one $R_3$ on the other side of Formula (Va) via OPEGO; and $R_0$ and $R_2$ and the other $R_1$ and $R_3$ are H. In some embodiments, one $R_0$ is attached to one $R_3$ on the other side of Formula (Va) via OPEGO; and $R_2$ and $R_1$ and the other $R_0$ and $R_3$ are H. In some embodiments, one $R_0$ is attached to one $R_1$ on the other side of Formula (Va) via OPEGO; and $R_2$ and $R_3$ and the other $R_0$ and $R_1$ are H. In some embodiments, one $R_1$ is attached to one $R_2$ on the other side of Formula (Va) via OPEGO; and $R_0$ and $R_3$ and the other $R_1$ and $R_2$ are H. In some embodiments, one $R_0$ is attached to one $R_2$ on the other side of Formula (Va) via OPEGO; and $R_1$ and $R_3$ and the other $R_0$ and $R_2$ are H. In other embodiments the PEG group is substituted with the PPG group.

For zinc ionophores or zinc complexes having a structure of Formula (Va), in some embodiments described herein, each of $R_0$, $R_1$, $R_2$, and $R_3$ is independently H, or an optionally substituted group selected from a mono-hydroxylated group, a dihydroxylated group, a tri-hydroxylated group, a tetra-hydroxylated group, a penta-hydroxylated group, or a saccharide.

In one embodiment, is a zinc chelator of Formula (Va) wherein L is O-(alkylene or substituted alkylene)-O—. In another embodiment, is a zinc chelator of Formula (Va) wherein L is PEG or PPG. In one embodiment, is a zinc chelator of Formula (Va) wherein L is OPEGO or OPPGO. In another embodiment, is a zinc chelator of Formula (Va) wherein L is (CH$_2$)$_x$PEG(CH$_2$)$_x$ or (CH$_2$)$_x$PPG(CH$_2$)$_x$. In a further embodiment is a zinc chelator of Formula (Va) wherein L is (CH$_2$)$_x$OPEG(CH$_2$)$_x$ or (CH$_2$)$_x$OPPG(CH$_2$)$_x$.

In one embodiment is a zinc chelator of Formula (Va) wherein the metal cation, such as by way of example only, Zn is not bound to the compound of Formula (Va).

In one embodiment is an ionophore or complex comprising Formula (Va) wherein the Zn is replaced by another transition metal cation, such as by way of example only, cations of Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In one embodiment the compound of Formula (Va) forms a 1:1 complex, a 2:1 complex, or a 3:1 complex wherein the Zn is replaced with a transition metal cation, such as by way of example only, Sc, Ti, V, Cr, Mn, Fe, Co, Ni, Cu, Y, Zr, Nb, Mo, Tc, Ru, Rh, Pd, Ag, Cd, Lu, Hf, Ta, W, Re, Os, Ir, Pt, Au, Hg, Lr, Rf, Db, Sg, Bh, Hs, Mt, Ds, Rg, or Uub. In another embodiment, the compound of Formula (Va) forms a 1:1 complex, a 2:1 complex, or a 3:1 complex wherein the Zn cation is replaced with Cu or Au cation. In one embodiment, the compound of Formula (Va) forms a 1:1 complex, a 2:1 complex, or a 3:1 complex wherein the Zn cation is replaced with Cu cation.

In one aspect is a pharmaceutical composition comprising the compound of Formula (Va) and a pharmaceutically acceptable excipient. In one embodiment, the pharmaceutically acceptable excipient is cyclodextrin, carbohydrate excipients, amino acid excipients, detergents, micelles, and dendrimers. In one embodiment, the pharmaceutical composition comprising the compound of Formula (Va) further comprises a cyclodextrin.

Also described herein are methods for synthesizing zinc ionophores, zinc chelators and/or zinc complexes. Described herein are also methods of treating cancer using at least one zinc ionophore, zinc chelator and/or zinc complex. In an aspect described herein, zinc ionophores, zinc complexes can be used to treat cancer by delivering zinc to cancer cells. In another aspect described herein, zinc chelators can be used to treat cancer due to zinc chelation within the cancer cells by the unbound ligand. Also described herein are compositions and methods for treating cancer with combination of an expanded porphyrin metal complex and at least one zinc ionophore, zinc chelator and/or zinc complex or their respective pharmaceutically acceptable derivatives. In certain embodiments, the expanded porphyrin metal complex is a texaphyrin metal complex. In certain embodiments, the texaphyrin metal complex is a texaphyrin gadolinium complex. In certain embodiments, the texaphyrin is motexafin gadolinium (MGd).

Another aspect described herein are pharmaceutical compositions comprising at least one zinc ionophore, and/or zinc complex having a structure selected from Formula (I), Formula (Ia), Formula (Ib), Formula (II), Formula (IIa), Formula (III), Formula (IV), Formula (V), and Formula (Va); and a pharmaceutically acceptable excipient. In one embodiment, the pharmaceutical composition is suitable for intravenous administration or administration by injection. In one embodiment, the pharmaceutical composition comprises water.

Another aspect described herein are zinc chelators having the structure of the group coordinating the zinc ion in structure of Formula (Ib). Such zinc chelators include neutral structures or salt structures, wherein the counterion is any cation other than zinc. Thus, in any of the examples described herein (which describe the use of a zinc chelator) are included zinc chelators coordinated to a labile ion, such as sodium, potassium, or calcium, in which the labile ion can be replaced by zinc following adminstration of the non-zinc coordinated zinc chelator to the patient. Further, for zinc chelators or zinc ionophores capable of binding to multiple zinc ions are included mixed metal complexes in which the zinc chelator binds to different metal ions, or in the case of a zinc ionophore, binds to at least one zinc ion and one other metal ion.

Another aspect described herein are pharmaceutical compositions comprising at least one such zinc chelator; and a pharmaceutically acceptable excipient. In one embodiment, the pharmaceutical composition is suitable for intravenous administration or administration by injection. In one embodiment, the pharmaceutical composition comprises water.

Another aspect described herein relates to the use of compounds of Formula (I), Formula (Ia), Formula (Ib), Formula (II), Formula (IIa), Formula (III), Formula (IV), Formula (V), and Formula (Va) for the formulation of a medicament for use in the treatment of cancer.

Another aspect described herein relates to methods of enhancing solubility of an ionophore, complex, and/or chelator comprising the step of modifying at least one group of the ionophore and/or chelator with an optionally substituted PEG group or hydroxylated group. In some embodiments, the ionophore is a zinc ionophore. In some embodiments, the ionophore is an ionophore for a first row transition metal. In some embodiments, the ionophore for a first row transition metal is an ionophore for Mn(II), Mn(III), Fe(II), Fe(III), Co(II), Co(III), Cu(I), or Cu(II). In some embodiments, the zinc ionophore has a structure of Formula (I). In some embodiments, the unmodified zinc ionophore is ZnHPT. In some embodiments, the modification with polyethylene glycol increases bioavailability of the zinc ionophore as compared to unmodified zinc ionophore.

Another aspect described herein relates to methods of enhancing the biological activity of an ionophore and/or chelator comprising the step of modifying at least one group of the ionophore and/or chelator with an electron-withdrawing or electron-donating (more likely) group. In some embodiments, the ionophore is a zinc ionophore. In some embodiments, the ionophore is an ionophore for a first row transition metal. In some embodiments, the ionophore for a first row transition metal is an ionophore for Mn(II), Mn(III), Fe(II), Fe(III), Co(II), Co(III), Cu(I), or Cu(II). In some embodiments, the zinc ionophore has a structure of Formula (I). In some embodiments, the unmodified zinc ionophore is ZnHPT.

An aspect also described herein relates to a method of treating cancer comprising the step of administering a therapeutically effective amount of at least one ionophore and/or chelator or their respective pharmaceutically acceptable derivatives, wherein the ionophore has at least one functional group selected from polyalkylene oxide, hydroxylated group, or a group having at least one amine, ammonium salt, carboxylate, sulfanyl, sulfinyl, sulfonyl, phosphate, phosphonate, phosphite; or combinations thereof. In some embodiments, the ionophore is an ionophore for a first row transition metal. In some embodiments, the ionophore for a first row transition metal is an ionophore for Mn(II), Mn(III), Fe(II), Fe(III), Co(II), Co(III), Cu(I), or Cu(II).

An aspect also described herein relates to a method of treating cancer comprising the step of administering a therapeutically effective amount of at least one zinc ionophore, zinc complex, and/or zinc chelator or their respective pharmaceutically acceptable derivatives (including, for example chelate complexes of a zinc chelator, in which the zinc chelator coordinates a labile ion, e.g., sodium, potassium or calcium ions), wherein the zinc ionophore, zinc complex, and/or zinc chelator has at least one functional group selected from polyalkylene oxide, hydroxylated group, or a group having at least one amine, ammonium salt, carboxylate, sulfanyl, sulfinyl, sulfonyl, phosphate, phosphonate, phosphite; or combinations thereof. In some embodiments, the zinc ionophore has the structure of any compound having the structure of Formula (I), Formula (Ia), Formula (Ib), Formula (II), Formula (IIa), Formula (III), Formula (IV), Formula (V), and Formula (Va). In some embodiments, the zinc chelator has the structure of the group coordinating zinc in the structure of Formula (Ib). In some embodiments, the zinc ionophore has a mixed structure in which it is chelated by two different zinc chelators, at least one of which has the structure of the group coordinating zinc in the structures of Formula (Ib).

In some embodiments, the zinc ionophore, zinc complex, and/or chelator has an aqueous solubility greater than about 1 millimolar, greater than about 2 millimolar, greater than about 3 millimolar, greater than about 4 millimolar, greater than about 5 millimolar or greater than about 6 millimolar. In some embodiments, the zinc ionophore, zinc complex, and/or zinc chelator increases intracellular zinc concentration. In some embodiments, the zinc ionophore, and/or zinc chelator chelates zinc within the cancer cells. In some embodiments, the zinc ionophore and/or zinc chelator functions to modulate zinc homeostasis in vivo. In some embodiments, the zinc ionophore and/or zinc chelator is modified with at least one polyethylene glycol group. In some embodiments, the zinc ionophore and/or zinc chelator is modified with at least one hydroxylated group. In some embodiments, the zinc ionophore is ZnHPT modified with at least one polyethylene glycol group. In some embodiments, the zinc ionophore is ZnHPT modified with at least one hydroxylated group. In some embodiments, the zinc ionophore and/or zinc chelator comprises a disulfide bond. In some embodiments, the disulfide bond is reduced within cancer cells.

Another aspect described herein relates to a method of treating cancer comprising administering to a patient in need thereof: (a) a therapeutically effective amount of motexafin gadolinium or a pharmaceutically acceptable texaphyrin derivative; and (b) a therapeutically effective amount of at least one zinc ionophore and/or zinc chelator or their respective pharmaceutically acceptable derivatives. In some embodiments, the motexafin gadolinium and the zinc ionophore and/or zinc chelator are sequentially administered to the patient. In some embodiments, the motexafin gadolinium and the zinc ionophore and/or zinc chelator are simultaneously administered to the patient. In some embodiments, the motexafin gadolinium and the zinc ionophore and/or zinc chelator are in a single formulation. In some embodiments, there is a synergistic combination between the motexafin gadolinium and the zinc ionophore and/or zinc chelator or their respective pharmaceutically acceptable derivatives. In some embodiments, the administration is performed using an intravenous injection or infusion.

Another aspect described herein relates to pharmaceutical compositions comprising (a) a therapeutically effective amount of motexafin gadolinium or a pharmaceutically acceptable texaphyrin derivative; and (b) a therapeutically effective amount of at least one zinc ionophore and/or zinc chelator or their respective pharmaceutically acceptable derivatives.

Another aspect described herein relates to an anticancer agent comprising an expanded porphyrin metal complex chemically linked via a linker group to a zinc ionophore and/or zinc chelator. In some embodiments, the zinc ionophore has the structure of the compounds of Formula (I), Formula (Ia), Formula (Ib), Formula (II), Formula (IIa), Formula (III), Formula (IV), Formula (V), and Formula (Va). In some embodiments, the zinc chelator has the structure of the group coordinating to the zinc ion in the compounds of Formula (Ib). In some embodiments, the expanded porphyrin metal complex is a texaphyrin metal complex.

In another aspect, the zinc ionophore and/or zinc complex is a dipyrromethene (including derivatives thereof) bound to a zinc cation, or the zinc chelator is a dipyrromethene (includes derivatives thereof) that can bind a zinc cation. Further, any of the methods described herein, including methods for treating cancer can be used with such a zinc ionophore and/or zinc chelator.

Zinc Pyrithione

ZnHPT, 1-hydroxypyridine-2-thione, is a known zinc ionophore with poor aqueous solubility. Polyvalent metal salts of pyrithione such as 1-hydroxy-2-pyridinethione; 2-pyridinethiol-1-oxide; 2-pyridinethione; 2-mercaptopyridine-N-oxide; pyridinethione; and pyridinethione-N-oxide, are known to be effective biocidal agents and are widely used as fungicides and bacteriocides in paints and metalworking fluids. Synthesis of polyvalent pyrithione salts is described in U.S. Pat. No. 2,809,971, herein incorporated by reference. Other patents disclosing similar compounds and processes for making them include U.S. Pat. Nos. 2,786,847; 3,589,999; 3,590,035; and 3,773,770, herein also incorporated by reference. Pyridinethione are also described as anti-microbial and anti-dandruff agents, for example, in U.S. Pat. No. 2,809,971; U.S. Pat. No. 3,236,733; U.S. Pat. No. 3,753,196; U.S. Pat. No. 3,761,418; U.S. Pat. No. 4,345,080; U.S. Pat. No. 4,323,683; U.S. Pat. No. 4,379,753; and U.S. Pat. No. 4,470,982.

ZnHPT, a commonly employed reagent that increases intracellular zinc in vitro, has been orally administered to laboratory animals for toxicity testing and, in radiolabeled form, to probe zinc homeostasis in vivo. ZnHPT was not found to be particularly toxic under these conditions. However, the complex is insoluble in aqueous media (typically formulated as a suspension in vegetable oil) and is poorly bioavailable (a finding that likely accounts for its low oral toxicity). It is an unmet need to prepare a form of zinc ionophore that is aqueous soluble, in order to better control zinc delivery in vitro and in vivo.

In one aspect, zinc ionophores, zinc chelators and/or zinc complexes can be used to treat cancer by delivering zinc to cancer cells. In another aspect, zinc ionophores, zinc chelators and/or zinc complexes can be used to treat cancer due to zinc chelation within the cancer cells by the unbound ligand. In one embodiment, a zinc ionophore displays at least one of the following chracteristics: (1) adequate water solubility ($\geq$about 0.5 mM); (2) sufficiently stable in a thermodynamic and/or kinetic sense such that bound zinc is not lost to serum proteins present in the plasma or interstitial fluid; and (3) possess an inherent lability sufficient to allow for intracellular zinc release. In further embodiments, the zinc ionophore possesses at least two of these characteristics. In further embodiments, the zinc ionophore possesses all three of these charateristics. In another embodiment, the water solubility of a zinc ionophore described herein is about 0.5 mM. In some embodiments, the aforementioned factors are used to modify known zinc binding motifs to render them more water soluble while making structural adjustments designed to enhance their expected zinc complexation and transport features. This approach will maintain specificity for zinc relative to other cations, such as iron or copper, which could act as interferants. Some embodiments described herein are based on the well known cyclen ($K_d$=1-13.5 µM), dpa ($K_d$=0.2-5 nM), FluoZn ($K_d$=ca. 15 nM), Zinquin (logK$_{\beta2}$ ca. 18), and HPT (logK$_{\beta2}$=5.4). In further or additional embodiments are zinc ionophores that do lose zinc to serum proteins present in the plasma, but can chelate intracellular zinc. In some of these embodiments, such a zinc chelator is an effective agent for treating cancer.

In some embodiments, ditopic binding design (such as 2:1 HPT subunit:zinc cation) is expected to be favored as the result of having two hydroxypyridine thiol subunits incorporated into one macrocyclic framework. Some embodiments relate to the ditopic binding design, a biologically lable bond is inserted in the linker region. Typical biologically labile bonds include, but not limited to, a disulfide bond, an ester bond, or an amide bond. Compounds with a disulfide bond show increased lability in the relatively reducing environment present in cancer cells (as well as in the presence of chemical reductants), as the result of disulfide reduction. The ability of biologically labile bonds to tune the "off rate" for zinc release is critical because it is neither high affinity per se, nor the ability to release zinc rapidly after transport, but rather some combination thereof, that determines in vitro and/or in vivo efficacy.

In some embodiments, administration of at least one zinc ionophore is combined with administration of motexafin gadolinium (MGd). MGd has anticancer (i.e., anti-neoplastic; the terms are used interchangeably herein) activity and combination therapy comprising administration of MGd and at least one zinc ionophore provides, among other benefits, synergistic effects. In some embodiments, at least one zinc ionophore is linked to a texaphyrin core. Having a zinc ionophore and MGd linked together on the same molecule provides (1) enhanced tumor selectivity (and, as a result, reduction of any systemic toxicity effects); (2) the ability to adjust the resulting molecule's spectroscopic properties to enhance detection and activation; and (3) and the synergistic benefit of combining the therapeutic activity of zinc ionophores and MGd.

Methods for Treating Cancer

Without limiting the scope of the compositions and the methods disclosed herein, the methods are used to treat several specific cancers or tumors. Cancer types include (some of which may overlap in scope), by way of example only, adrenal cortical cancer, anal cancer, aplastic anemia, bile duct cancer, bladder cancer, bone cancer, bone metastasis, adult CNS brain tumors, pediatric CNS brain metastases, brain metastases, breast cancer, Castleman Disease, cervical cancer, childhood Non-Hodgkin's lymphoma, colon and rectum cancer, endometrial cancer, esophagus cancer, Ewing's family of tumors, eye cancer, gallbladder cancer, gastrointestinal carcinoid tumors, gastrointestinal stromal tumors, gestational trophoblastic disease, hematological malignancies, Hodgkin's disease, Kaposi'sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, nonmelanoma skin cancer, stomach cancer, testicular cancer, thymus cancer, thyroid cancer, uterine sarcoma, vaginal cancer, vulvar cancer, and Waldenstrom's macroglobulinemia. In one embodiment, the cancers are selected from the group consisting of metastatic brain cancer, lung cancer, glioblastoma, lymphomas, leukemia, renal cell cancer (kidney cancer), head and neck cancer, breast cancer, prostate cancer, and ovarian cancer.

Disclosed herein are methods and compositions to treat lung cancer comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat lung cancer. Treatment options for lung cancer include (which can be provided to a patient in conjunction with administration of the pharmaceutical compositions described herein), by way of example only, surgery, immunotherapy, radiation therapy, chemotherapy, photodynamic therapy, or a combination thereof. Some possible surgical options for treatment of lung cancer are a segmental or wedge resection, a lobectomy, or a pneumonectomy. Radiation therapy may be external beam radiation therapy or brachytherapy.

Disclosed herein are methods and compositions to treat CNS neoplasms comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat CNS neoplasms. Treatment options for CNS neoplasms include (which can be provided to a patient in conjunction with administration of the pharmaceutical compositions described herein), by way of example only, surgery, radiation therapy, immunotherapy, hyperthermia, gene therapy, chemotherapy, and combination of radiation and chemotherapy. Doctors also may prescribe steroids to reduce the swelling inside the CNS.

Disclosed herein are methods to treat kidney cancer comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical composition are used to treat kidney cancer. Kidney cancer (also called renal cell cancer or renal adenocarcinoma) is a disease in which malignant cells are found in the lining of tubules in the kidney. Treatment options for kidney cancer include (which can be provided to a patient in conjunction with administration of the pharmaceutical compositions described herein) surgery, radiation therapy, chemotherapy and immunotherapy. Some possible surgical options to treat kidney cancer include, by way of example only, partial nephrectomy, simple nephrectomy and radical nephrectomy. Radiation therapy may be external beam radiation therapy or brachytherapy. Stem cell transplant may be used to treat kidney cancer.

Disclosed herein are methods to treat lymphoma comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat lymphoma. Treatment options for lymphoma include (which can be provided to a patient in conjunction with administration of the pharmaceutical compositions described herein), by way of example only, chemotherapy, immunotherapy, radiation therapy and high-dose chemotherapy with stem cell transplant. Radiation therapy may be external beam radiation therapy or brachytherapy.

Disclosed herein are methods for treating breast cancer comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat breast cancer. Treatment options for breast cancer include (which can be provided to a patient in conjunction with administration of the pharmaceutical compositions described herein), by way of example only, surgery, immunotherapy, radiation therapy, chemotherapy, endocrine therapy, or a combination thereof. A lumpectomy and a mastectomy are two possible surgical procedures available for breast cancer patients.

Disclosed herein are methods for treating ovarian cancer, comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat ovarian cancer. Treatment options for ovarian cancer include (which can be provided to a patient in conjunction with administration of the pharmaceutical compositions described herein), by way of example only, surgery, immunotherapy, chemotherapy, hormone therapy, radiation therapy, or combinations thereof. Some possible surgical procedures include debulking, and a unilateral or bilateral oophorectomy and/or a unilateral or bilateral salpigectomy.

Disclosed herein are methods for treating cervical cancer, comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat cervical cancer. Treatment options for cervical cancer include (which can be provided to a patient in conjunction with administration of the pharmaceutical compositions described herein), by way of example only, surgery, immunotherapy, radiation therapy and chemotherapy. Some possible surgical options are cryosurgery, a hysterectomy, and a radical hysterectomy. Radiation therapy for cervical cancer patients includes external beam radiation therapy or brachytherapy.

Disclosed herein are methods to treat prostate cancer, comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat prostate cancer. Treatment options for prostate cancer include (which can be provided to a patient in conjunction with administration of the pharmaceutical compositions described herein), by way of example only, surgery, immunotherapy, radiation therapy, cryosurgery, hormone therapy, and chemotherapy. Possible surgical procedures to treat prostate cancer include, by way of example only, radical retropubic prostatectomy, a radical perineal prostatectomy, and a laparoscopic radical prostatectomy. Some radiation therapy options are external beam radiation, including three dimensional conformal radiation therapy, intensity modulated radiation therapy, and conformal proton beam radiation therapy. Brachytherapy (seed implantation or interstitial radiation therapy) is also an available method of treatment for prostate cancer. Cryosurgery is another possible method used to treat localized prostate cancer cells. Hormone therapy, also called androgen deprivation therapy or androgen suppression therapy, may be used to treat prostate cancer. Several methods of this therapy are available including an orchiectomy in which the testicles, where 90% of androgens are produced, are removed. Another method is the administration of luteinizing hormone-releasing hormone (LHRH) analogs to lower androgen levels. The LHRH analogs available include leuprolide, nafarelin, goserelin, triptorelin, and histrelin. An LHRH antagonist may also be administered, such as abarelix. Treatment with an antiandrogen agent, which blocks androgen activity in the body, is another available therapy. Such agents include flutamide, bicalutamide, and nilutamide. This therapy is typically combined with LHRH analog administration or an orchiectomy, which is termed a combined androgen blockade (CAB). Chemotherapy may be appropriate where a prostate tumor has spread outside the prostate gland and hormone treatment is not effective. Anti-cancer drugs may be administered to slow the growth of prostate cancer, reduce symptoms and improve the quality of life.

Disclosed herein are methods for treating leukemia, comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat leukemia. Treatment options for leukemia include (which can be provided to a patient in conjunction with administration of the pharmaceutical compositions described herein), by way of example only, immunotherapy, radiation therapy, chemotherapy, bone marrow or peripheral blood stem cell transplantation, or a combination thereof. Radiation therapy includes external beam radiation and may have side effects. Anti-cancer drugs may be used in chemotherapy to treat leukemia. Monoclonal antibody therapy may be used to treat AML patients. Small molecules or radioactive chemicals may be attached to these antibodies before administration to a patient in order to provide a means of killing leukemia cells in the body. The monoclonal antibody, gemtuzumab ozogamicin, which binds CD33 on AML cells, may be used to treat AML patients unable to tolerate prior chemotherapy regimens. Bone marrow or peripheral blood stem cell transplantation may be used to treat AML patients. Some possible transplantation procedures are an allogenic or an autologous transplant.

Disclosed herein are methods and compositions to treat head and neck cancer, comprising administration of a pharmaceutical composition comprising compounds having a structure of Formula (I), Formula (Ia), Formula (Ib), Formula (II), Formula (IIa), Formula (III), Formula (IV), Formula (V), and Formula (Va), or their respective combinations with a texaphyrin metal complex, including motexafin gadolinium. In some embodiments, the pharmaceutical compositions are used to treat head and neck cancer. Treatment options for head and neck cancer include (which can be provided to a patient in conjunction with administration of the pharmaceutical compositions described herein), by way of example only, surgery, radiation, chemotherapy, combined modality therapy, gene therapy, either alone or in combination thereof.

Formulations, Routes of Administration, and Effective Doses

The pharmaceutical compositions described herein can be administered in either single or multiple doses by any of the accepted modes of administration of agents having similar utilities, for example as described in those patents and patent applications incorporated by reference above, including by oral administration, rectal administration, intra-arterial injection, intravenously, intraperitoneally, parenterally, intramuscularly, or subcutaneously.

In one embodiment, administration is parenteral, including, by injection. The forms in which the pharmaceutical compositions described herein may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the pharmaceutical compositions described herein in the required amount in the appropriate solvent with various other ingredients as enumerated above, as required, followed by, e.g., a sterilizing method, including by way of example only, sterile filtration, heating, exposure to radiation, and other known methods. Generally, dispersions are prepared by incorporating the various sterilized pharmaceutical compositions described herein into a sterile vehicle which contains the basic dispersion medium and the required other ingredients from those enumerated above. In the case of sterile powders for the preparation of sterile injectable solutions, the methods of preparation are vacuum-drying and freeze-drying techniques, which yield a powder plus any additional desired ingredient from a previously sterile-filtered solution thereof.

The compositions are optionally formulated in a unit dosage form. The term "unit dosage form(s)" refers to physically discrete units suitable as unitary dosages for human subjects and other mammals, each unit containing a predetermined quantity of active material calculated to produce the desired therapeutic effect, in association with a suitable pharmaceutical excipient (e.g., an ampoule). The pharmaceutical compositions described herein are effective over a wide dosage range and are generally administered in a pharmaceutically effective amount. The amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

The pharmaceutical composition of the present disclosure may be administered in a therapeutically effective amount, employing a method of administration and a pharmaceutical formulation as discussed above, and optionally a means of activation of the compound (through a therapeutic energy or agent) as is known in the art. The therapeutic energy or agent to be used includes photodynamic therapy, radiation sensitization, chemotherapy, sonodynamic therapy, and neutron bombardment. The pharmaceutical composition comprising texaphyrin can be administered by intravenous injection, followed by a waiting period of from as short a time as about several minutes or about 3 hours to as long as about 72 or about 96 hours (depending on the treatment being effected) to facilitate intracellular uptake and clearance from the plasma and extracellular matrix prior to the administration of photoirradiation. Dose levels for certain uses may range from about 0.05 mg/kg to about 20 mg/kg administered in single or multiple doses (e.g., before each fraction of photoirradiation).

The optimum length of time between administration of the pharmaceutical compositions described herein and light treatment can vary depending on the mode of administration, the form of administration, and the type of target tissue. Typically, the pharmaceutical compositions described herein persists for a period of minutes to hours, depending on the formulation, the dose, the infusion rate, as well as the type of tissue and tissue size.

When employing photodynamic therapy, a target area is treated with light, for example at about 740±16.5 nm. After the photosensitized pharmaceutical composition comprising texaphyrin as described herein is been administered, the tissue being treated is photo irradiated usually either about 440 to about 540 nm or about 700 to about 800 nm, or about 450 to about 520 nm, or about 720 to about 780 nm, or about 460 to about 500 nm or about 725 to about 760 nm. The light source may be a laser, a light-emitting diode, or filtered light from, for example, a xenon lamp; and the light may be administered topically, endoscopically, or interstitially (via, e.g., a fiber optic probe), or intra-arterially. In one embodiment, the light is administered using a slit-lamp delivery system. The fluence and irradiance during the photo irradiating treatment can vary depending on the type of tissue, depth of target tissue, and the amount of overlying fluid or blood. For example, a total light energy of about 100 J/cm2 can be delivered at a power of 200 mW to 250 mW, depending upon the target tissue.

Administration with Chemotherapeutic Drugs

Pharmaceutical compositions as described herein, may be administered before, at the same time as, or after administration of one or more chemotherapeutic drugs. The pharmaceutical composition may be administered as a single dose, or it may be administered as two or more doses separated by an interval of time. The pharmaceutical composition may be administered concurrently with, or from about 1 minute to about 12 hours following administration of a chemotherapeutic drug. In another embodiment, the pharmaceutical composition may be administered concurrently with, or from about 5 minutes to about 5 hours following administration of a chemotherapeutic drug. In another embodiment, the pharmaceutical composition may be administered concurrently with, or from about 4 to about 5 hours following administration of a chemotherapeutic drug. The dosing protocol may be repeated, from one to three times, for example.

Administering a pharmaceutical composition as described herein and a chemotherapeutic drug to the subject may be prior to, concurrent with, or following vascular intervention. The method may begin at a time roughly accompanying a vascular intervention, such as an angioplastic procedure, for example. Multiple or single treatments prior to, at the time of, or subsequent to the procedure may be used. "Roughly accompanying a vascular intervention" refers to a time period within the ambit of the effects of the vascular intervention. Typically, an initial dose of a pharmaceutical as described herein and chemotherapeutic drug will be within 6 to 12 hours of the vascular intervention, preferably within 6 hours thereafter. Follow-up dosages may be made at weekly, biweekly, or monthly intervals. Design of particular protocols depends on the individual subject, the condition of the subject, the design of dosage levels, and the judgment of the attending practitioner.

A "chemotherapeutic agent" may be, but is not limited to, one of the following: an alkylating agent such as a nitrogen mustard, an ethyleneimine or a methylmelamine, an alkyl sulfonate, a nitrosourea, or a triazene; an antimetabolite such as a folic acid analog, a pyrimidine analog, or a purine analog; a natural product such as a vinca alkaloid, an epipodophyllotoxin, an antibiotic, an enzyme, taxane, or a biological response modifier; miscellaneous agents such as a platinum coordination complex, an anthracenedione, an anthracycline, a substituted urea, a methyl hydrazine derivative, or an adrenocortical suppressant; or a hormone or an antagonist such as an adrenocorticosteroid, a progestin, an estrogen, an antiestrogen, an androgen, an antiandrogen, or a gonadotropin-releasing hormone analog. Chemotherapeutic agents are used in the treatment of cancer and other neoplastic tissue. Preferably, the chemotherapeutic agent is a nitrogen mustard, an epipodophyllotoxin, an antibiotic, or a platinum coordination complex. A more preferred chemotherapeutic agent is bleomycin, doxorubicin, taxol, taxotere, etoposide, 4-OH cyclophosphamide, cisplatin, or platinum coordination complexes analogous to cisplatin. A presently preferred chemotherapeutic agent is doxorubicin, taxol, taxotere, cisplatin, or Pt complexes analogous to cisplatin. Various chemotherapeutic agents, their target diseases, and treatment protocols are presented in, for example, *Goodman and Gilman's The Pharmacological Basis of Therapeutics,* Ninth Ed., Pergamon Press, Inc., 1990; and Remington: *The Science and Practice of Pharmacy,* Mack Publishing Co., Easton, Pa., 1995; both of which are incorporated by reference.

The pharmaceutical compositions of the present disclosure may be administered before, at the same time, or after administration of one or more chemotherapeutic drugs. The pharmaceutical compositions of the present disclosure may be administered as a single dose, or it may be administered as two or more doses separated by an interval of time. The pharmaceutical compositions of what is presently disclosed may be administered concurrently with, or from about one minute to about 12 hours following, administration of a chemotherapeutic drug. In one embodiment, the pharmceutical composition may be administered concurrently with, or from about 5 min to about 5 hr, administration of a chemotherapeutic drug. In another embodiment, the pharmaceutical composition may be administered concurrently with, or from about 4 to about 5 hr, administration of a chemotherapeutic drug. The dosing protocol may be repeated, from one to three times, for example. Administration may be intra-arterial injection, intravenous, intraperitoneal, intramuscular, subcutaneous, oral, topical, or via a device such as a stent, for example, with parenteral and intra-arterial administration being preferred, and intra-arterial being more preferred.

Administration for Radiation Sensitization

Certain embodiments of the pharmaceutical compositions as described herein, wherein the metal is gadolinium, may be administered via intravenous infusion over about a 5 to 10 minute period, followed by a waiting period of about 2 to 5 hours to facilitate intracellular uptake and clearance from the plasma and extracellular matrix prior to the administration of radiation.

When employing whole brain radiation therapy, a course of about 30 Gy in about ten (10) fractions of radiation may be administered over consecutive days excluding weekends and holidays. In the treatment of brain metastases, whole brain megavolt radiation therapy is delivered with 60Co teletherapy or a ≧4 MV linear accelerator with isocenter distances of at least 80 cm, using isocentric techniques, opposed lateral fields and exclusion of the eyes. A minimum dose rate at the midplane in the brain on the central axis is about 0.5 Gy per minute.

Pharmaceutical compositions comprising texaphyrin metal complexes as described herein used as radiation sensitizers may be administered before, or at the same time as, or after administration of the ionizing radiation. The pharmaceutical composition comprising texaphyrin metal complexes as described herein may be administered as a single dose, as an infusion, or it may be administered as two or more doses separated by an interval of time. Where the pharmaceutical composition comprising texaphyrin metal complexes as described herein is administered as two or more doses, the time interval between the administrations may be from about one minute to a number of days, from about 5 minutes to about 1 day, or from about 10 minutes to about 10 hours. The dosing protocol may be repeated, from one to ten or more times, for example. Dose levels for radiation sensitization may range from about 0.05 mg/kg to about 20 mg/kg administered in single or multiple doses (e.g. before each fraction of radiation).

Administering a pharmaceutical composition comprising texaphyrin metal complexes as described herein to the subject may be prior to, concurrent with, or following vascular intervention, and the intervention is followed by photoirradiation. The method may begin prior to, such as about 24 to 48 hours prior to, or at a time roughly accompanying vascular intervention, for example. Multiple or single treatments prior to, at the time of, or subsequent to the procedure may be used. "Roughly accompanying the vascular intervention" refers to a time period within the ambit of the effects of the vascular intervention. Typically, an initial dose of the pharmaceutical composition and light will be within 1 to 24 hours of the vascular intervention, preferably within about 5 to 24 hours thereafter. Follow-up dosages may be made at weekly, biweekly, monthly or longer intervals. Design of particular protocols depends on the individual subject, the condition of the subject, the design of dosage levels, and the judgment of the attending practitioner.

Administration for Sonodynamic Therapy

The use of texaphyrins in sonodynamic therapy is described in U.S. patent application Ser. No. 09/111,148, which was converted to U.S. Provisional Application Ser. No. 60/155,256, from which a continuation was filed on Jan. 5, 2001, having U.S. patent application Ser. No. 09/755,824, now abandoned, which is incorporated herein by reference. Texaphyrin is administered before administration of the ultrasound. The texaphyrin may be administered as a single dose, or it may be administered as two or more doses separated by an interval of time. Parenteral administration is typical, including by intravenous and interarterial injection. Other common routes of administration can also be employed.

Ultrasound is generated by a focused array transducer driven by a power amplifier. The transducer can vary in diameter and spherical curvature to allow for variation of the focus of the ultrasonic output. Commercially available therapeutic ultrasound devices may be employed in the practice of such a method. The duration and wave frequency, including the type of wave employed may vary, and the preferred duration of treatment will vary from case to case within the judgment of the treating physician. Both progressive wave mode patterns and standing wave patterns have been successful in producing cavitation of diseased tissue. When using progressive waves, the second harmonic can advantageously be superimposed onto the fundamental wave. Types of ultrasound employed in such a method are ultrasound of low intensity, non-thermal ultrasound, i.e., ultrasound generated within the wavelengths of about 0.1 MHz and about 5.0 MHz and at intensities between about 3.0 and about 5.0 W/cm2.

In further applications, the pharmaceutical composition comprising texaphyrin metal complexes as described herein, where M is $Gd^{+3}$, may be administered with NAD(P)H, ascorbate and other reducing agents under approximate physiological conditions, leading to reactive oxygen species generation. Depletion of these reducing agents will inhibit biochemical pathways that in vivo utilize reducing agents to effect repair of the damage inflicted by reactive oxygen species. Such a method may be used to treat cancer and cardiovascular diseases. See U.S. Pat. No. 6,825,186, which is incorporated by reference in its entirety.

EXAMPLES

Example 1

Synthesis of 5-PEG-[1]-ZnHPT, 5-PEG-[2]-ZnHPT, and 5-PEG-[3]-ZnHPT

Figure 2:
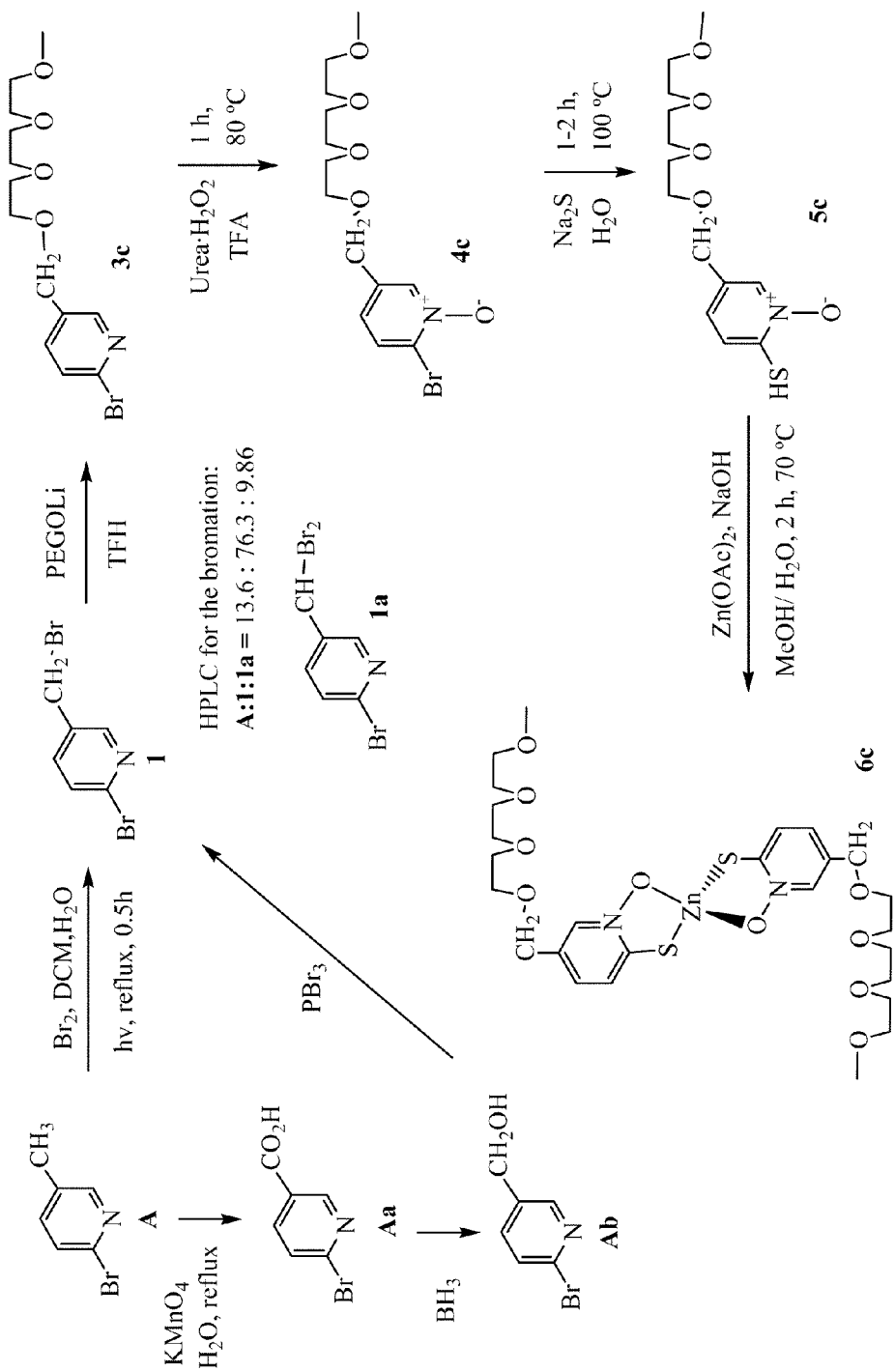
FIG. 2 presents a non-limiting synthesis of 5-PEG-[3]-ZnHPT, also designated herein as PEGZnHPT.
Figure 3:
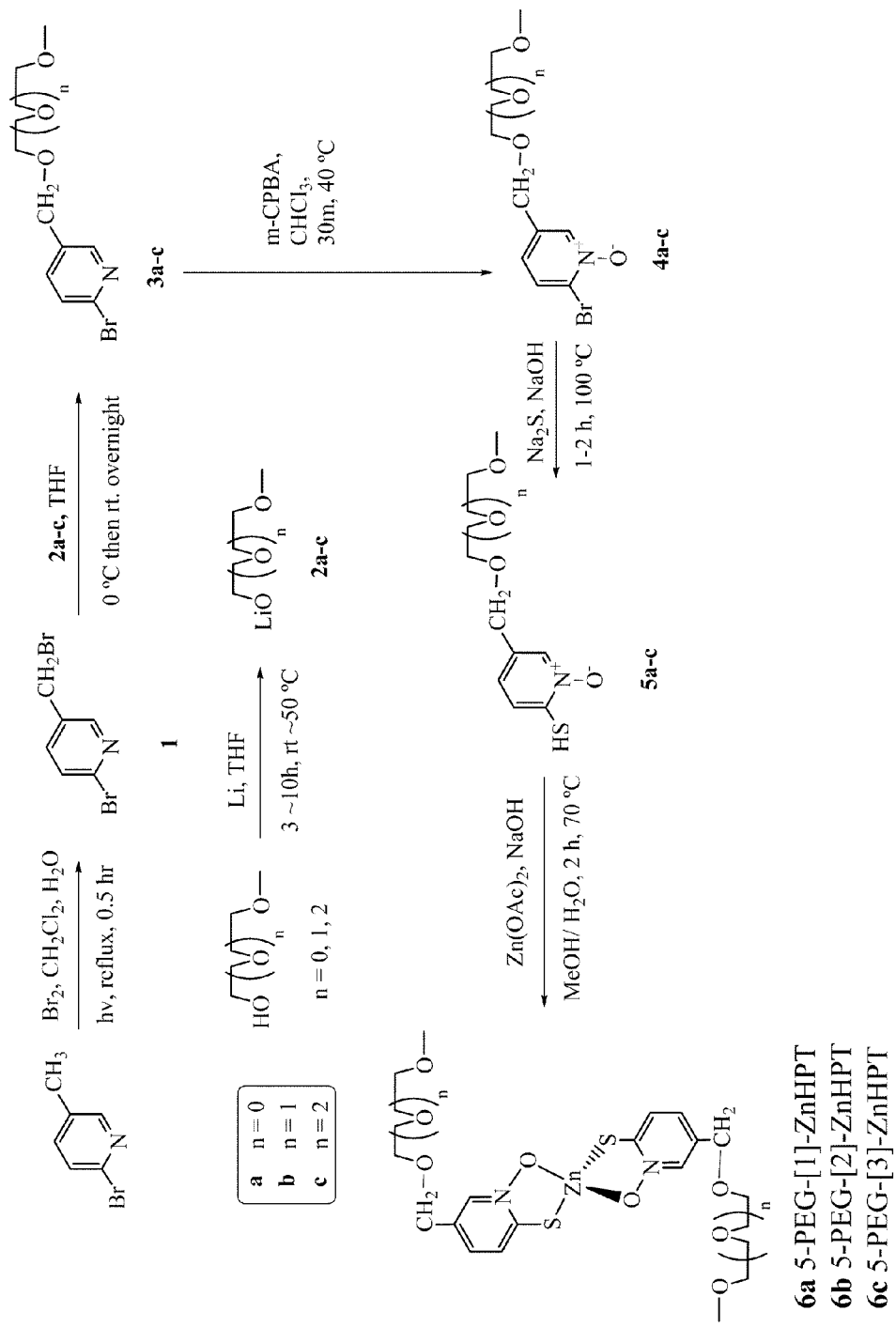
FIG. 3 presents a non-limiting synthesis of 5-PEG-[3]-ZnHPT, also designated herein as PEGZnHPT, 5-PEG-[2]-ZnHPT, and 5-PEG-[1]-ZnHPT.
Figure 4:
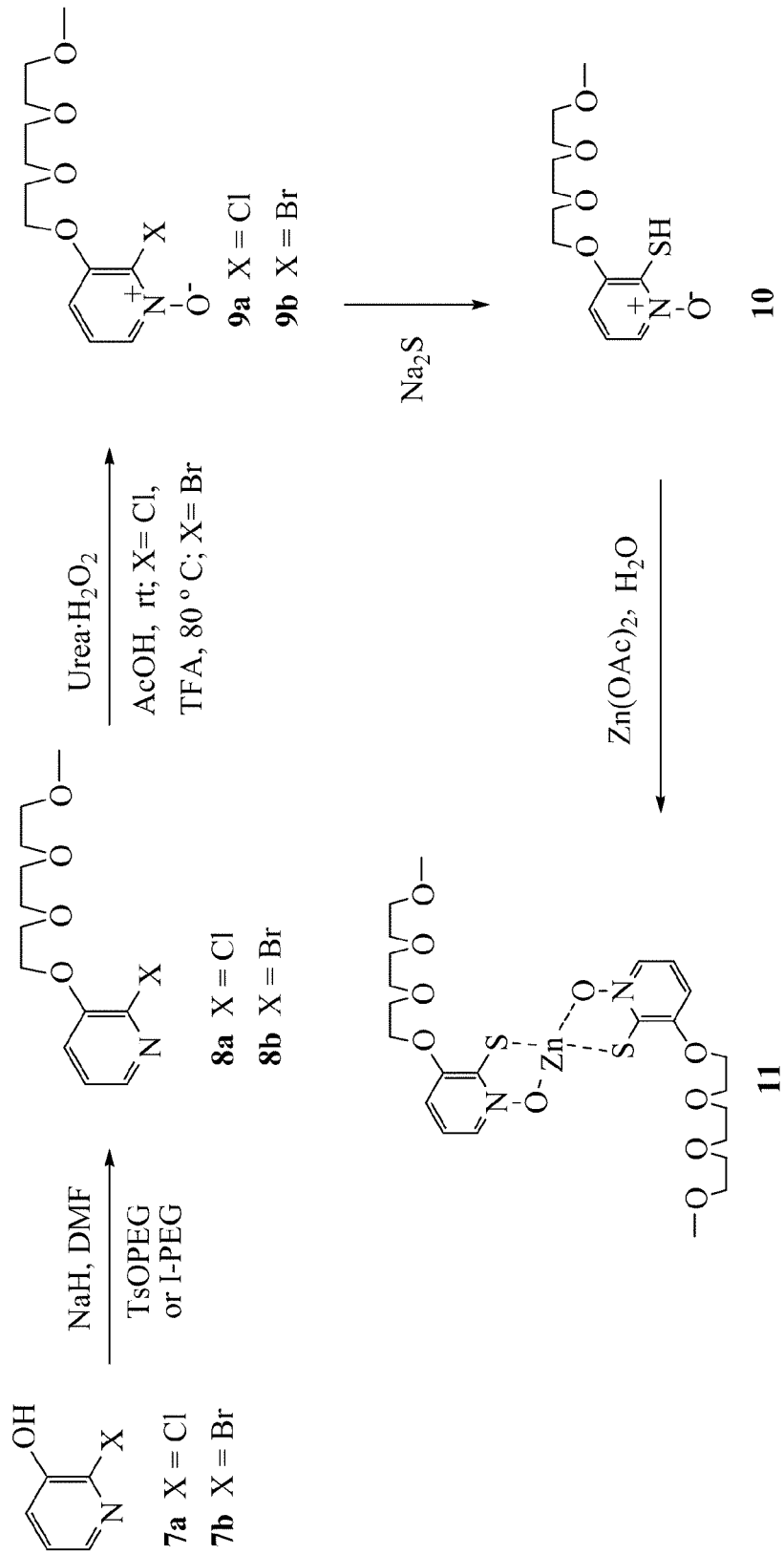
FIG. 4 presents a non-limiting synthesis of 3-O—PEG-ZnHPT.
Figure 5:
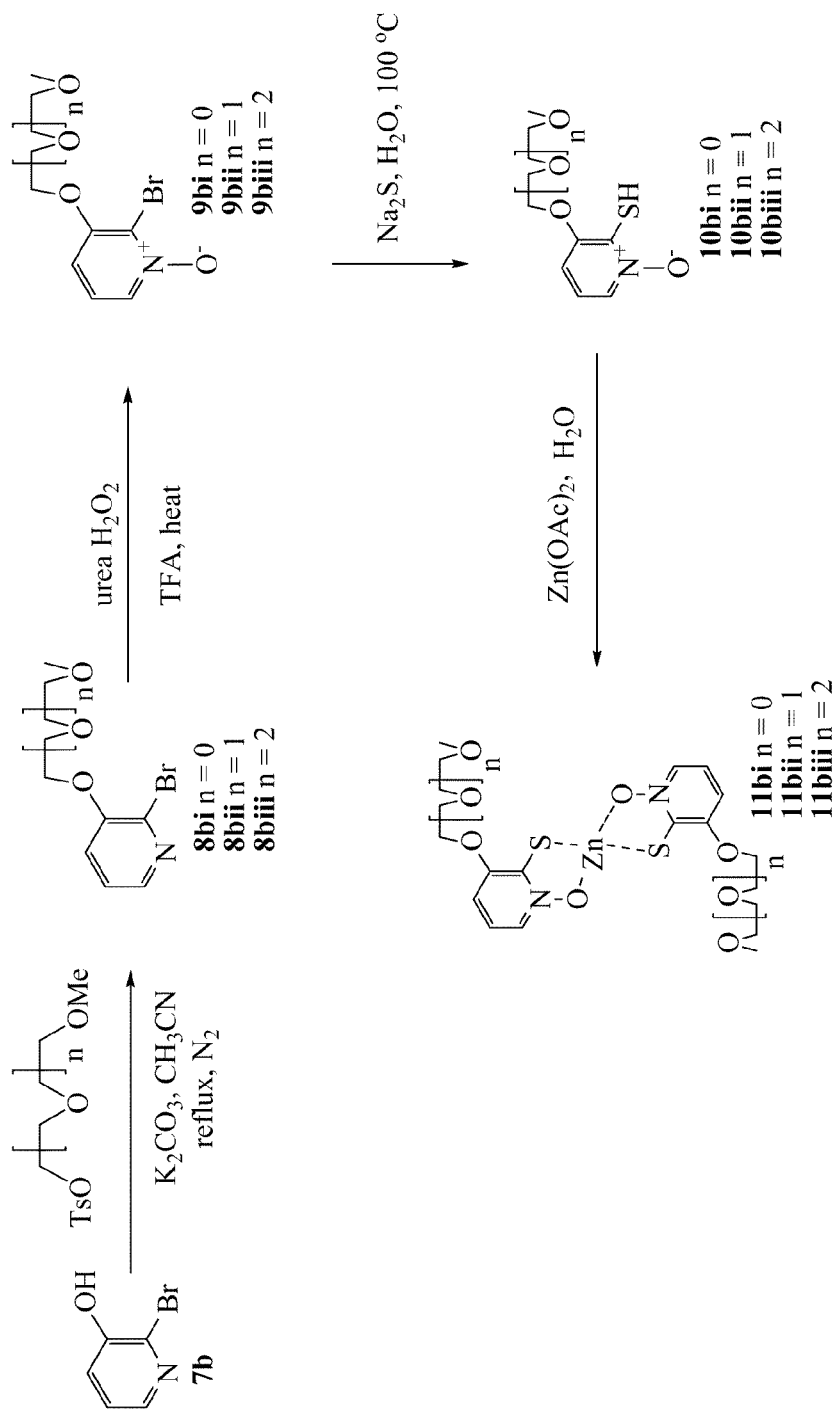
FIG. 5 presents a non-limiting synthesis of 3-O—PEG-ZnHPT.
Figure 6:
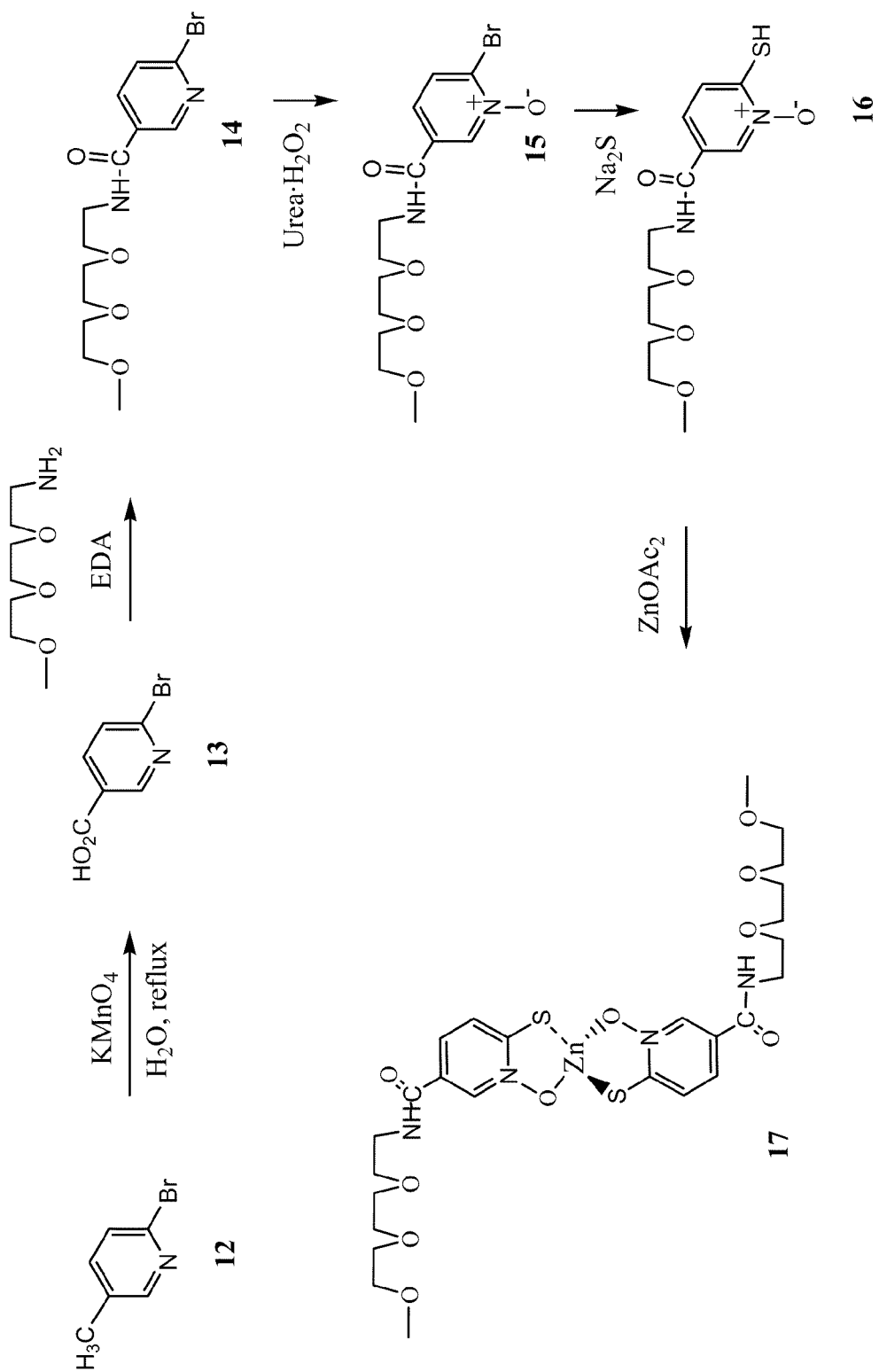
FIG. 6 presents a non-limiting synthesis of 5-CONHPEG-ZnHPT.
Figure 7:
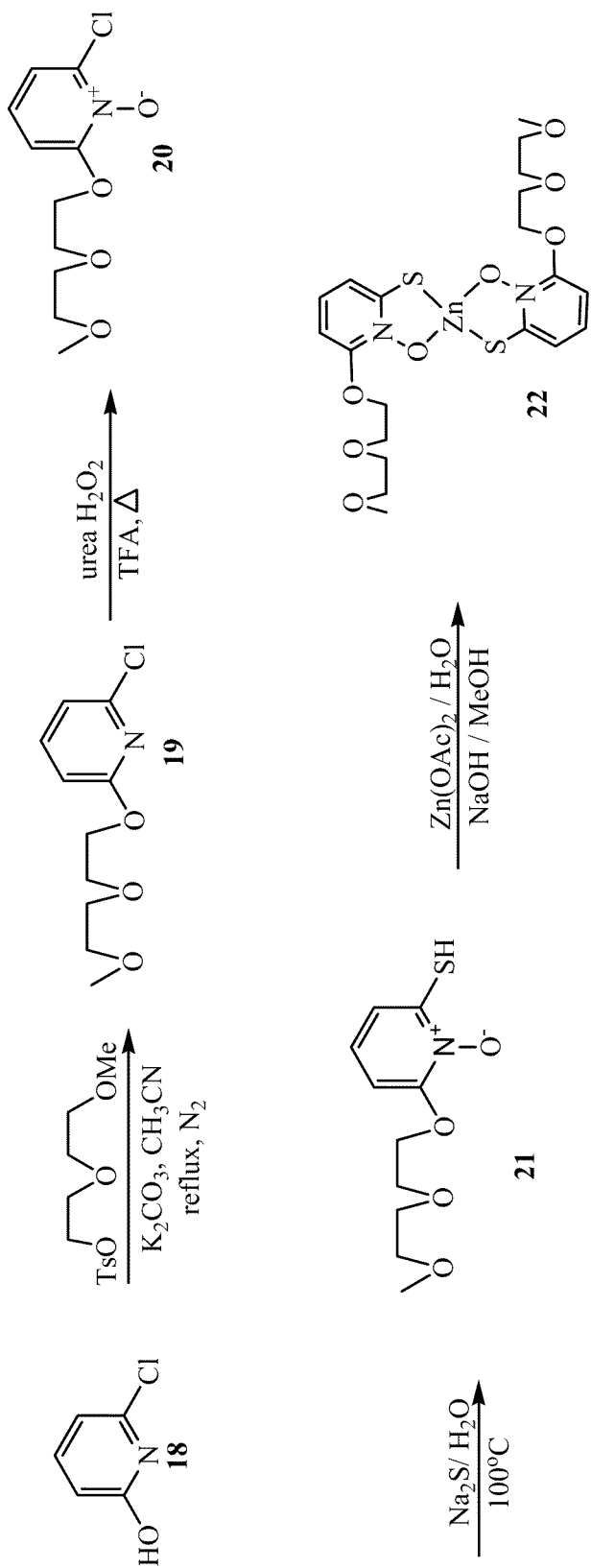
FIG. 7 presents a non-limiting synthesis of 6-OPEG-Zn-HPT.
Figure 8:
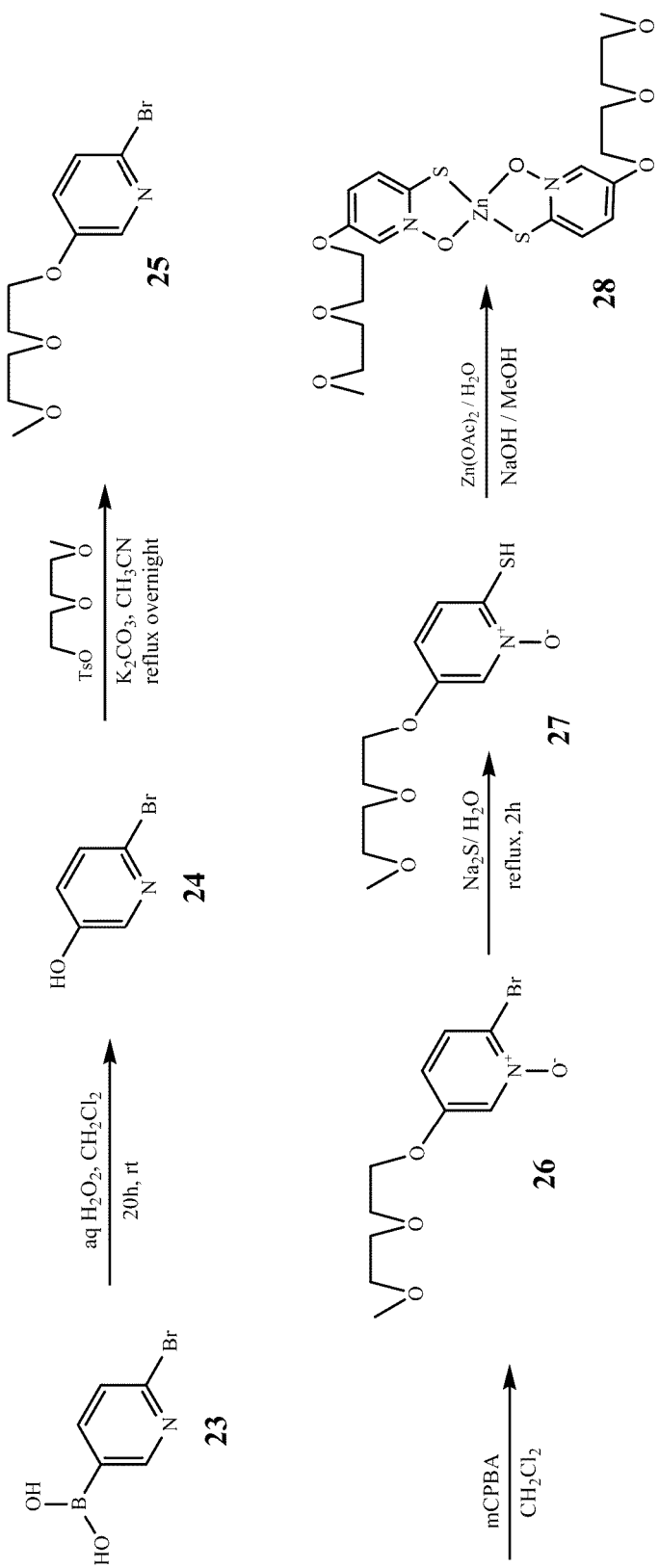
FIG. 8 presents a non-limiting synthesis of 5-OPEG-Zn-HPT.
Figure 9:
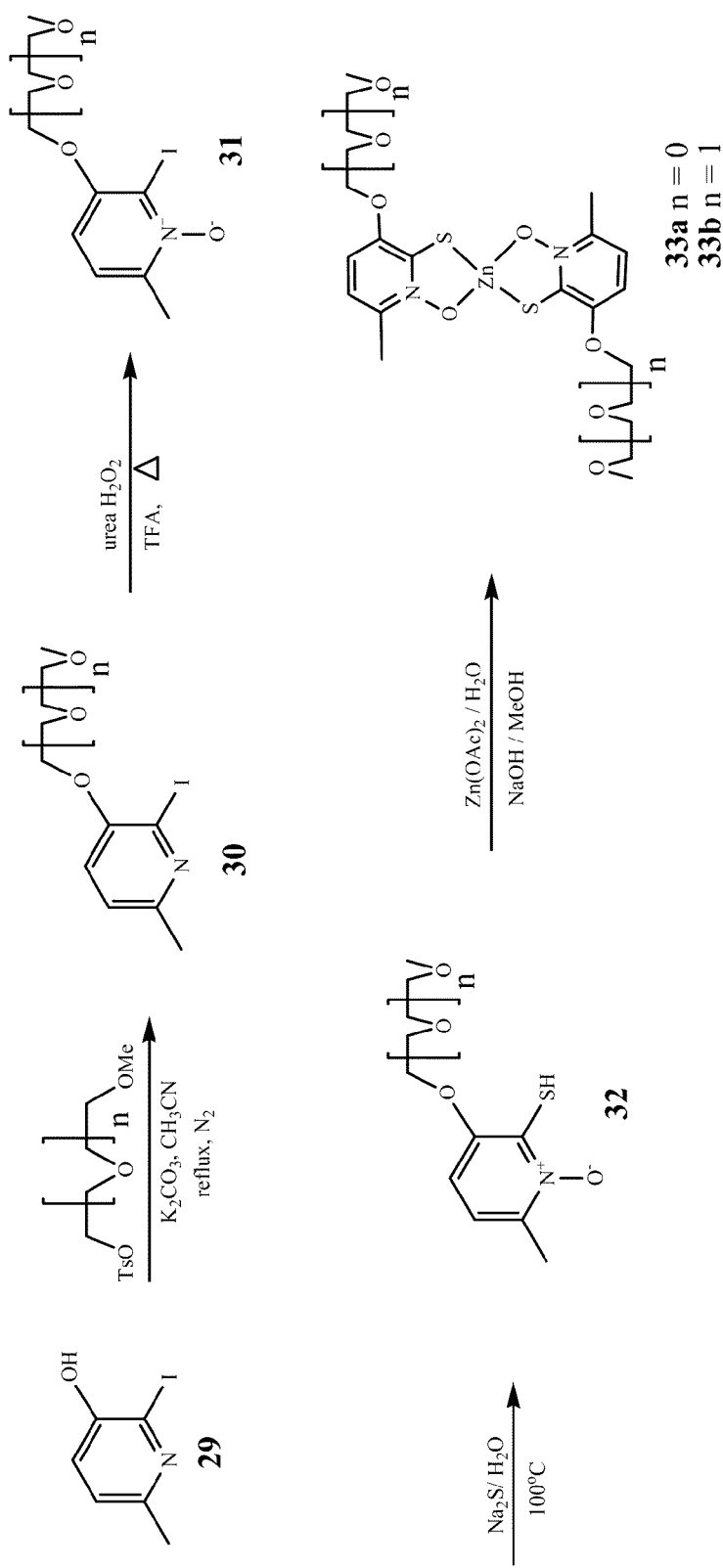
FIG. 9 presents a non-limiting synthesis of ZnHPT derivatives.
Figure 10:
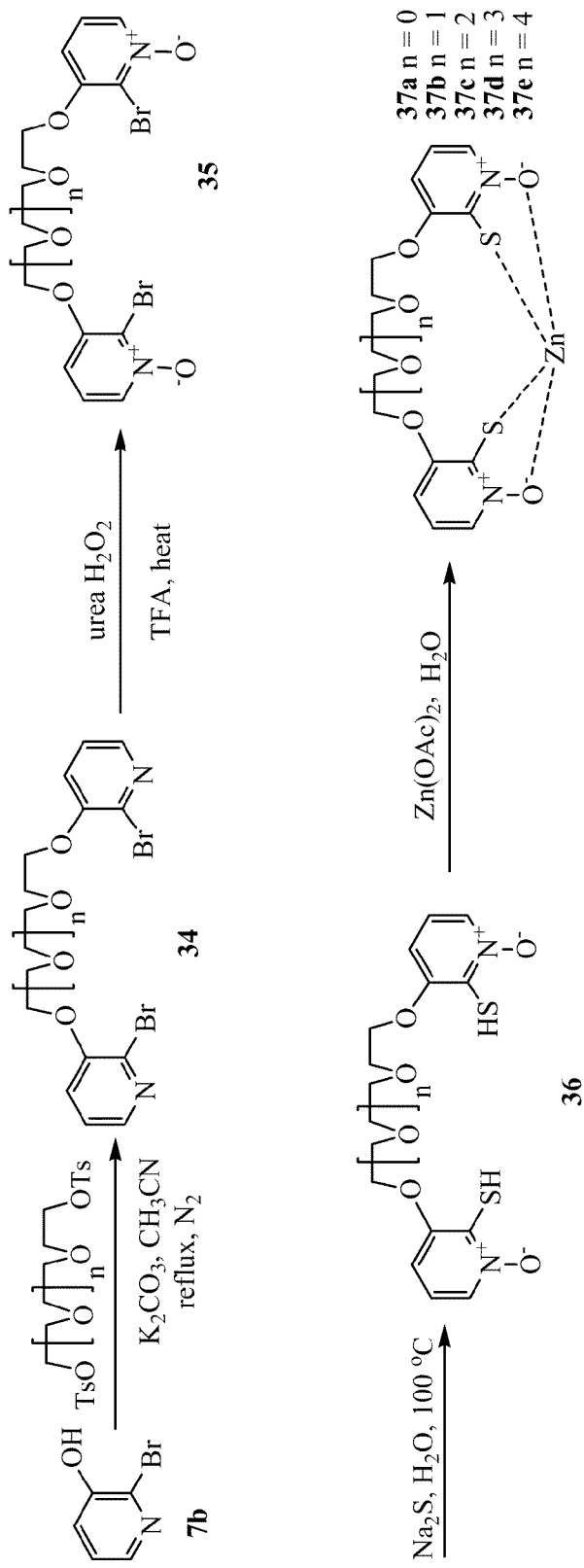
FIG. 10 presents a non-limiting synthesis of ZnHPT derivatives.
Figure 11:
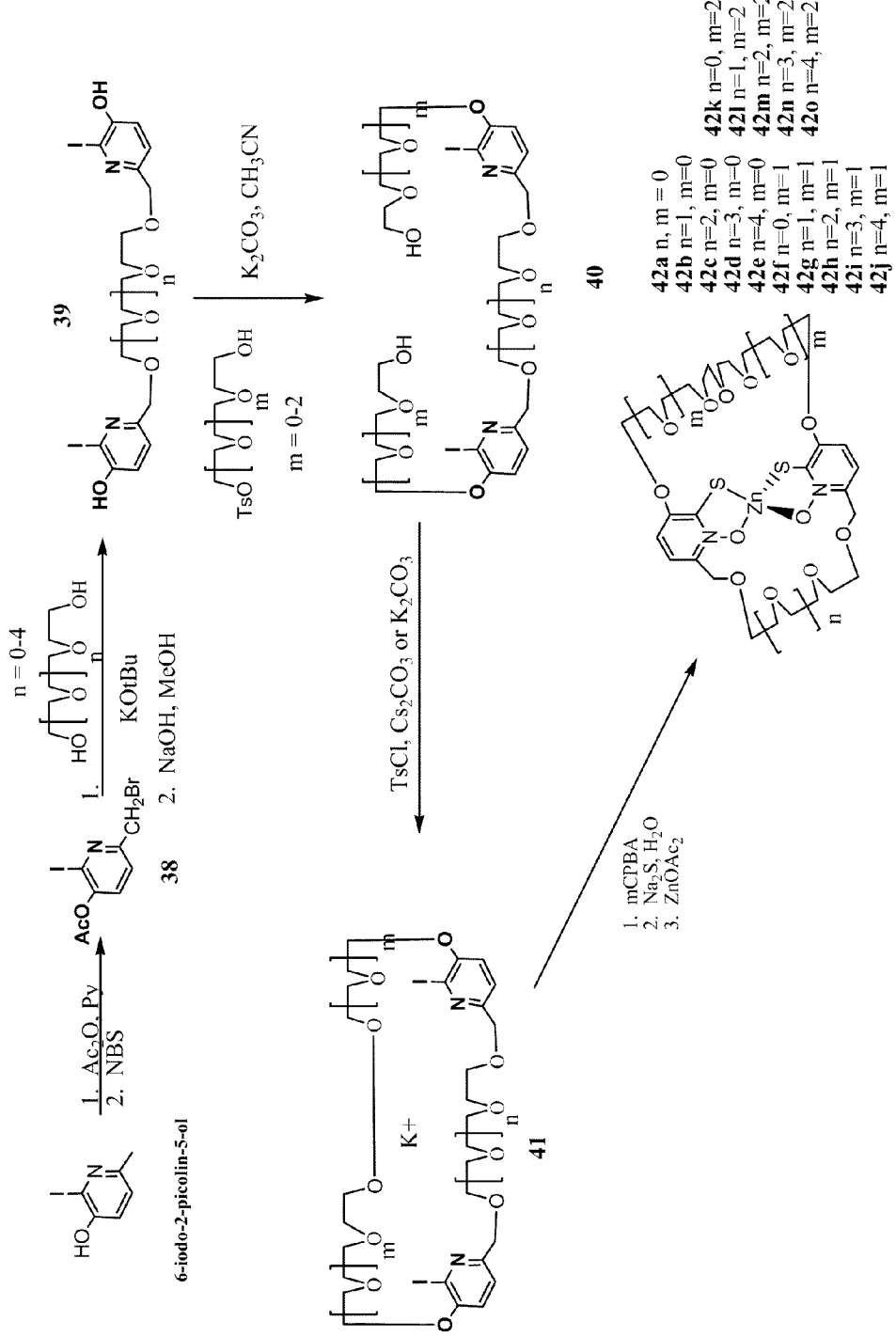
FIG. 11 presents a non-limiting synthesis of ZnHPT derivatives.
Figure 12:
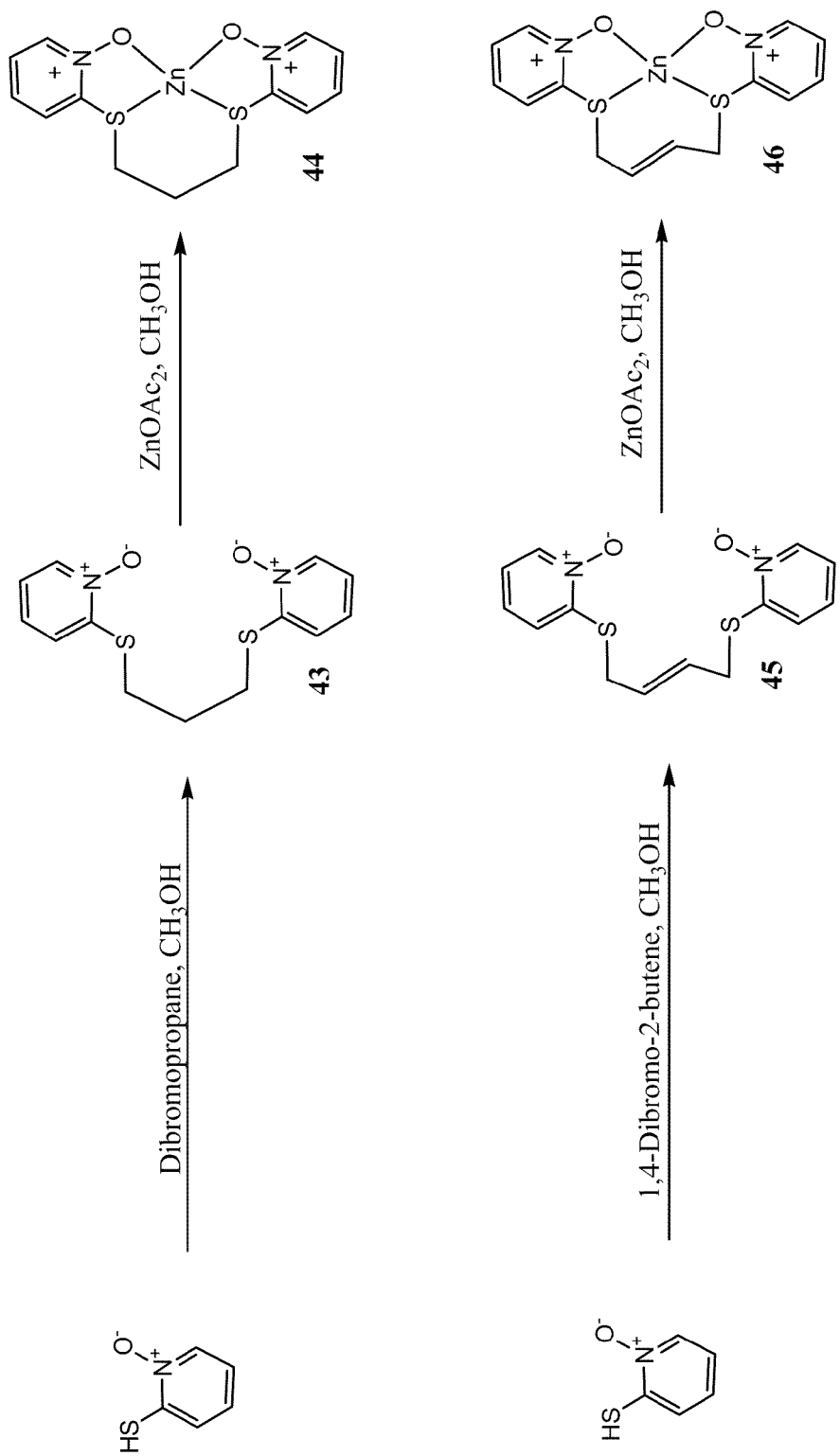
FIG. 12 presents a non-limiting synthesis of a ZnHPT derivative.
Figure 13:
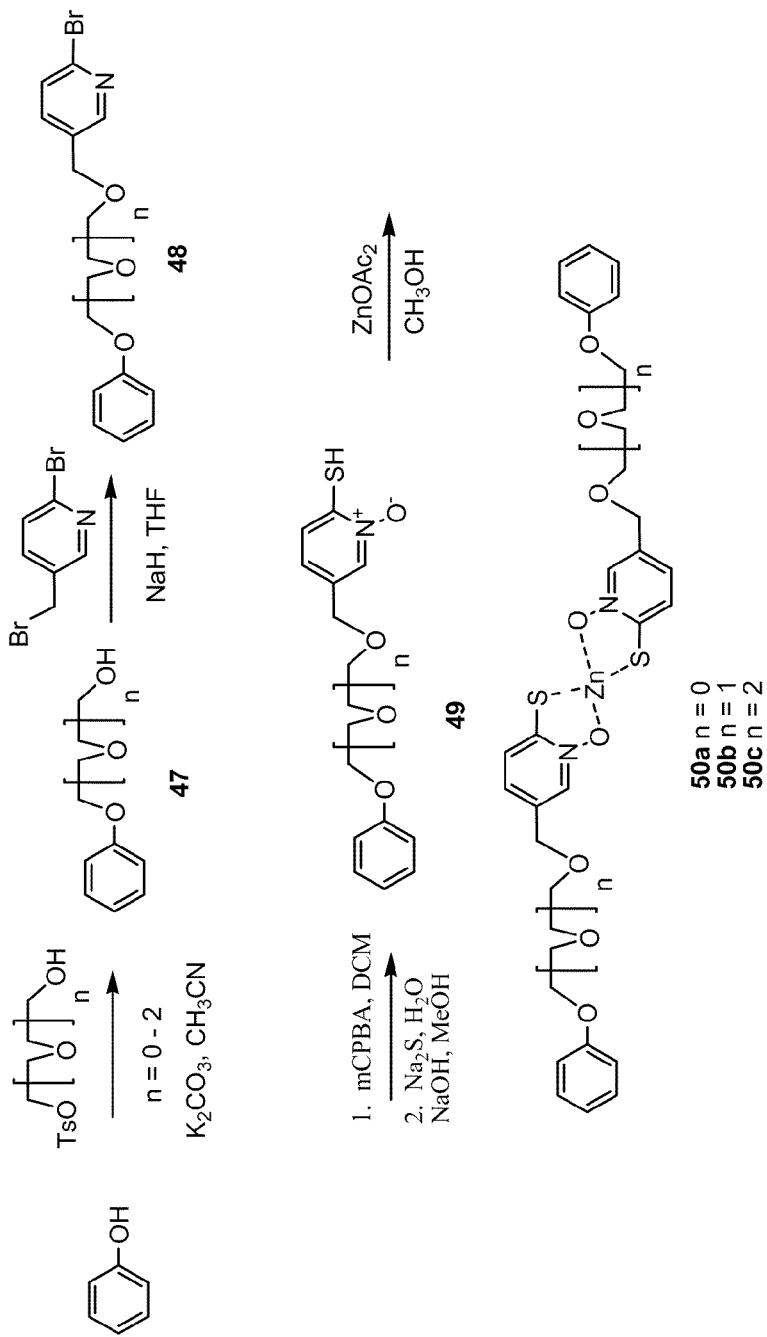
FIG. 13 presents a non-limiting synthesis of ZnHPT derivatives.
Figure 14:
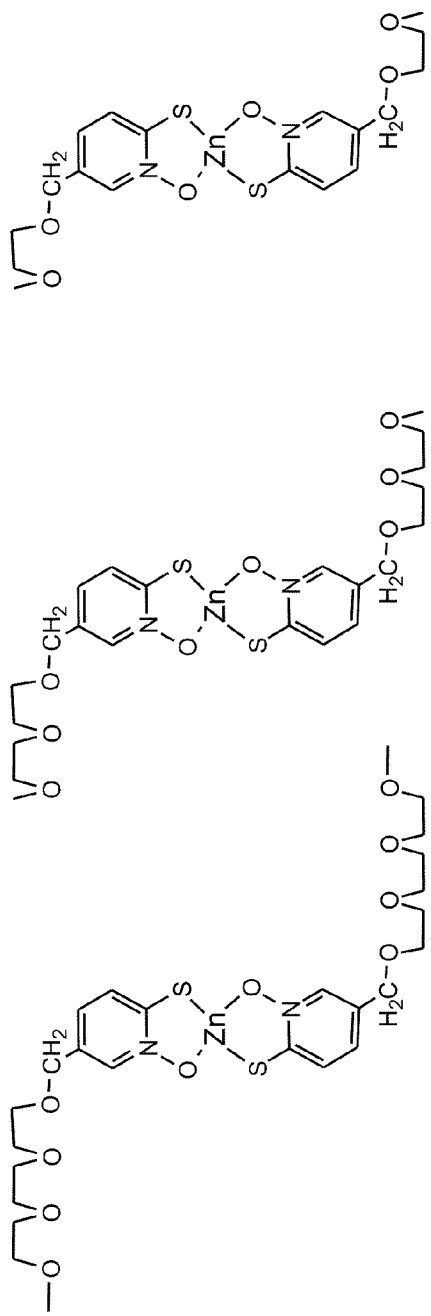
FIG. 14 presents non-limiting examples of zinc ionophores, zinc chelators, and/or zinc complexes.
Figure 14:
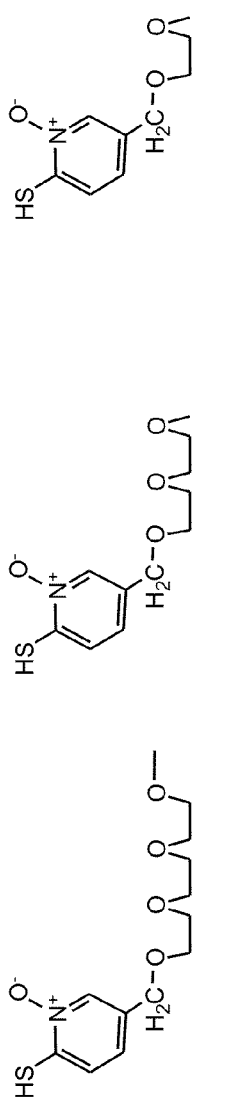
Figure 15:
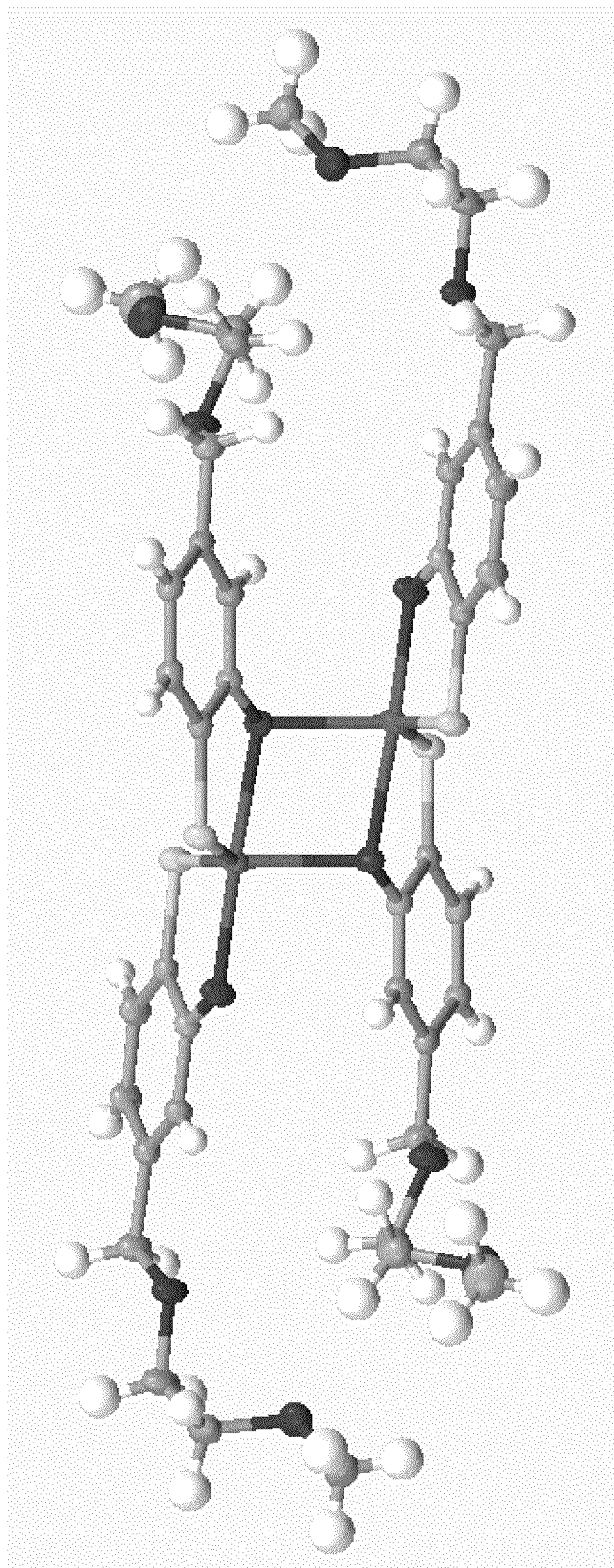
FIG. 15 presents a single crystal X-ray diffraction structure of a complex of Formula I wherein $R_0$, $R_2$, $R_3$=H and $R_1$=$CH_2OCH_2CH_2OCH_3$.
Figure 16:
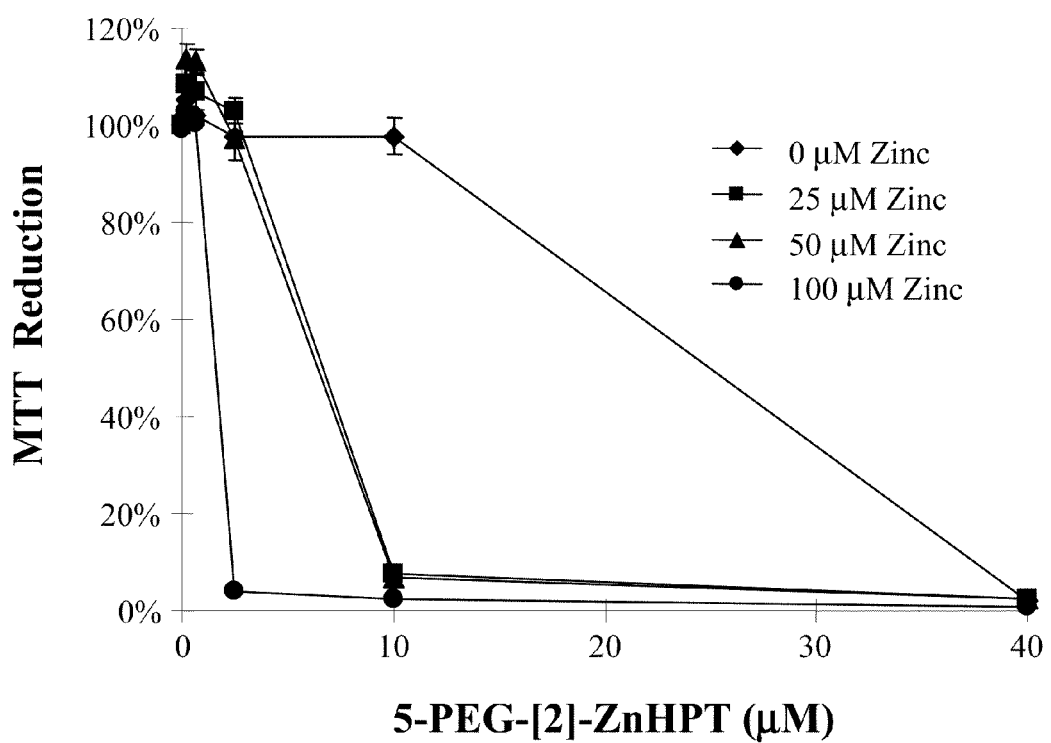
FIG. 16 presents a non-limiting example of 24 h plateau phase cell culture studies with A549 cells in which MTT reduction is measured as a function of zinc concentration and 5-PEG-[2]-ZnHPT concentration.
Figure 17:
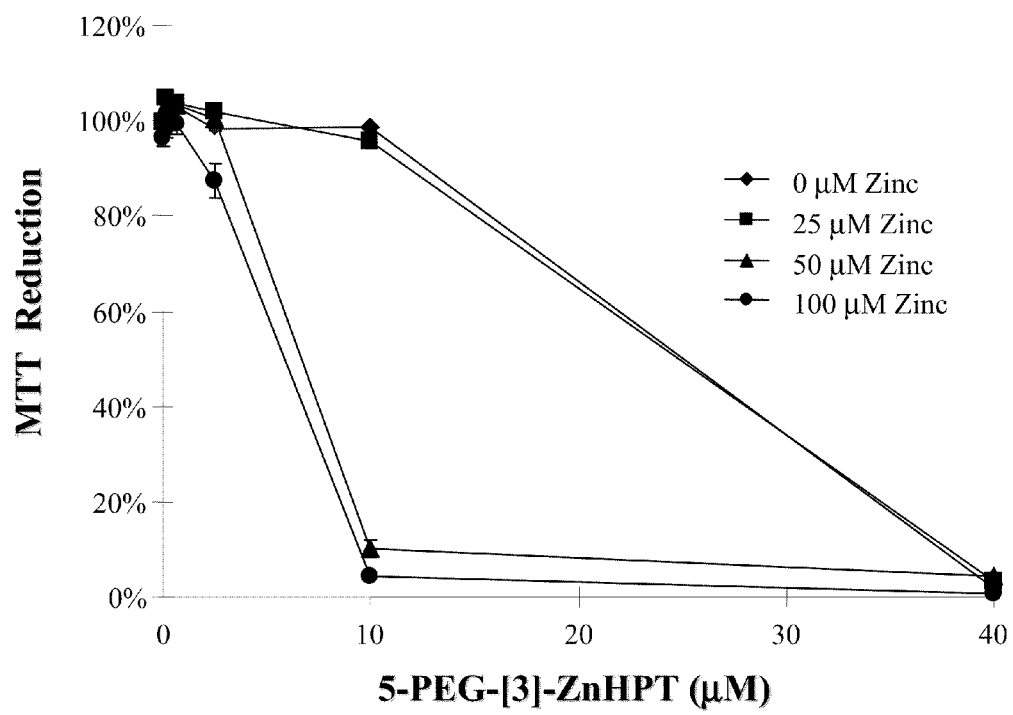
FIG. 17 presents a non-limiting example of 24 h plateau phase cell culture studies with A549 cells in which MTT reduction is measured as a function of zinc concentration and 5-PEG-[3]-ZnHPT concentration.
Figure 18:
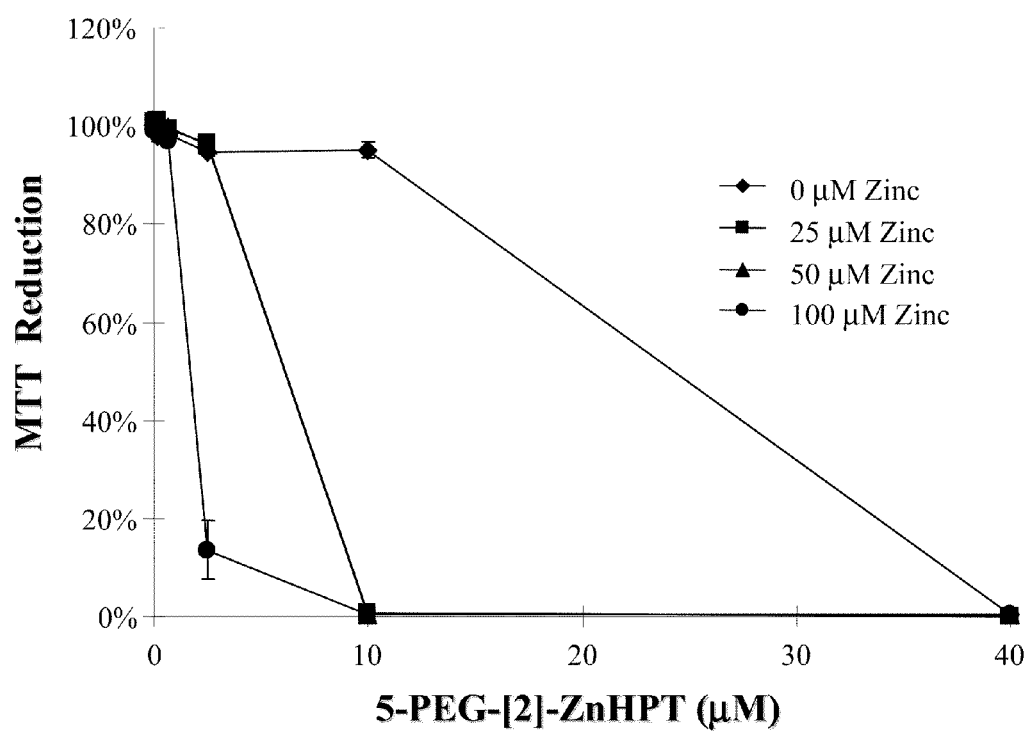
FIG. 18 presents a non-limiting example of 24 h plateau phase cell culture studies with PC3 cells in which MTT reduction is measured as a function of zinc concentration and 5-PEG-[2]-ZnHPT concentration.
Figure 19:
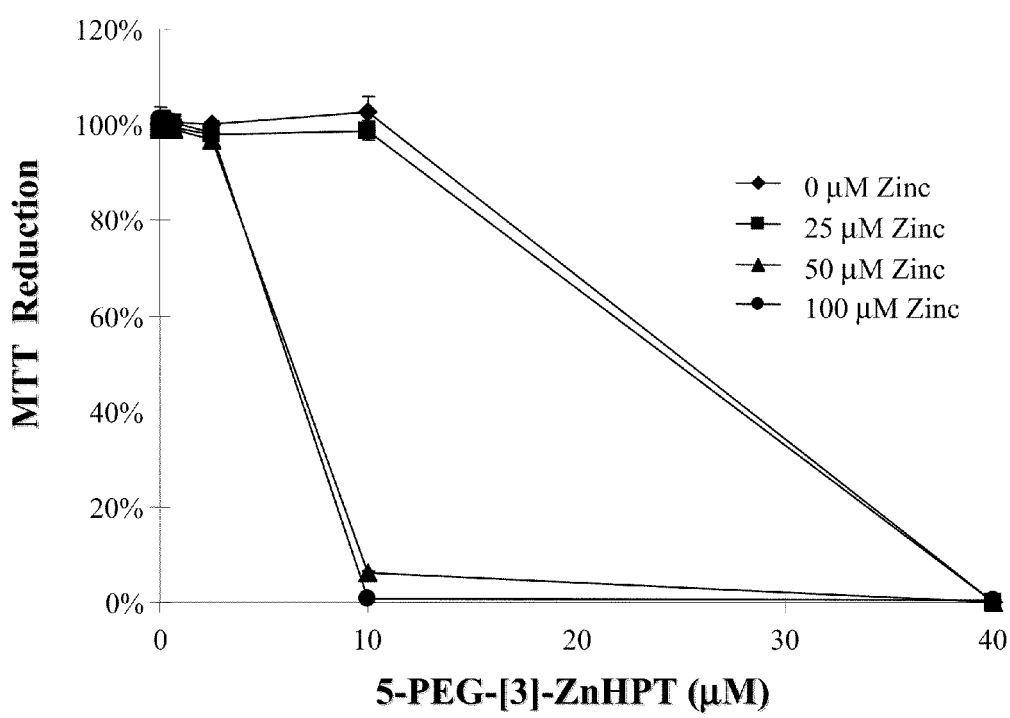
FIG. 19 presents a non-limiting example of 24 h plateau phase cell culture studies with PC3 cells in which MTT reduction is measured as a function of zinc concentration and 5-PEG-[3]-ZnHPT concentration.
Figure 20:
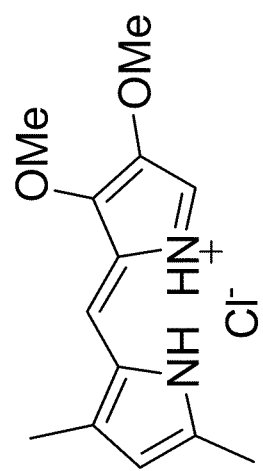
FIG. 20 presents non-limiting examples of zinc chelators.
Figure 20:
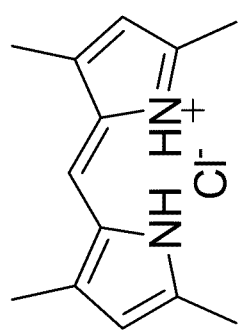
Figure 21:
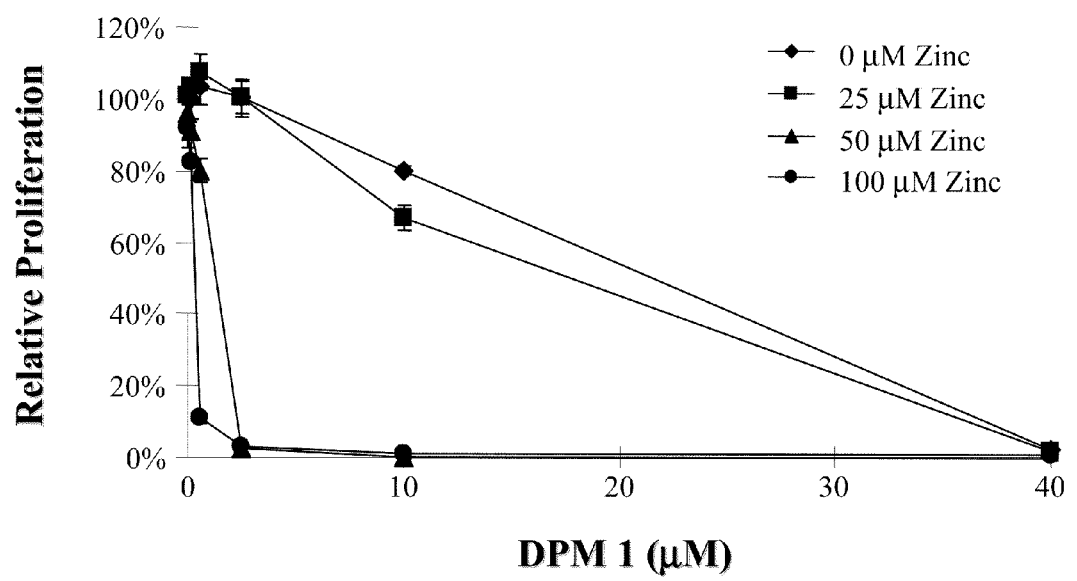
FIG. 21 presents a non-limiting example of 24 h exponential phase cell culture studies with A549 cells in which MTT reduction is measured as a function of zinc concentration and DPM 1 concentration.
Figure 22:
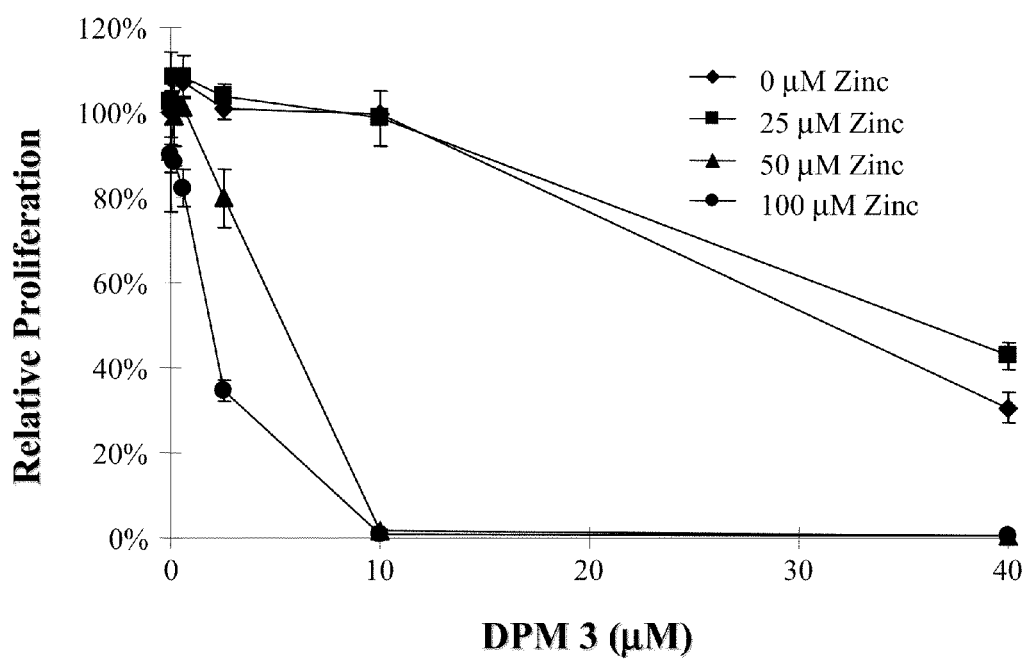
FIG. 22 presents a non-limiting example of 24 h exponential phase cell culture studies with A549 cells in which MTT reduction is measured as a function of zinc concentration and DPM 3 concentration.
Figure 23:
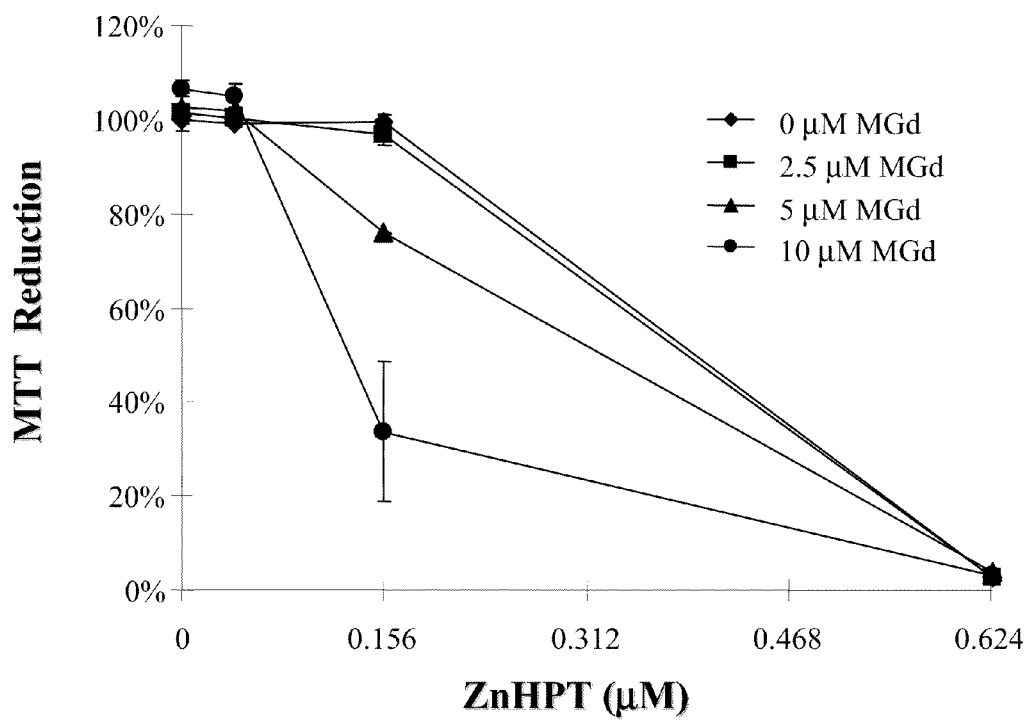
FIG. 23 presents a non-limiting example of 24 h plateau phase cell culture studies with A549 cells in which MTT reduction is measured as a function of MGd concentration and ZnHPT concentration, and in which all studies were done in the presence of 50 µM of $Zn^{2+}$.
Figure 24:
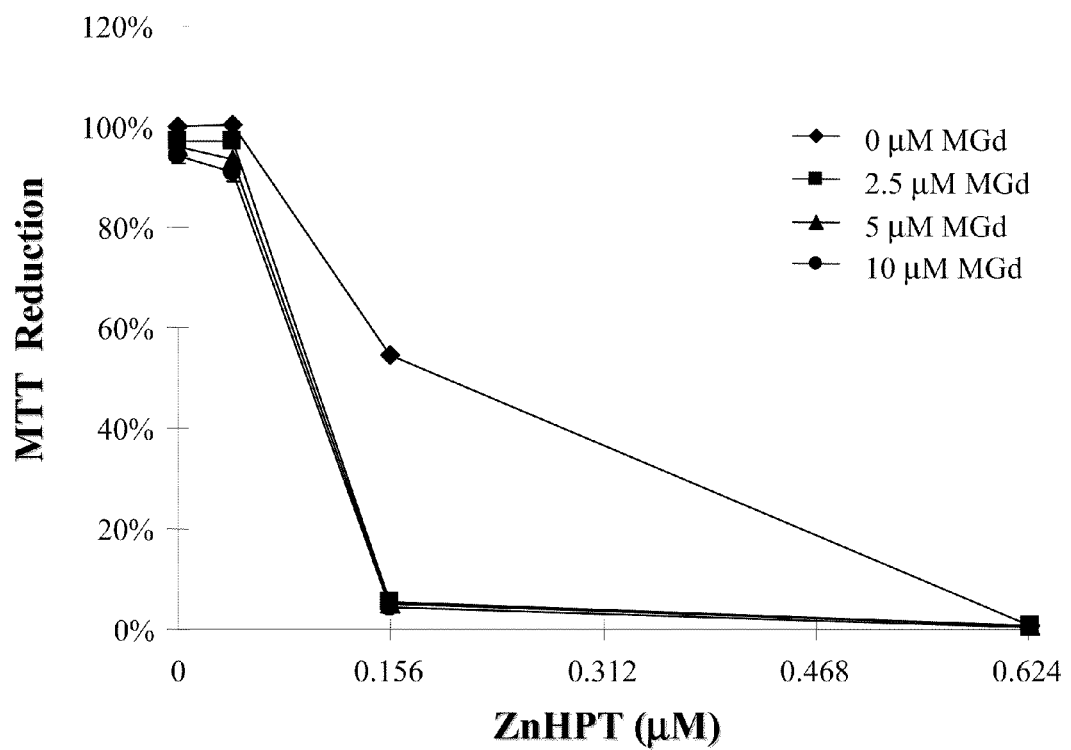
FIG. 24 presents a non-limiting example of 24 h plateau phase cell culture studies with PC3 cells in which MTT reduction is measured as a function of MGd concentration and ZnHPT concentration, and in which all studies were done in the presence of 50 µM of $Zn^{2+}$.
Figure 25:
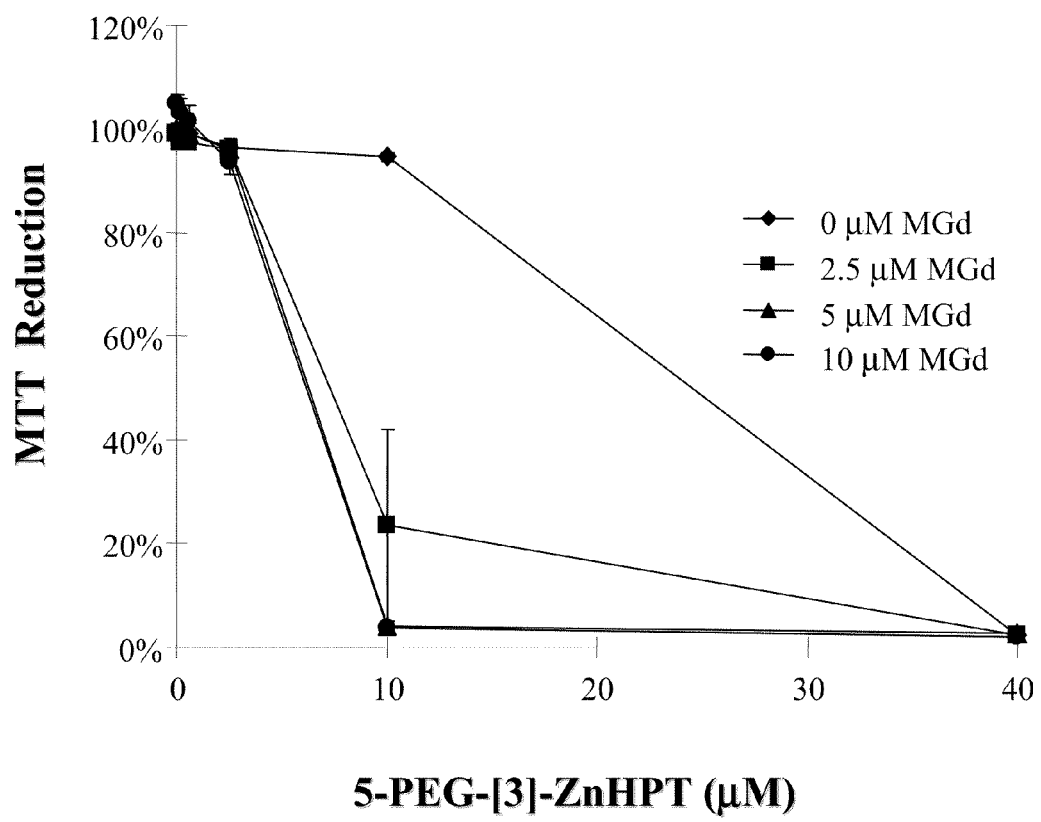
FIG. 25 presents a non-limiting example of 24 h plateau phase cell culture studies with A549 cells in which MTT reduction is measured as a function of MGd concentration and PEGZnHPT concentration, and in which all studies were done in the presence of 50 µM of $Zn^{2+}$.
Figure 26:
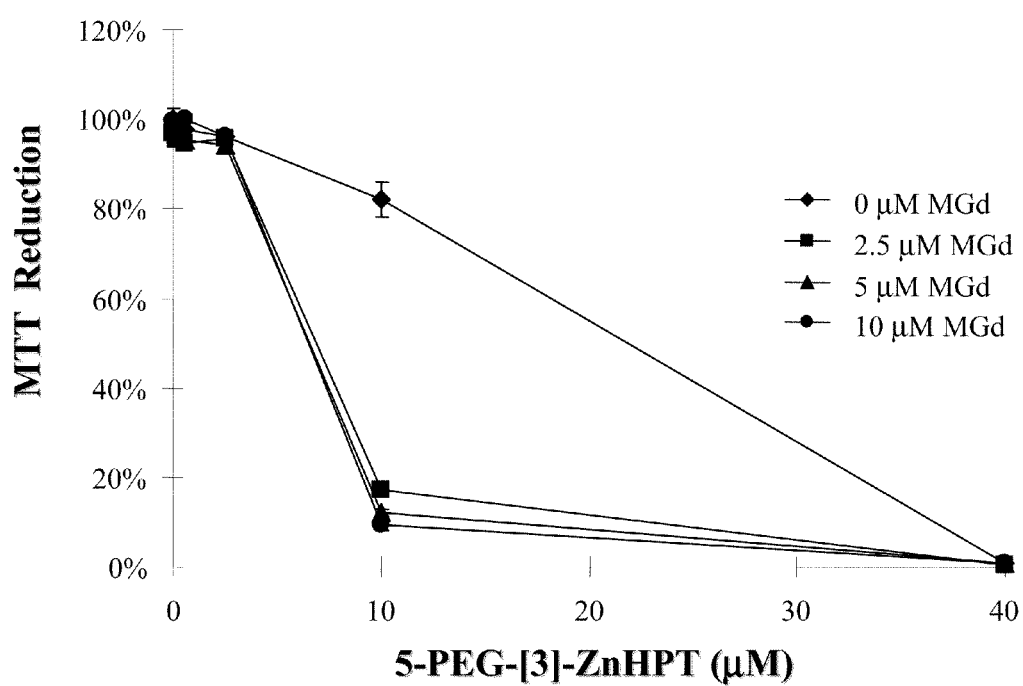
FIG. 26 presents a non-limiting example of 24 h plateau phase cell culture studies with PC3 cells in which MTT reduction is measured as a function of MGd concentration and PEGZnHPT concentration, and in which all studies were done in the presence of 25 µM of $Zn^{2+}$.

FIGS. 2 and 3 show non-limiting schemes to synthesize 5-PEG-[1]-ZnHPT, 5-PEG-[2]-ZnHPT, and 5-PEG-[3]-ZnHPT. 5-PEG-[3]-ZnHPT is also designated as PEGZnHPT in the following examples. Generally, to a refluxing mixture of 2-bromo-methyl-pyridine (5 g, 29 mmol) in a biphasic medium of DCM (500 ml) and water (500 ml) was added $Br_2$ (1.65 ml, 31.9 mmol). The mixture was illuminated using a halogen lamp (500 W, distance: 5-10 cm) under reflux for 30 min. The solution was cooled to room temperature and neutralized with a 10% $Na_2CO_3$ aqueous solution and solid NaCl was added. The aqueous layer was extracted three times with DCM, the combined organic extracts were dried over $MgSO_4$ and evaporated in vacuo. HPLC analysis of the crude product showed the relative ratio of 13.6:76.5:9.9 (Retention time: 8.1, 10.6 and 13.4 min, respectively) for starting material 2-bromo-methyl-pyridine:2-bromo-5-(bromomethyl)pyridine:2-bromo-5-(dibromomethyl)pyridine.

General method for preparations of lithium polyethyleneglycol (PEG) methyl ether 2a-c: Lithium wire (19.2 mmol, 1.2 equiv.) was added to a solution of polyethyleneglycol methyl ether (16 mmol, 1 equiv.) in 5 ml of dry THF under argon and was stirred at 40-50 ° C. overnight for 2-(2-methoxyethoxy) ethanol (n=1) and 2-[2-(2-methoxyethoxy)ethoxy]ethanol (n=2); or was stirred at room temperature for 3-5 hours for 2-methoxyethanol (n=0) to give a light yellow solutions 2a-c. These products were directly used to form compounds 3a-c in the next step.

General method for preparation of 2-bromo-5-(PEG methyl ether)-pyridine 3a-c. 2-bromo-5-(bromomethyl)pyridine 1 in 5 ml dry THF was added to the solutions of 2a-c at 0° C. under argon and stirred at room temperature overnight. The reactions were monitored by HPLC. After the reaction was completed, 2 ml of MeOH-AcOH (1:1) was added to quench the reaction and the resulting solution was extracted with DCM (3×30 ml). The collected DCM phase was washed twice with $H_2O$ and dried over $Mg_2SO_4$ overnight. Purification by chromatography on silica with DCM containing MeOH (0.5~2.0%) as an eluant following evaporation solvent gave the products 3a-c as sticky oils. 2-bromo-5-((2-methoxyethoxy)methyl)pyridine 3a was obtained over two steps. CI-MS: m/z 246 (M)$^+$; CI-HRMS [M]$^+$ calcd. for $C_9H_{13}BrNO_2$: 246.0130 found: 246.0131. $\delta_H$ (400 Hz, $CDCl_3$): 8.27 (s, 1H), 7.52 (d, J=8.0 Hz, 1H), 7.41 (d, J=8.4 Hz, 1H), 4.49 (s, 2H), 3.60-3.58 (m, 2H), 3.53-3.51 (m, 2H), 3.33 (s, 3H). $\delta_C$ (75 Hz, $CDCl_3$): 149.1, 141.0, 137.9, 133.0, 127.7, 71.7, 69.8, 69.7 and 58.9. 2-bromo-5-((2-(2-methoxyethoxy)ethoxy)methyl)pyridine 3b over two steps. CI-MS: m/z 290 (M)$^+$; CI-HRMS [M]$^+$ calcd. for $C_{11}H_{17}BrNO_3$: 290.0389 found: 290.0392. $\delta_H$ (400 Hz, $CDCl_3$): 8.28 (s, 1H), 7.53 (d, J=8.0 Hz, 1H), 7.41 (d, J=8.4 Hz, 1H), 4.50 (s, 2H), 3.64-3.63 (m, 4H), 3.61-3.59 (m, 2H), 3.51-3.49 (m, 2H), 3.33 (s, 3H). $\delta_C$ (75 Hz, $CDCl_3$): 149.1, 141.0, 137.9, 133.0, 127.7, 71.7, 70.4(2), 70.4(1), 69.8, 69.7 and 58.9. 2-bromo-5-((2-(2-(2-methoxyethoxy)ethoxy)ethoxy)methyl)pyridine 3c over two steps. CI-MS: m/z 334 (M+H)$^+$; CI-HRMS [M+H]$^+$ calcd. for $C_{13}H_{21}BrNO_4$: 334.0654 found:

334.0656. $\delta_H$ (400 Hz, CDCl$_3$): 8.28 (s, 1H), 7.53 (d, J=8.0 Hz, 1H), 7.42 (d, J=8.4 Hz, 1H), 4.50 (s, 2H), 3.64-3.59 (m, 10H), 3.52-3.49 (m, 2H), 3.33 (s, 3H). $\delta_C$ (75 Hz, CDCl$_3$): 149.3, 141.2, 138.0, 133.2, 127.8, 71.9, 70.6, 70.5(4), 70.4(6), 69.9, 69.8 and 59.0.

General method for preparation of 2-bromo-5-(PEG methyl ether)-pyridine-N-oxide 4a-c. A solution of 3a-c (1 equiv.) and 3-chloroperoxybenzoic acid (77% maximum, m-CPBA, 2.5-3.5 equiv.) in CHCl$_3$ (5 ml per 1 mmol 3a-c) was heated to 40° C. and stirred for 30-60 minutes under argon, monitoring reaction by HPLC. After the reaction was complete, the mixture was evaporated to a light yellow solid. The solid was dissolved in MeOH and added H$_2$O until it became a suspension. The suspension was loaded on tC18 column and eluted with 25-35% MeOH—H$_2$O. All of the fractions were combined, partitioned between DCM and aq. NaCl and extracted three times. The combined solvent extracts were washed once with 10% Na$_2$CO$_3$ and once with water. The solution was dried over Mg$_2$SO$_4$ for 3 hours and evaporated to give yellow sticky oil products 4a-c. 2-bromo-5-((2-methoxyethoxy)methyl)pyridine-N-oxide 4a was obtained. CI-MS: m/z 262 (M)$^+$. $\delta_H$(400 Hz, CDCl$_3$): 8.35 (s, 1H), 7.56 (d, J=8.0 Hz, 1H), 7.04 (d, J=8.4 Hz, 1H), 4.46 (s, 2H), 3.62-3.60 (m, 2H), 3.54-3.51 (m, 2H), 3.33 (s, 3H). $\delta_C$ (75 Hz, CDCl$_3$): 138.8, 136.6, 131.1, 130.0, 124.6, 71.5, 69.9, 68.8 and 58.8. 2-bromo-5-((2-(2-methoxyethoxy)ethoxy)methyl)pyridine-N-oxide 4b was obtained. CI-MS: m/z 306 (M)'; CI-HRMS [M]$^+$ calcd. for C$_{11}$H$_{17}$BrNO$_4$: 306.0341 found: 306.0340. $\delta_H$ (400 Hz, CDCl$_3$): 8.29 (s, 1H), 7.51 (d, J=8.8 Hz, 1H), 6.99 (d, J=8.8 Hz, 1H), 4.41 (s, 2H), 3.57-3.56 (m, 4H), 3.54-3.52 (m, 2H), 3.45-3.43 (m, 2H), 3.26 (s, 3H). $\delta_C$ (75 Hz, CDCl$_3$): 138.8, 136.7, 131.2, 130.0, 124.8, 71.6, 70.3, 70.2(7), 70.0, 68.8 and 58.8. 2-bromo-5-((2-(2-(2-methoxyethoxy)ethoxy)methyl)pyridine-N-oxide 4c was obtained. CI-MS: m/z 350 (M+H)$^+$. $\delta_H$ (400 Hz, CDCl$_3$): 8.33 (s, 1H), 7.55 (d, J=11.2 Hz, 1H), 7.04 (d, J=10.8 Hz, 1H), 4.45(s, 2H), 3.62-3.56 (m, 10H), 3.49-3.40 (m, 2H), 3.30 (s, 3H). $\delta_C$ (75 Hz, CDCl$_3$): 139.8, 136.8, 131.2, 130.2, 124.7, 71.8, 70.4(4) broad, 70.4, 70.1, 68.9 and 58.9.

General method for preparations of 2-thiol-5-(PEG methyl ether)-pyridine-N-oxide 5a-c. A solution of 4a-c (1 equiv) in H$_2$O (1 mmol/1ml) was heated to 90-100° C. under argon and a solution of sodium sulfide (2 equiv) and trace 0.1 M NaOH aq. (1.0-1.3% equiv) in H$_2$O (1 mmol/1 ml) was added dropwise over 1 hour and the resulting solution was stirred for another 1-3 hours. The reaction was monitored with HPLC. After the reaction was complete, the yellow solution was acidified to pH=1-2 with 1 M HCl. The produced H$_2$S gas was removed with water aspirator for 5-10 min. To the suspension, solid NaCl was added and the resulting solution was extracted three times with DCM. The crude product was loaded on a tC18 column and eluted with 25-35% MeOH—H$_2$O. All of the eluted fractions were combined, partitioned between DCM and aq. NaCl and extracted three times. The organic layer was dried over Mg$_2$SO$_4$ for 3 hours and evaporated to give the yellow sticky oil product 5a-c. 2-thiol-5-((2-methoxyethoxy)methyl)pyridine-N-oxide 5a was obtained. CI-MS: m/z 216 (M)$^+$. CI-HRMS [M]$^+$ calcd. for C$_9$H$_{14}$NO$_3$S: 216.0694 found: 216.0694. $\delta_H$ (400 Hz, CDCl$_3$): 8.10 (s, 1H), 7.60 (d, J=11.6 Hz, 1H), 7.21 (dd, J=8.4, J=2.0 Hz, 1H), 4.44 (s, 2H), 3.65-3.62 (m, 2H), 3.57-3.53 (m, 2H), 3.36 (s, 3H). $\delta_C$ (75 Hz, CDCl$_3$): 165.6, 132.1, 131.5, 129.9, 125.7, 71.7, 69.9, 68.9 and 60.0. 2-thiol -5-((2-(2-methoxyethoxy)ethoxy)methyl)pyridine-N-oxide 5b was obtained. CI-MS: m/z 260 (M)$^+$; CI-HRMS [M]$^+$ calcd. for C$_{11}$H$_{18}$ NO$_4$S: 260.0957; found: 260.0957. $\delta_H$ (400 Hz, CDCl$_3$): 8.12 (s, 1H), 7.58 (d, J=8.4 Hz, 1H), 7.19 (d, J=8.8 Hz, 1H), 4.53 (s, 2H), 3.66-3.65 (m, 4H), 3.62-3.60 (m, 2H), 3.54-3.51 (m, 2H), 3.35 (s, 3H). $\delta_C$ (75 Hz, CDCl$_3$): 165.7, 132.1, 131.5, 130.0, 125.9, 71.8, 70.5, 69.9, 68.9 and 59.0. 2-thiol-5-((2-(2-(2-methoxyethoxy)ethoxy)ethoxy) methyl) pyridine-N-oxide 5c was obtained in over two steps. CI-MS: m/z 304 (M+H)$^+$. $\delta_H$ (400 Hz, CDCl$_3$): 8.12 (s, 1H), 7.57 (d, J=8.4 Hz, 1H), 7.18 (d, J=8.4 Hz, 1H), 4.43(s, 2H), 3.63-3.59 (m, 10H), 3.50-3.48 (m, 4H), 3.31 (s, 3H). $\delta_C$ (75 Hz, CDCl$_3$): 165.7, 132.1, 131.4, 130.0, 125.9, 71.8, 70.6, 70.5, 70.4, 68.9 and 59.0.

General method for preparation of the zinc complexes of 2-thiol-5-(PEG methyl ether)-pyridine-N-oxide 6a-c. A mixture of 5a-c (1 equiv) and 0.1 N NaOH (0.5 equiv) were dissolved MeOH (MeOH is not necessary for 5c). Zn(OAc).2H$_2$O (1 equiv) was added and the solution was heated to 90-100° C. and stirred under argon. Over 2 hours another 0.5 equiv of 0.1 N NaOH was added. The reaction required another 3-5 hours for completion, and was thereupon cooled to room temperature. The crude zinc complex was extracted 3 times with DCM and dried under reduced pressure. The crude product was dissolved in a mixture of MeOH and H$_2$O at a ratio of 1:2-3, loaded on a tC18 column, and eluted with 30-45% MeOH—H$_2$O. All of the fractions containing product were combined and was extracted three times with DCM. The solution was next dried over Mg$_2$SO$_4$ for 3 hours. The white solid 6a and dark gray sticky oily products 6b, 6c were obtained after filtering and drying. Compound 6a was characterized by X-ray single crystal analysis. The crystal was grown in DCM-hexane. 2-thiol-5-((2-methoxyethoxy)methyl)pyridine-N-oxide, Zn complex, 6a was obtained. CI-MS: m/z 493 (M+1)$^-$. CI-HRMS [M+1]$^+$ calcd. for C$_{18}$H$_{25}$N$_2$O$_6$S$_2$Zn: 493.0446 found: 493.0446. $\delta_H$ (400 Hz, CDCl$_3$): 8.26 (s, 1H), 7.62 (d, J=8.4 Hz, 1H), 7.18 (dd, J=8.4, J=2.0 Hz, 1H), 4.43 (s, 2H), 3.57-3.55 (m, 2H), 3.51-3.49 (m, 2H), 2H), 3.32 (s, 3H). $\delta_C$ (75 Hz, CDCl$_3$): 158.1, 136.0, 129.6, 129.5, 129.2, 71.7, 69.7, 69.1 and 59.0. 2-thiol -5-((2-(2-methoxyethoxy)methyl)pyridine-N-oxide, Zn complex, 6b. CI-MS: m/z 581 (M+1)$^+$; TOF-HRMS [M]$^+$ calcd. For C$_{22}$H$_{33}$N$_2$O$_8$S$_2$Zn: 581.0967; found: 581.0966. $\delta_H$ (400 Hz, CDCl$_3$): 8.29 (s, 1H), 7.65 (d, J=8.4 Hz, 1H), 7.20 (dd, J=8.4, J=2.0 Hz, 1H), 4.46 (s, 2H), 3.63-3.60 (m, 6H), 3.53-3.51 (m, 2H), 3.35 (s, 3H). $\delta_C$ (75 Hz, CDCl$_3$): 158.2, 136.1, 129.8, 129.6, 129.3, 71.9, 70.6, 70.5, 69.9, 69.2 and 59.0. 2-thiol-5-((2-(2-(2-methoxyethoxy)ethoxy)ethoxy) methyl) pyridine-N-oxide, Zn complex, 6c was obtained in over last two steps. CI-MS: m/z 669 (M+H)$^+$. $\delta_H$ (400 Hz, CDCl$_3$): 8.29 (s, 1H), 7.66 (d, J=11.2 Hz, 1H), 7.21 (dd, J=10.4, 2.0 Hz, 1H), 4.46(s, 2H), 3.65-3.59 (m, 10H), 3.53-3.50 (m, 2H), 3.34 (s, 3H). $\delta_C$ (75 Hz, CDCl$_3$): 158.2, 136.1, 129.8, 129.7, 129.3, 71.8, 71.9, 70.7, 70.6, 70.5, 69.9 and 69.2.

Example 2

Cellular Proliferation and Toxicity Assays

A549 lung cancer and PC3 prostate cancer lines are obtained from the American Type Culture Collection. Cells are cultured in RPMI 1640 medium supplemented with 20 mM HEPES, 2 mM L-glutamine, 10% heat inactivated fetal bovine serum (Hyclone) and antibiotics (200 U/mL penicillin and 200 μg/mL streptomycin).

The proliferation of exponential phase cultures of A549 and PC3 cells is assessed by formazan reduction. In brief, A549 (2000 cells/well) or PC3 (4000 cells/well) cells are seeded on 96-well microtiter plates and allowed to adhere overnight. Stock solutions of ZnHPT or PEGZnHPT in medium are serial diluted in a ratio of 1:4 down the plate. Stock solutions of MGd or $ZnOAc_2$ or 5% mannitol in ACS grade water are added and plates are incubated at 37° C. under a 5% $CO_2$/95% air atmosphere. After 24 hours, medium is replaced with fresh medium. After 2 additional days, medium is exchanged for fresh medium (150 µL/well) supplemented with the tetrazolium dye, 3-(4,5-dimethylthiazol-2-yl)-2,5-diphenyltetrazolium bromide (MTT, Sigma Chemical, 0.5 mg/mL). Plates are incubated at 37° C. and viable cells measured. See, e.g., FIGS. 21, 22, 36-43. Alternatively cellular reduction within plateau phase cultures is measured after 24 hours of treatment as a measure of the cytotoxicity due to treatment. See, e.g., FIGS. 16, 17, 18, 19, 23, 24, 25, 26, 44, 45.

Example 3

Lipoate Reduction Assay

Thioredoxin reductase activity is assessed by measuring the rate of lipoate reduction. In brief, A549 or PC3 cells (10,000 cells/well) are plated on 96-well plates and allowed to adhere overnight and grow two additional days until confluent. Cells are treated with ZnHPT, PEGZnHPT, MGd, zinc, or 5% mannitol as above for 4 hours. Medium is removed, cells are washed with Hanks Balanced Salt Solution (HBSS), and a solution of 5 mM lipoic acid and 1 mM 5,5'-dithiobis(2-nitrobenzoic acid) in HBSS (100 µL/well) is added. Plates are incubated at ambient temperature in the dark. At chosen time intervals, plate absorbance is measured at 405-650 nm. Plate absorbances are normalized to wells containing neither exogenous zinc nor texaphyrin complex to allow plate-to-plate comparison. See, e.g., FIGS. 32-35.

Example 4

Intracellular Free Zinc and Cell Viabillity

Figure 27:
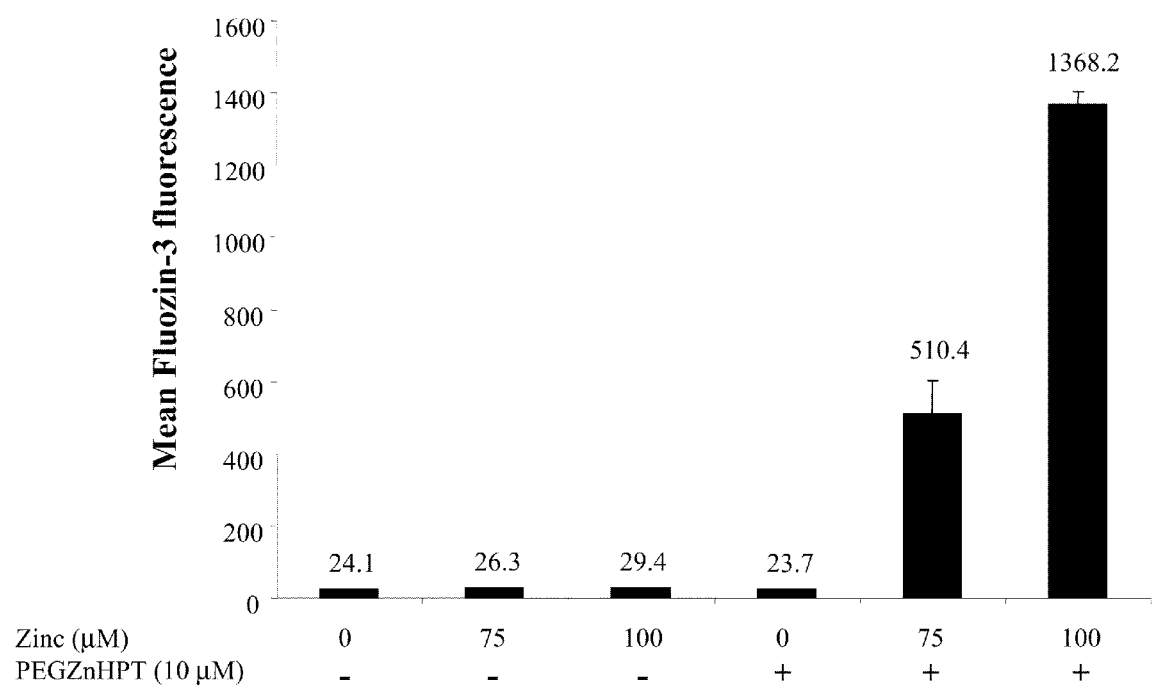
FIG. 27 presents a non-limiting example of the mean fluorescence of Fluozin-3 observed in 4 h plateau phase cell culture with A549 cells as a function of zinc concentration and PEGZnHPT concentration.

The concentration of intracellular free zinc is assessed using the ion-specific fluorescent probe, FluoZin-3-AM™ (FluoZin-3, Molecular Probes, Inc.). Exponential phase cultures are treated with control 5% mannitol vehicle or $ZnOAc_2$ in the presence or absence of PEGZnHPT or ZnHPT for 4 hours. Following treatment, cells are isolated by centrifugation. Cell pellets are washed and re-suspended in a solution of 0.5% BSA in PBS. An aliquot of $10^6$ cells (200 µL) is removed, centrifuged, and treated with FluoZin-3 reaction buffer An aliquot of the cell suspension is supplemented with 2 µg/mL propidium iodide (Sigma Biochemical), incubated for 5 minutes, and subjected to two-parameter flow cytometric analysis. See, e.g., FIG. 27.

Example 5

Using a standard tetrazolide reduction assay, treatment of cancer cells with ZnHPT, formed in situ from HPT and zinc, inhibits proliferation in a dose dependent manner in cell lines including A549 lung, PC3 prostate, K1 and E89 Chinese hamster ovary (CHO), Ramos, DHL-4, and HF-1 B-cell lymphoma. MGd potentiates this effect at an apparent half-maximal concentration of about 2.5 µM-about 5 µM MGd.

Example 6

3-PEG-ZnHPT has an enhanced water solubility ≧about 3 mg/mL. The anti-proliferative activity of 3-PEG-ZnHPT and ZnHPT were compared in vitro, and 3-PEG-ZnHPT displays an apparent activity approximately 10-fold lower than that of ZnHPT.

Example 7

Xenograft Mouse Model

Human cell lines (A549 lung carcinoma, PC3 and DU145 prostatic carcinoma, and potentially others) were used. Mice received XRT (whole body radiation) up to 2 days prior to inoculation to minimize tumor regression due to residual immunological systems. The animal was administered a sublethal dose of whole body radiation of up to 4.5 Gy. The published literature indicates the $LD_{50/30}$ dose for whole body radiation in the mouse to be 6.2 Gy. At the time of tumor implantation, mice were anesthetized by isoflurane inhalation or by IP injection of a ketamine/xylazine cocktail. Using vernier calipers, tumor size was measured; and tumor volume calculated on day 0 of study, at a minimum of 2-3 times/week and immediately prior to scheduled sacrifice. The tumor volume was estimated using the formula for a prolate ellipsoid: $V=[(length)\times(width)^2]/2$ or hemi-ellipsoid: $V=\pi/6\times(length)\times(width)\times(height)$. When tumors reached a predetermined tumor volume animals were divided into treatment groups followed by test/control article dosing. Maximum allowable tumor burden prior to sacrifice is a mean surface diameter of 20 mm or not more than 10% of the animal's body weight as described in the NIH tumor burden guidelines for mice.

Example 8

Xenograft Mouse Model Using A549 Cells

Figure 28:
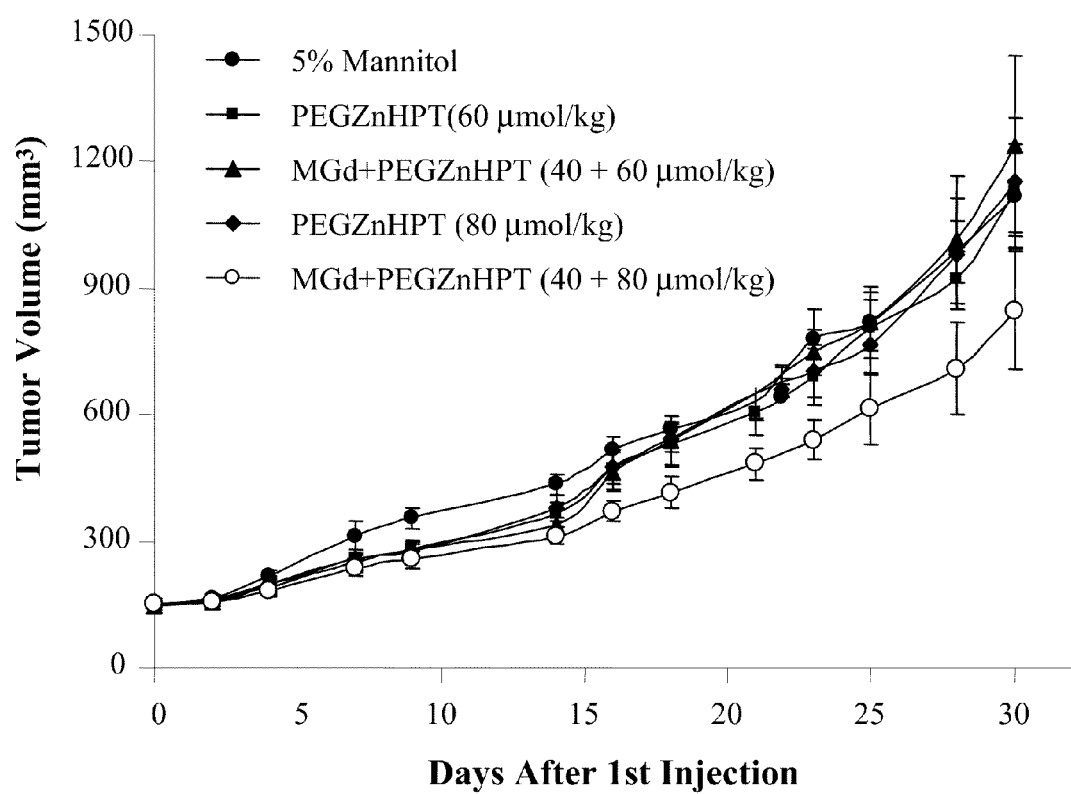
FIG. 28 presents a non-limiting example of the measured tumor volumes in a A549 tumor xenograft model as a function of time following the injection of certain agents.

Using a xenograft mouse model with A549 human lung cancer cells for tumor regrowth, 5-PEG-[3]-ZnHPT shows significant anticancer activity with or without combination with MGd, a known anticancer agent. FIG. 28 shows results from in vivo studies showing the effect of 5-PEG-[3]-ZnHPT alone and MGd+5-PEG-[3]-ZnHPT on tumor regrowth in a A549 xenograft mouse model, where the doses employed are substantially below the maximum tested without evidence of toxicity (i.e., ≧120 µmol/kg).

Example 9

Xenograft Mouse Model Using PC3 Cells

Figure 29:
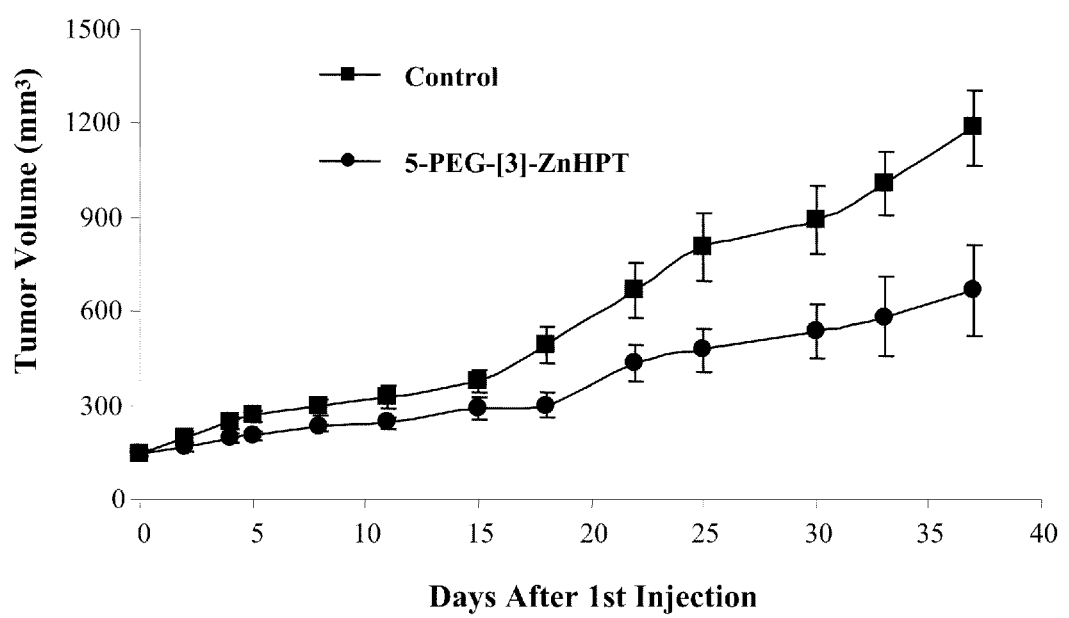
FIG. 29 presents a non-limiting example of the measured tumor volumes in a PC3 tumor xenograft model as a function of time following the injection of certain agents.

Using a xenograft mouse model with PC3 prostate cancer cells for tumor regrowth, PEGZnHPT shows significant anticancer activity. FIG. 29 shows results from in vivo studies showing the effect of 5-PEG-[3]-ZnHPT on tumor regrowth in a PC3 xenograft mouse model, where the doses employed are substantially below the maximum tested without evidence of toxicity (i.e., ≧120 µmol/kg).

Example 10

Xenograft Mouse Model Using PC3 Cells

Figure 30:
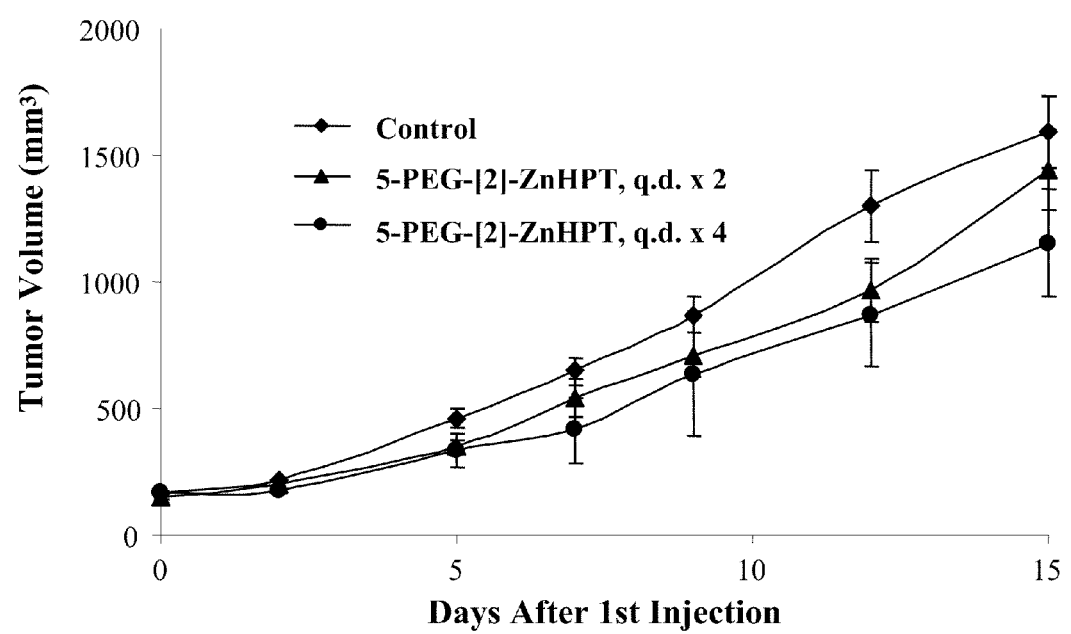
FIG. 30 presents a non-limiting example of the measured tumor volumes in a PC3 tumor xenograft model as a function of time following the injection of certain agents.

Using a xenograft mouse model with PC3 prostate cancer cells for tumor regrowth, 5-PEG-[2]-ZnHPT shows significant anticancer activity as compared to control 5% vehicle. In this example, the ionophore was formulated in 5% mannitol. FIG. 30 shows results from in vivo studies showing the effect of intravenous administration with 5-PEG-[2]-ZnHPT (100 µmol/kg q.d.×2 and 100 µmol/kg q.d.×4) on tumor regrowth in a PC3 xenograft mouse model, where the doses employed are substantially below the maximum tested without evidence of toxicity (i.e., ≧120 μmol/kg).

Example 11

Xenograft Mouse Model Using DU-145 Cells

Figure 31:
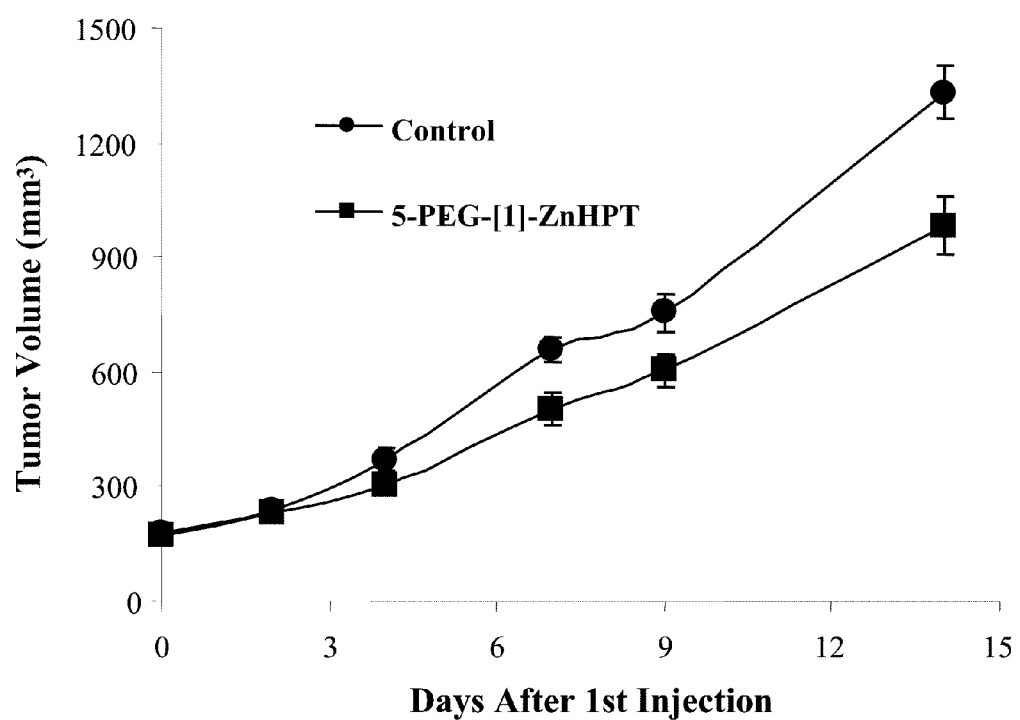
FIG. 31 presents a non-limiting example of the measured tumor volumes in a DU-145 tumor xenograft model as a function of time following the injection of certain agents.
Figure 32:
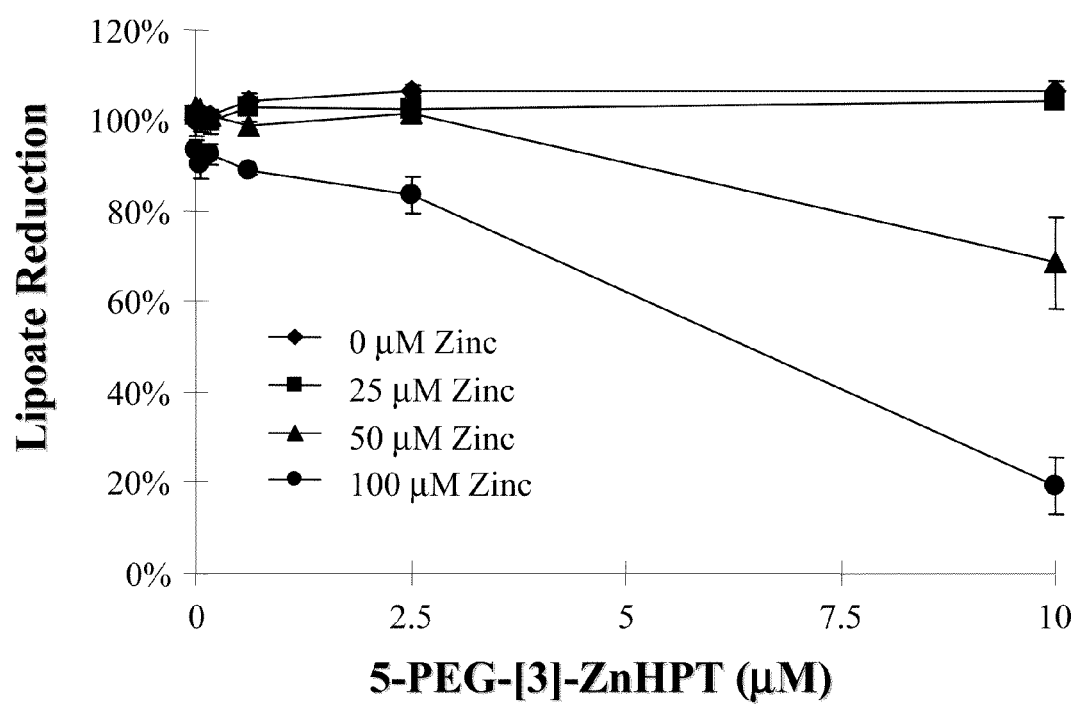
FIG. 32 presents a non-limiting example of 2 h plateau phase cell culture studies with A549 cells in which Lipoate reduction is measured as a function of zinc concentration and 5-PEG-[3]-ZnHPT concentration.
Figure 33:
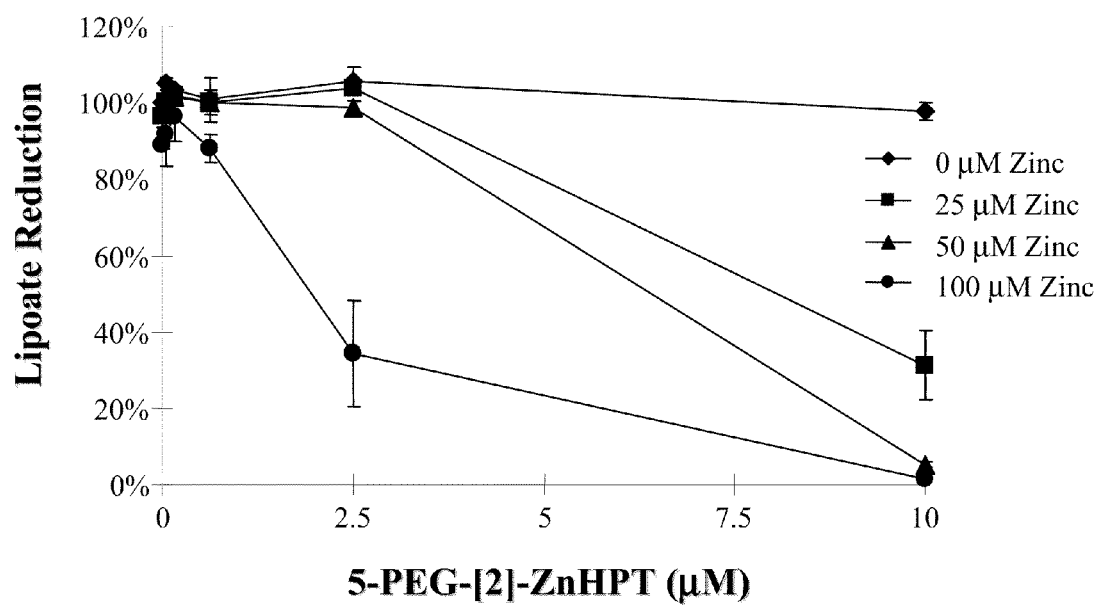
FIG. 33 presents a non-limiting example of 2 h plateau phase cell culture studies with A549 cells in which Lipoate reduction is measured as a function of zinc concentration and 5-PEG-[2]-ZnHPT concentration.
Figure 34:
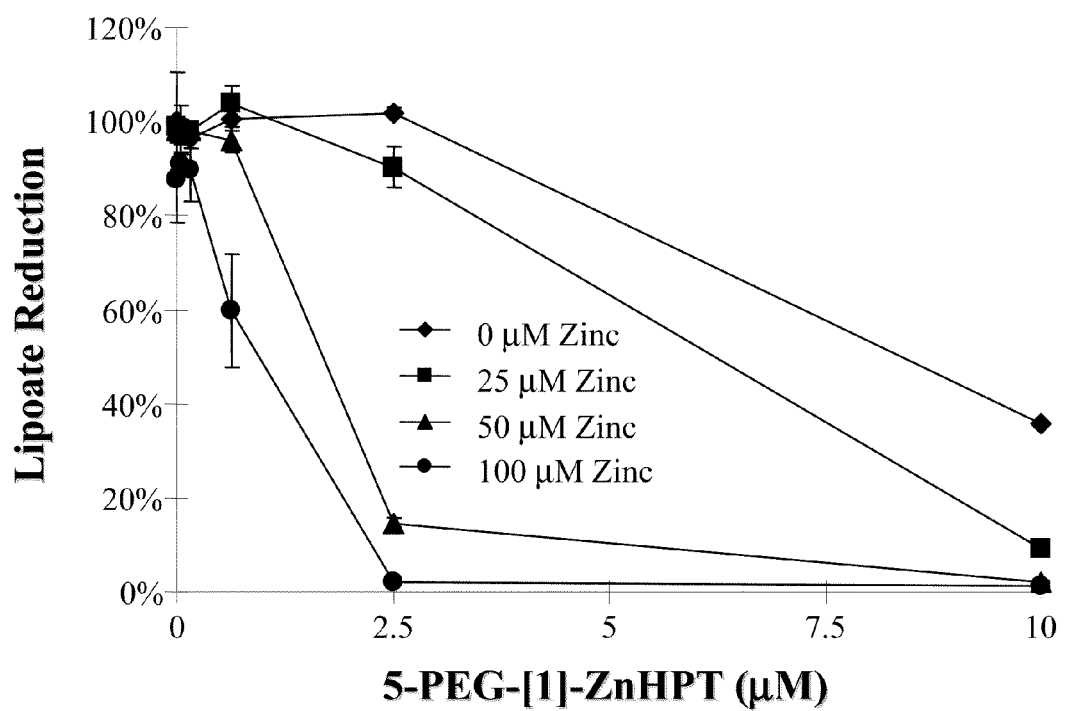
FIG. 34 presents a non-limiting example of 2 h plateau phase cell culture studies with A549 cells in which Lipoate reduction is measured as a function of zinc concentration and 5-PEG-[1]-ZnHPT concentration.
Figure 35:
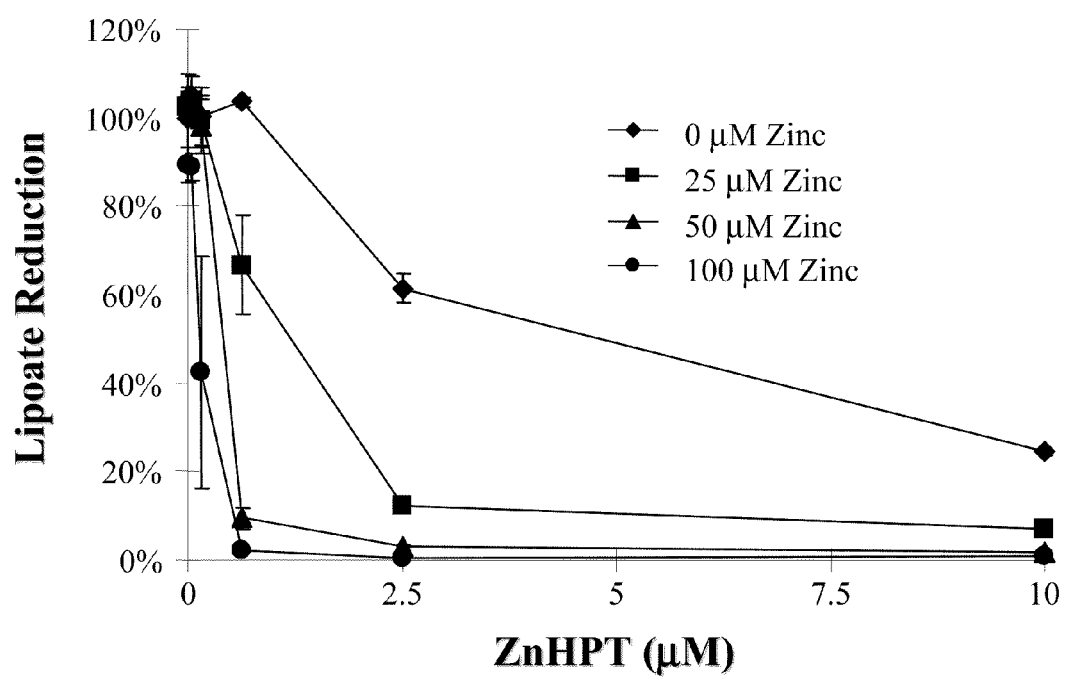
FIG. 35 presents a non-limiting example of 2 h plateau phase cell culture studies with A549 cells in which Lipoate reduction is measured as a function of zinc concentration and ZnHPT concentration.
Figure 36:
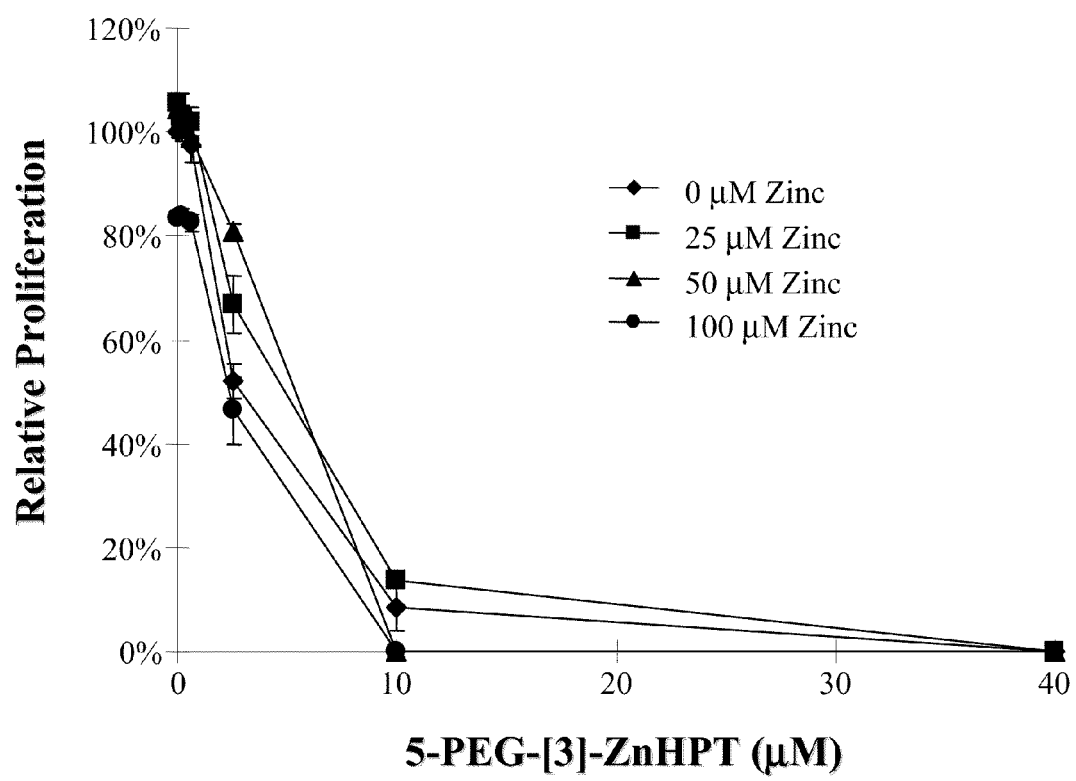
FIG. 36 presents a non-limiting example of 3 day exponential phase cell culture studies with A549 cells in which Relative proliferation is measured as a function of zinc concentration and 5-PEG-[3]-ZnHPT concentration.
Figure 37:
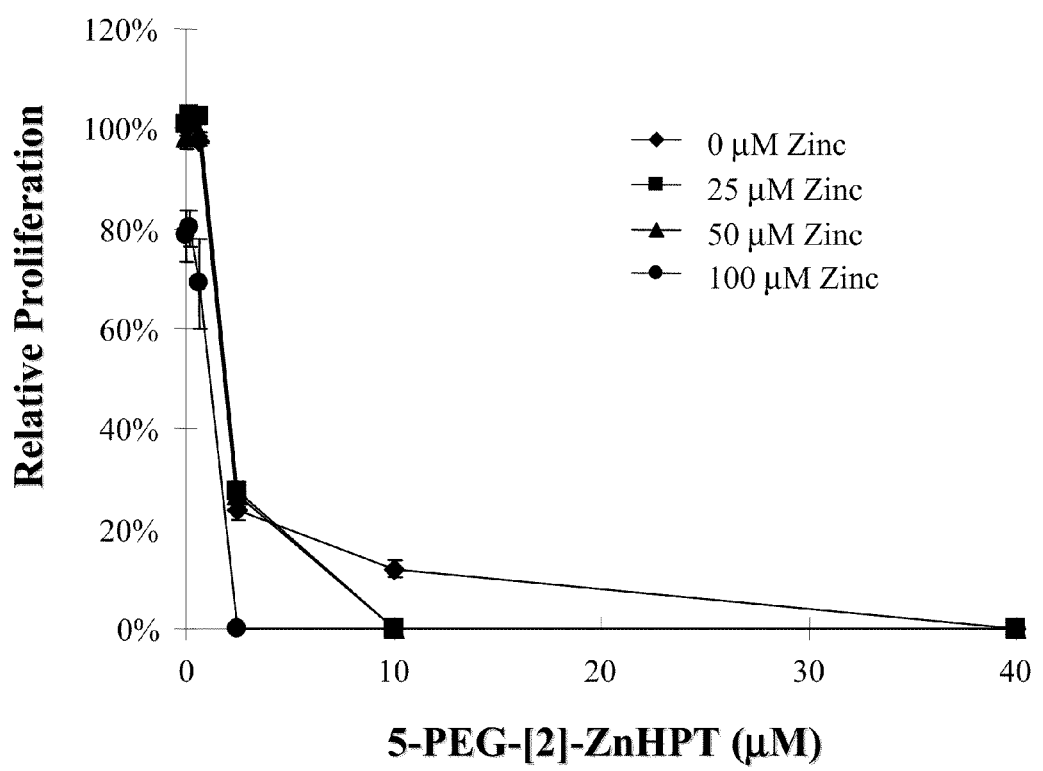
FIG. 37 presents a non-limiting example of 3 day exponential phase cell culture studies with A549 cells in which Relative proliferation is measured as a function of zinc concentration and 5-PEG-[2]-ZnHPT concentration.
Figure 38:
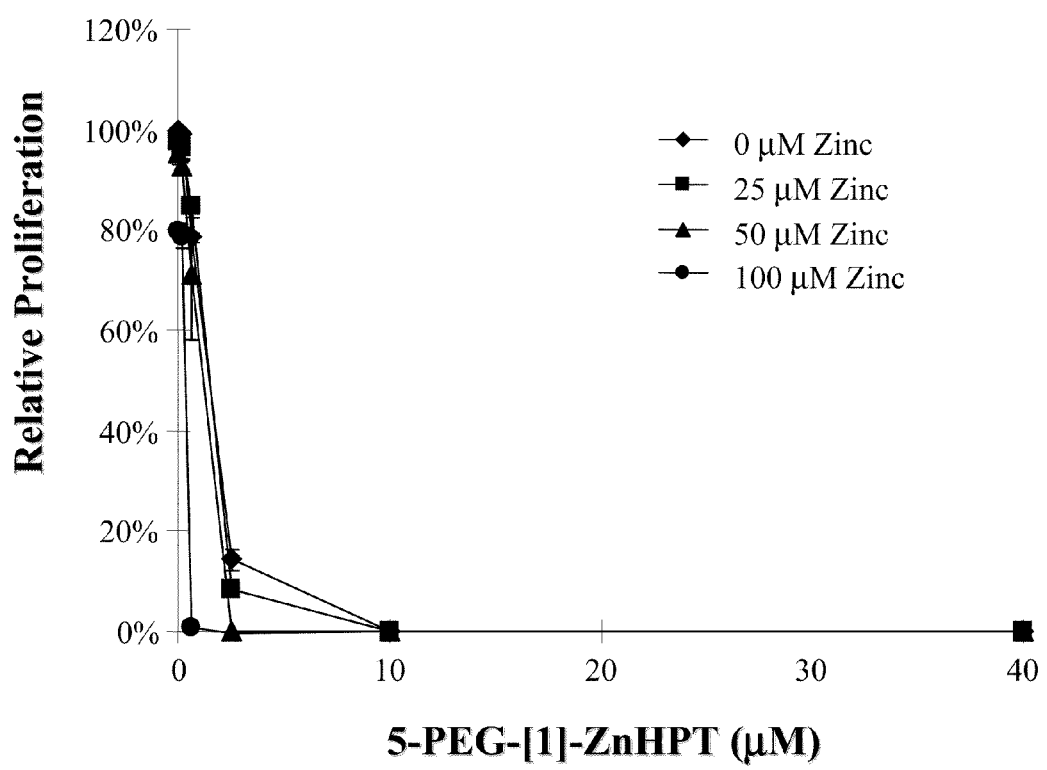
FIG. 38 presents a non-limiting example of 3 day exponential phase cell culture studies with A549 cells in which Relative proliferation is measured as a function of zinc concentration and 5-PEG-[1]-ZnHPT concentration.
Figure 39:
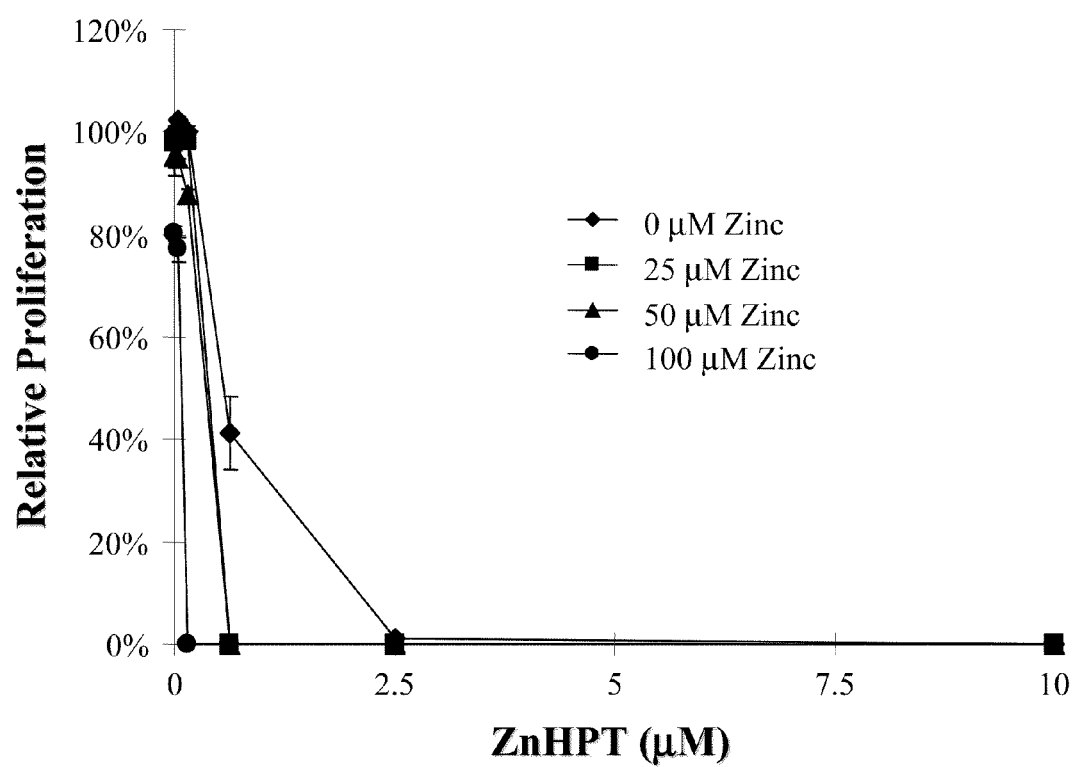
FIG. 39 presents a non-limiting example of 3 day exponential phase cell culture studies with A549 cells in which Relative proliferation is measured as a function of zinc concentration and ZnHPT concentration.
Figure 40:
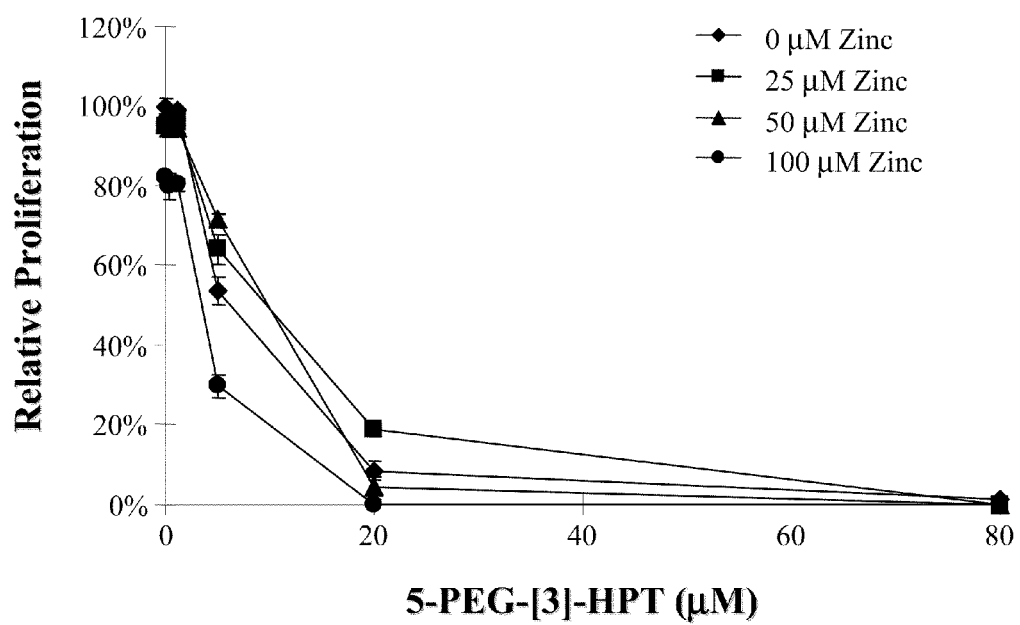
FIG. 40 presents a non-limiting example of 3 day exponential phase cell culture studies with A549 cells in which Relative proliferation is measured as a function of zinc concentration and 5-PEG-[3]-HPT concentration.
Figure 41:
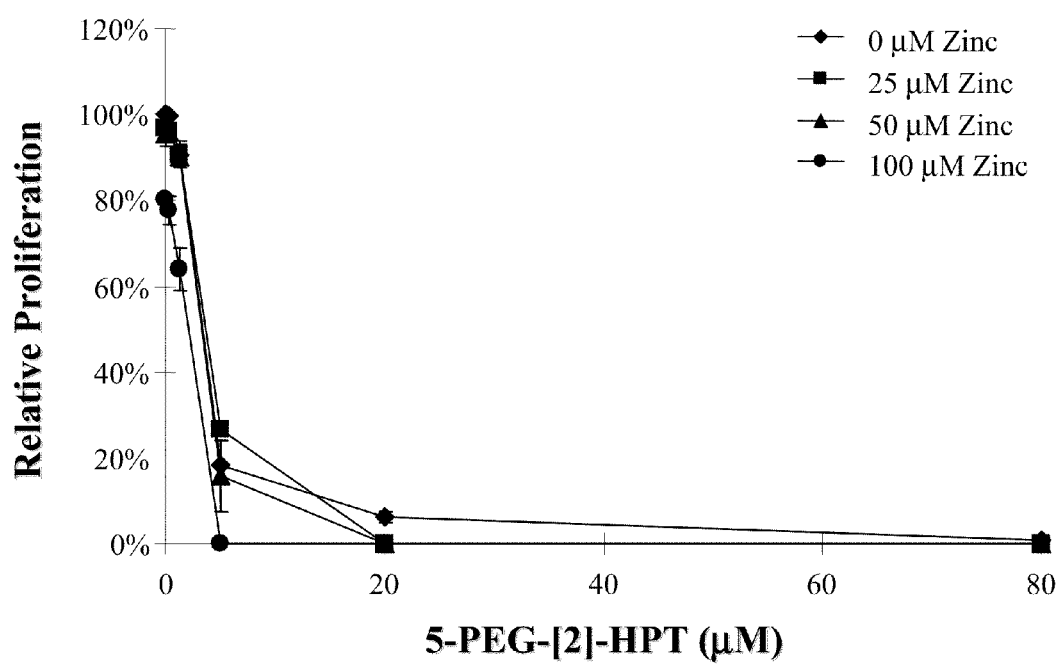
FIG. 41 presents a non-limiting example of 3 day exponential phase cell culture studies with A549 cells in which Relative proliferation is measured as a function of zinc concentration and 5-PEG-[2]-HPT concentration.
Figure 42:
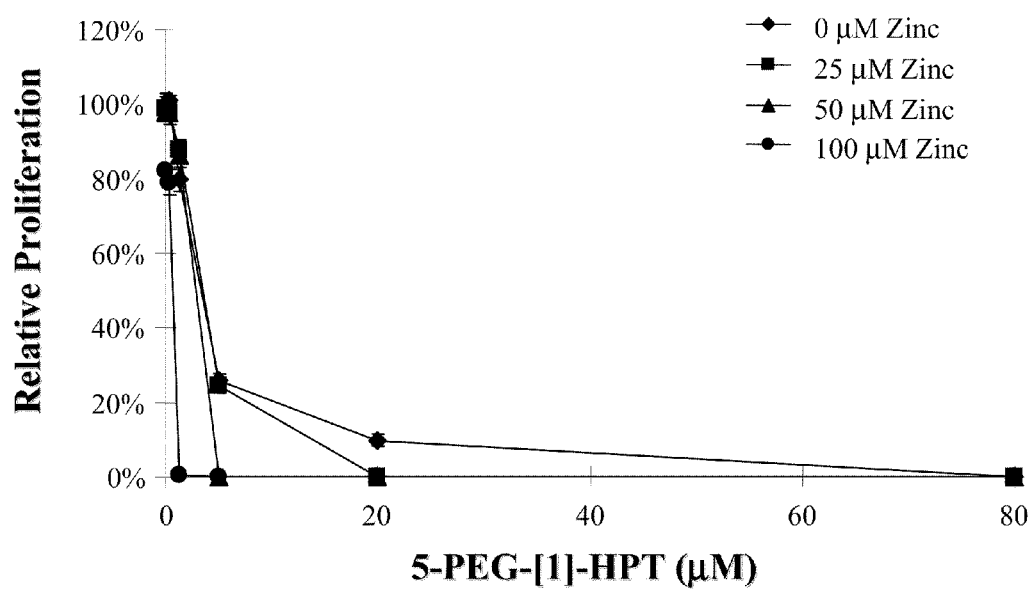
FIG. 42 presents a non-limiting example of 3 day exponential phase cell culture studies with A549 cells in which Relative proliferation is measured as a function of zinc concentration and 5-PEG-[1]-HPT concentration.
Figure 43:
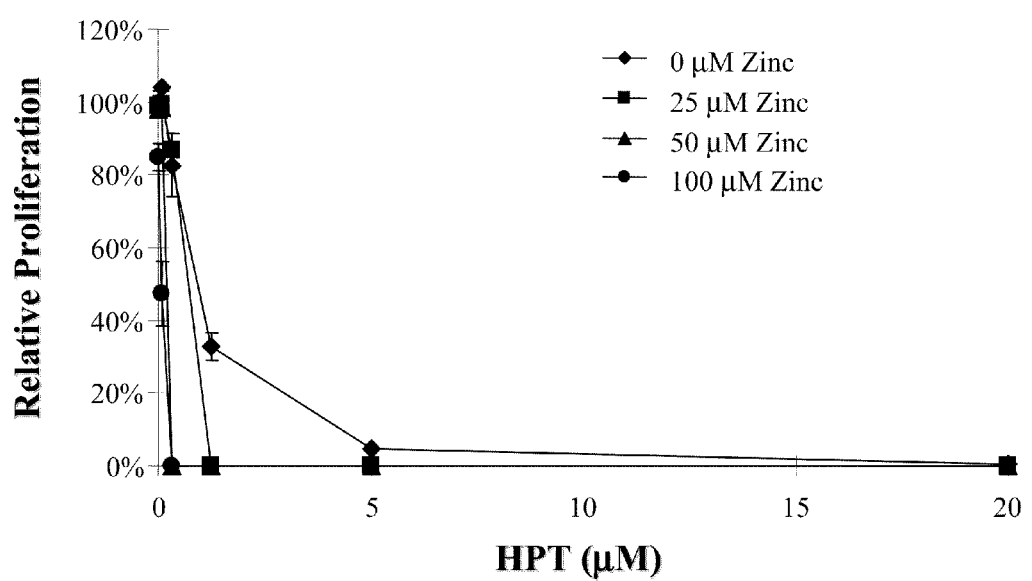
FIG. 43 presents a non-limiting example of 3 day exponential phase cell culture studies with A549 cells in which Relative proliferation is measured as a function of zinc concentration and HPT concentration.
Figure 44:
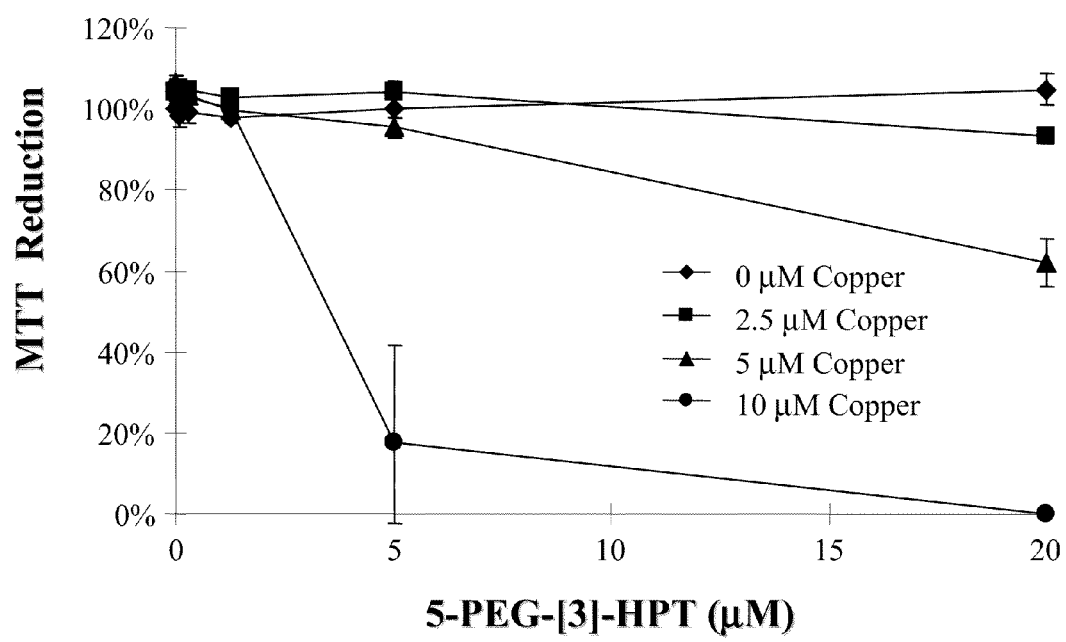
FIG. 44 presents a non-limiting example of 24 h plateau phase cell culture studies with A549 cells in which MTT reduction is measured as a function of copper concentration and 5-PEG-[3]-HPT concentration.
Figure 45:
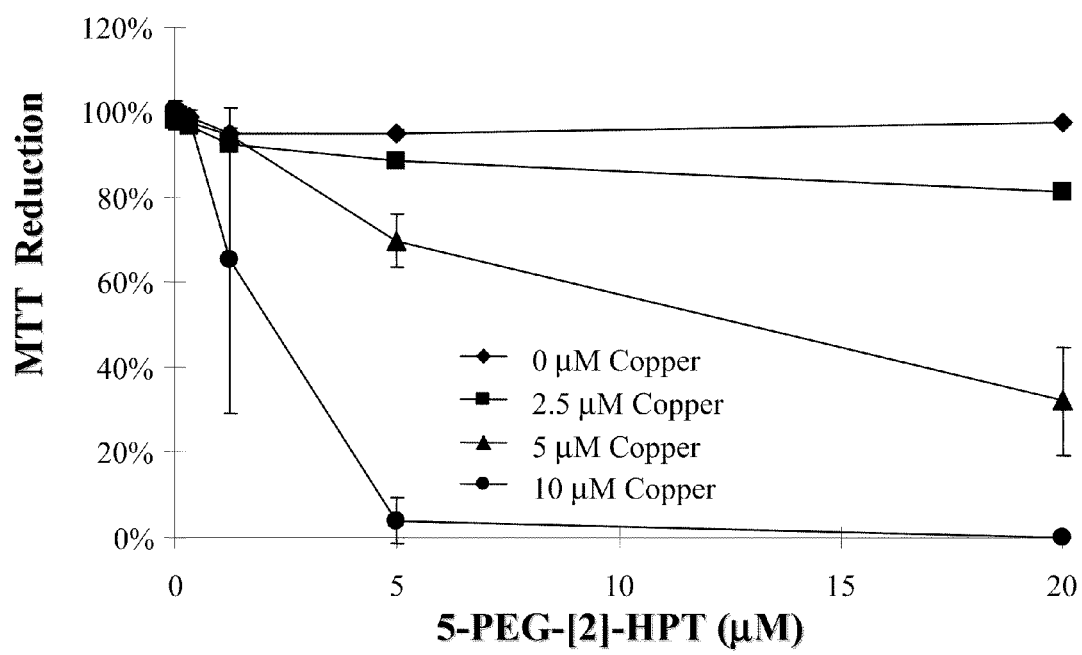
FIG. 45 presents a non-limiting example of 24 h plateau phase cell culture studies with A549 cells in which MTT reduction is measured as a function of copper concentration and 5-PEG-[2]-HPT concentration.
Figure 46:
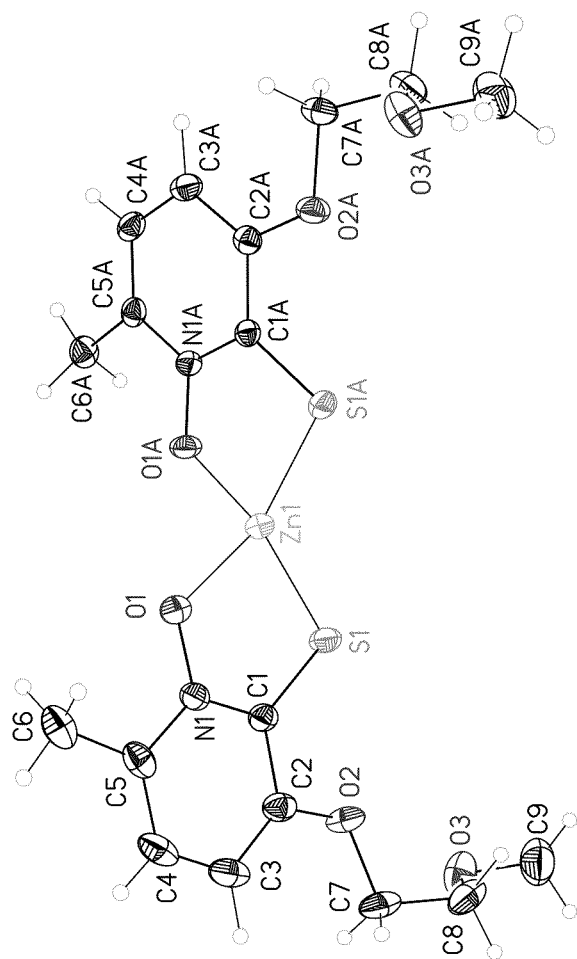
FIG. 46 presents a single crystal X-ray diffraction structure of a complex of compound 33a wherein $R_0$, $=CH_3$ $R_2$, $R_1=H$ and $R_3=OCH_2CH_2OCH_3$.
Figure 47:
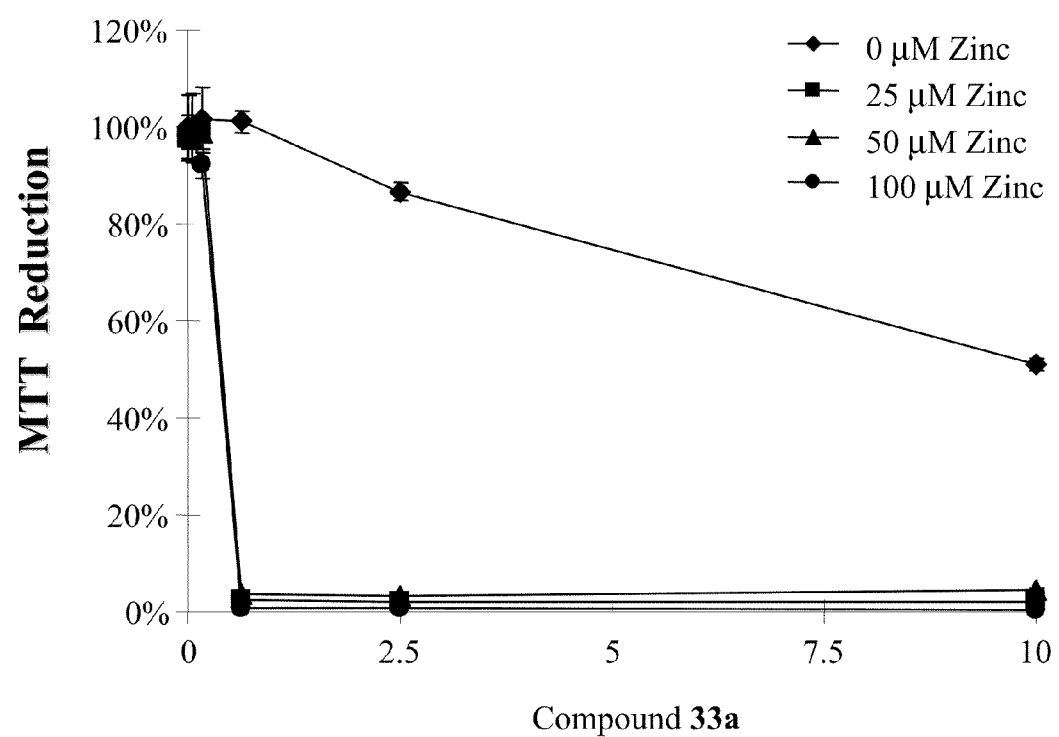
FIG. 47 presents a non-limiting example of 1 day plateau phase cell culture studies with A549 cells in which MTT reduction is measured as a function of zinc concentration and compound 33a concentration.
Figure 48:
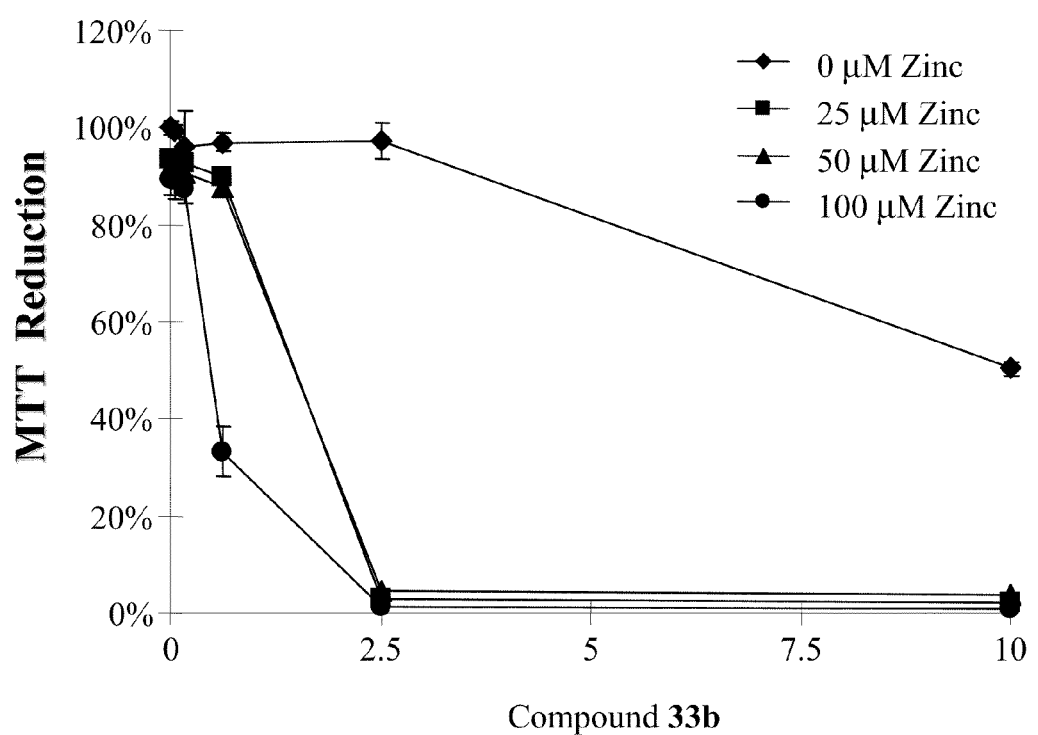
FIG. 48 presents a non-limiting example of 1 day plateau phase cell culture studies with A549 cells in which MTT reduction is measured as a function of zinc concentration and compound 33b concentration.
Figure 49:
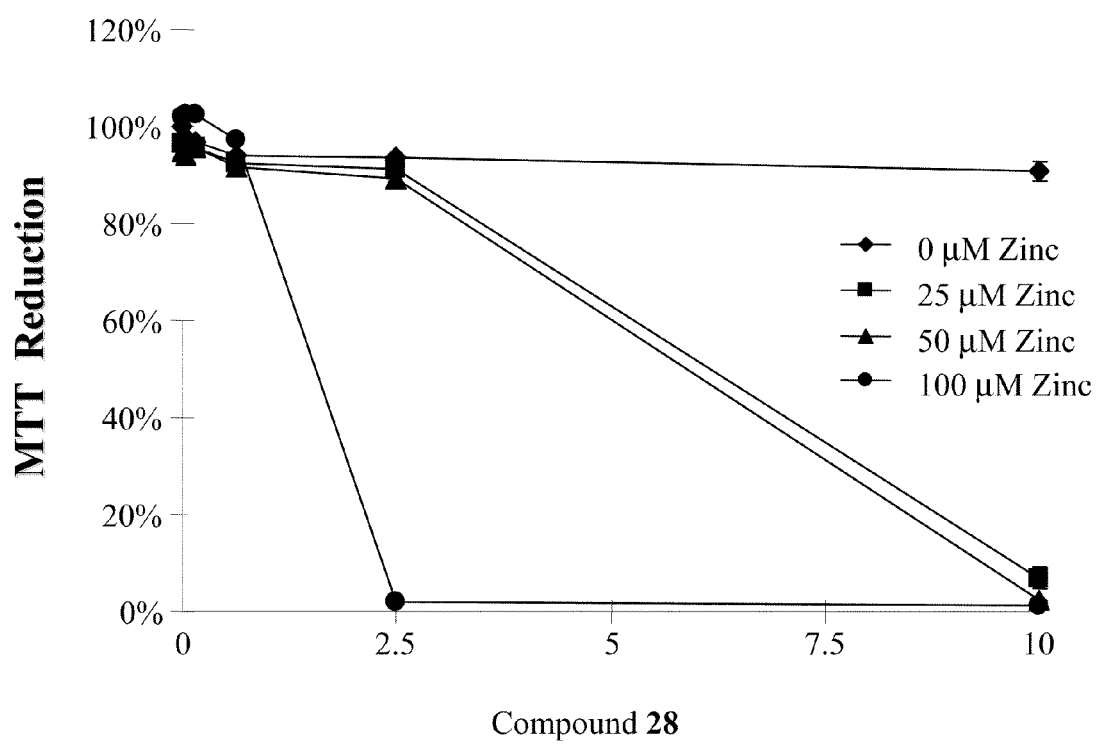
FIG. 49 presents a non-limiting example of 1 day plateau phase cell culture studies with A549 cells in which MTT reduction is measured as a function of zinc concentration and compound 28 concentration.
Figure 50:
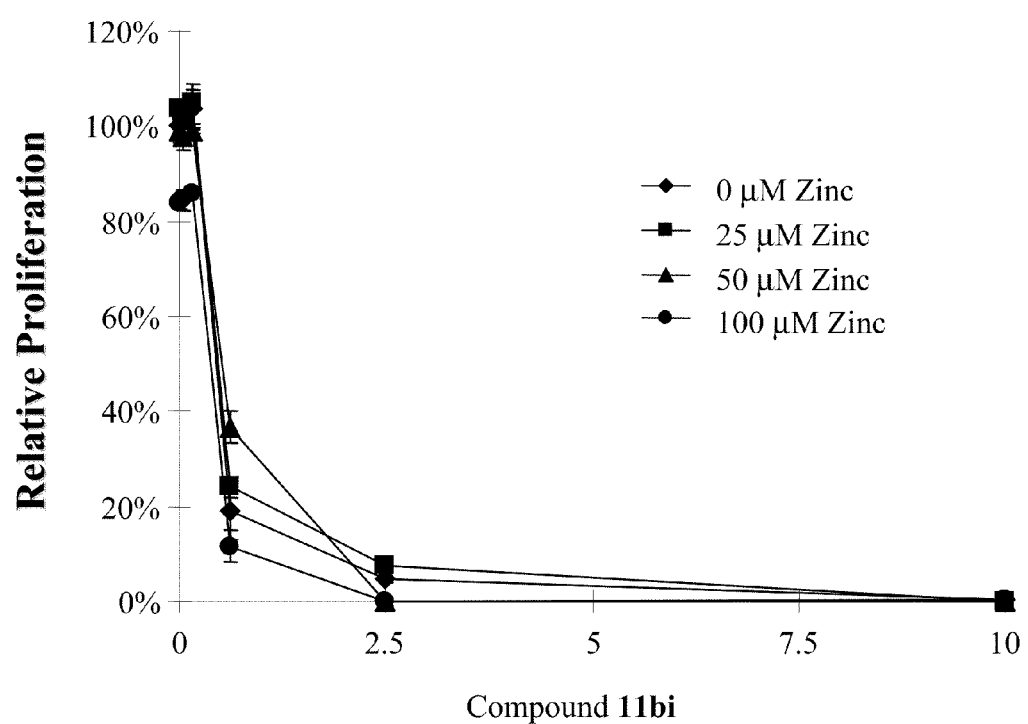
FIG. 50 presents a non-limiting example of 3 day exponential phase cell culture studies with A549 cells in which Relative proliferation is measured as a function of zinc concentration and 11bi concentration.
Figure 51:
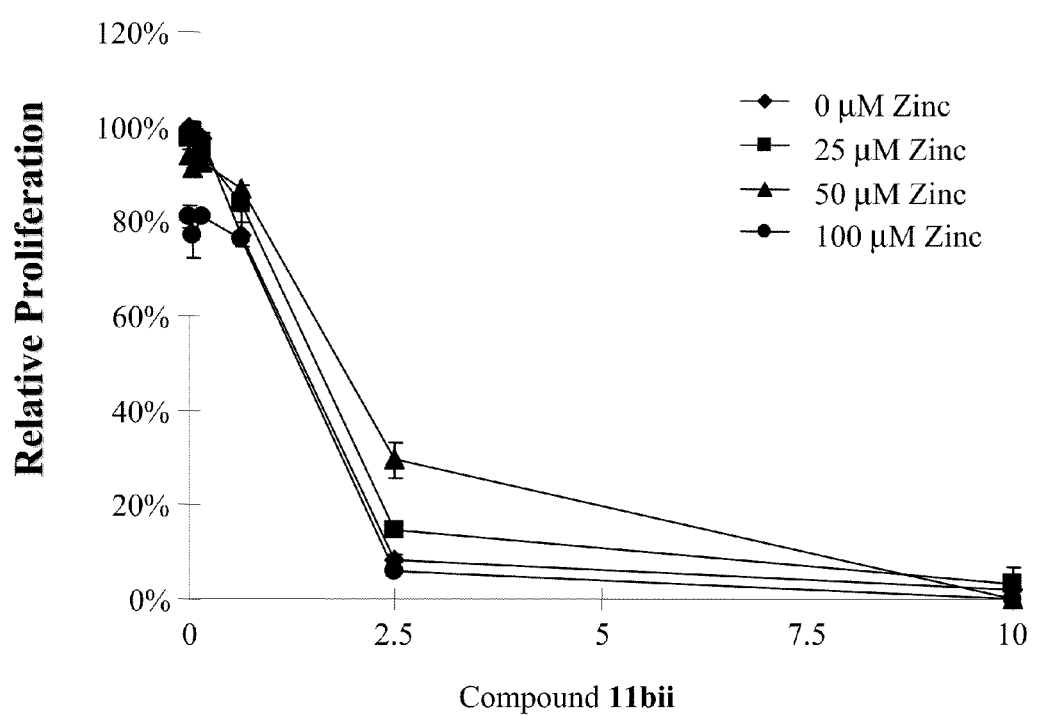
FIG. 51 presents a non-limiting example of 3 day exponential phase cell culture studies with A549 in which Relative proliferation is measured as a function of zinc concentration and 11bii concentration.

Using a xenograft mouse model with DU145 prostate cancer cells for tumor regrowth, 5-PEG-[1]-ZnHPT shows significant anticancer activity as compared to control 5% vehicle. In this example, the ionophore was formulated in 30% THPB-P beta-cyclodextrin vehicle (CTD, Inc., Gainesville, Fla.). FIG. 31 shows results from in vivo studies showing the effect of intravenous administration with 5-PEG-[1]-ZnHPT (60 μmol/kg q.d.×4) on tumor regrowth in a DU145 xenograft mouse model, where the doses employed are substantially below the maximum tested without evidence of toxicity (i.e., ≧100 μmol/kg).

While embodiments have been shown and described herein, it will be obvious to those skilled in the art that such embodiments are provided by way of example only. Numerous variations, changes, and substitutions will now occur to those skilled in the art without departing from what is presently disclosed herein. It should be understood that various alternatives to the embodiments described herein may be employed in practicing the present disclosure. It is intended that the following claims define the scope of what is presently disclosed herein and that methods and structures within the scope of these claims and their equivalents be covered thereby.

What is claimed is:
1. A compound having the structure:

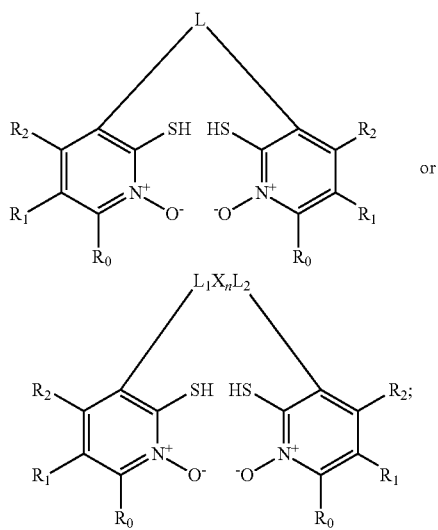

wherein:
  each $R_0$, each $R_1$, and each $R_2$, is independently H, OH, $NH_2$, $NO_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl;
  $L_1$ is —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, or substituted aralkyl;
  X is —O-(alkylene or substituted alkylene)-, or —S(O)$_k$(alkylene or substituted alkylene)-, where k is 1, 2, or 3;
  each n is an integral number selected from 1 to 20; and
  $L_2$ is selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;
  L is selected from the group consisting of alkylene, substituted alkylene, alkenylene, substituted alkenylene, alkynylene, substituted alkynylene, -O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R)C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts.

2. The compound of claim 1 having the structure

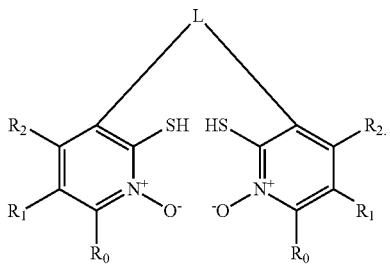

3. The compound of claim 2 wherein each R$_0$, each R$_1$, and each R$_2$ are independently hydrogen.

4. The compound of claim 2 wherein each R$_1$ and each R$_2$ are independently hydrogen and each R$_0$ are independently lower alkyl.

5. The compound of claim 2 wherein L is selected from the group consisting of —O—, —O-(alkylene or substituted alkylene)-, -(alkylene or substituted alkylene)-O-(alkylene or substituted alkylene)-, and —O-(alkylene or substituted alkylene)-O—.

6. The compound of claim 5 wherein L is —O—.

7. The compound of claim 5 wherein L is —O-(alkylene or substituted alkylene)-O—.

8. The compound of claim 7 wherein alkylene is CH$_2$CH$_2$.

9. The compound of claim 1 having the structure

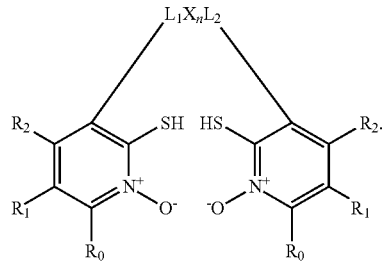

10. The compound of claim 9 wherein each R$_0$, each R$_1$, and each R$_2$ are independently hydrogen.

11. The compound of claim 9 wherein each R$_1$ and each R$_2$ are independently hydrogen and each R$_0$ are independently lower alkyl.

12. The compound of claim 9 wherein L$_1$ is —CON(R')-(alkyl or substituted alkyl), alkyl, substituted alkyl, alkoxy, substituted alkoxy, alkylalkoxy, substituted alkylalkoxy, polyalkylene oxide, or substituted polyalkylene oxide.

13. The compound of claim 12 wherein L$_1$ is O—CH$_2$CH$_2$—.

14. The compound of claim 9 wherein X is —O-(alkylene or substituted alkylene)-.

15. The compound of claim 14 wherein alkylene is CH$_2$CH$_2$.

16. The compound of claim 15 wherein n is 1 to 5.

17. The compound of claim 16 wherein n is 1.

18. The compound of claim 15 wherein n is 2.

19. The compound of claim 16 wherein L$_2$ is a direct bond alkylene, substituted alkylene, —O—, or —C(O)N(R')—.

20. A pharmaceutical composition comprising a compound having the structure:

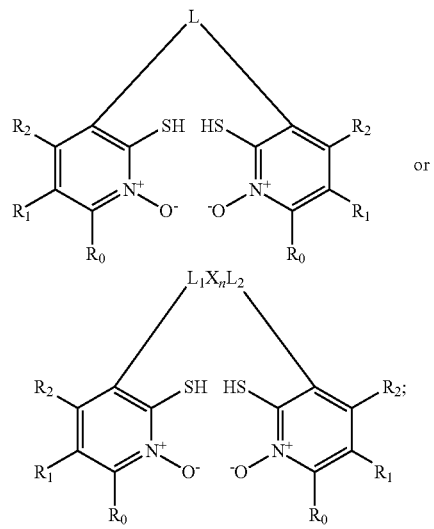

wherein:
each R$_0$, each R$_1$, and each R$_2$, is independently H, OH, NH$_2$, NO$_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl;

L$_1$ is —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, or substituted aralkyl;

X is —O-(alkylene or substituted alkylene)-, or —S(O)$_k$ (alkylene or substituted alkylene)-, where k is 1, 2, or 3;

each n is an integral number selected from 1 to 20; and

L$_2$ is selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C(O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts and a pharmaceutically acceptable excipient thereof.

21. A method of treating cancer comprising administering to a patient in need thereof a therapeutically effective amount of at least one compound having the structure

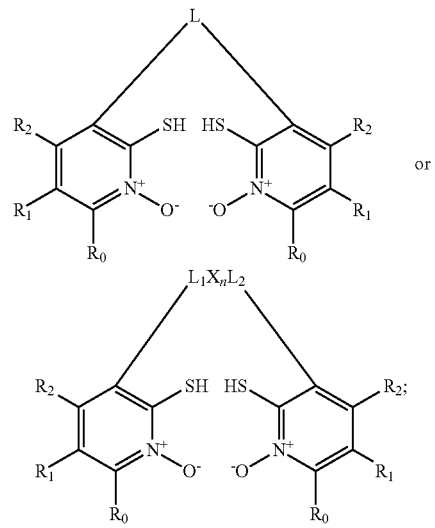

wherein:

each $R_0$, each $R_1$, and each $R_2$, is independently H, OH, NH$_2$, NO$_2$, CN, halogen, lower alkyl, substituted lower alkyl, lower cycloalkyl, substituted lower cycloalkyl, aryl, substituted aryl, heteroaryl, substituted heteroaryl, alkaryl, substituted alkaryl, aralkyl, substituted aralkyl, substituted amino, alkoxy, substituted alkoxy, —S-(alkyl or substituted alkyl), —S(O)$_k$(alkyl or substituted alkyl), where k is 1, 2, or 3, —C(O)-(alkyl or substituted alkyl), —C(O)O-(alkyl or substituted alkyl), —OC(O)-(alkyl or substituted alkyl), —C(S)-(alkyl or substituted alkyl), —CON(R')-(alkyl or substituted alkyl), —O—CON(R')-(alkyl or substituted alkyl), —CSN(R')-(alkyl or substituted alkyl), —N(R')CO-(alkyl or substituted alkyl), —N(R')C(O)O-(alkyl or substituted alkyl), —N(R')C(O)N(R')-(alkyl or substituted alkyl), where each R' is independently H, alkyl, or substituted alkyl;

$L_1$ is —C(O)-(alkyl or substituted alkyl), —C(O)O-(alkyl or substituted alkyl), —OC(O)-(alkyl or substituted alkyl), —CON(R')-(alkyl or substituted alkyl), alkyl, substituted alkyl, alkenyl, alkoxy, substituted alkoxy, alkylalkoxy, substituted alkylalkoxy, polyalkylene oxide, substituted polyalkylene oxide, aryl, substituted aryl, heteroaryl, substituted heteroaryl, alkaryl, substituted alkaryl, aralkyl, or substituted aralkyl;

X is —O-(alkylene or substituted alkylene)-, or —S(O)$_k$(alkylene or substituted alkylene)-, where k is 1, 2, or 3;

each n is an integral number selected from 1 to 20; and $L_2$ is selected from the group consisting of a direct bond, alkylene, substituted alkylene, alkenylene, substituted alkenylene, alkynylene, substituted alkynylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')$_2$—, —NR'-(alkylene or substituted alkylene)-, —C(O)N(R')—, —CON(R')-(alkylene or substituted alkylene)-, —O—CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —N(R')C(O)O-(alkylene or substituted alkylene)-, —S(O)$_k$N(R')—, —N(R')C (O)N(R')—, —N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl;

L is selected from the group consisting of alkylene, substituted alkylene, alkenylene, substituted alkenylene, alkynylene, substituted alkynylene, —O—, —O-(alkylene or substituted alkylene)-, -(alkylene or substituted alkylene)-O-(alkylene or substituted alkylene)-, —O-(alkylene or substituted alkylene)-O—, —S—, —S-(alkylene or substituted alkylene)-, -(alkylene or substituted alkylene)-S-(alkylene or substituted alkylene)-, —S(O)$_k$— where k is 1, 2, or 3, —S(O)$_k$(alkylene or substituted alkylene)-, -(alkylene or substituted alkylene)-S(O)$_k$-(alkylene or substituted alkylene)-, -(alkylene or substituted alkylene)-S—S-(alkylene or substituted alkylene)-, -(alkylene or substituted alkylene)-O-(alkylene or substituted alkylene)-S—S-(alkylene or substituted alkylene)-O-(alkylene or substituted alkylene)-, —C(O)—, —C(O)-(alkylene or substituted alkylene)-, -(alkylene or substituted alkylene)-C(O)-(alkylene or substituted alkylene)-, —C(S)—, —C(S)-(alkylene or substituted alkylene)-, -(alkylene or substituted alkylene)-C(S)-(alkylene or substituted alkylene)-, —N(R')$_2$—, —NR'-(alkylene or substituted alkylene)-, -(alkylene or substituted alkylene)-NR'-(alkylene or substituted alkylene)-, —C(O)N(R')—, —CON(R')-(alkylene or substituted alkylene)-, -(alkylene or substituted alkylene)-CON(R')-(alkylene or substituted alkylene)-, —O—CON(R')-(alkylene or substituted alkylene)-, -(alkylene or substituted alkylene)-O—CON(R')-(alkylene or substituted alkylene)-, —CSN(R')—, —CSN(R')-(alkylene or substituted alkylene)-, -(alkylene or substituted alkylene)-CSN(R')-(alkylene or substituted alkylene)-, —N(R')CO-(alkylene or substituted alkylene)-, -(alkylene or substituted alkylene)-N(R')CO-(alkylene or substituted alkylene)-, —N(R')C(O)O—, —N(R')C(O)O-(alkylene or substituted alkylene)-, -(alkylene or substituted alkylene)-N(R')C(O)O-(alkylene or substituted alkylene)-, —S(O)$_k$N(R')—, —N(R')C(O)N(R')—, —N(R')C(O)N(R')-(alkylene or substituted alkylene)-, -(alkylene or substituted alkylene)-N(R')C(O)N(R')-(alkylene or substituted alkylene)-, —N(R')C(S)N(R')—, —N(R')S(O)$_k$N(R')—, and —C(R')$_2$—N(R')—N(R')—; where each R' is independently H, alkyl, or substituted alkyl; and pharmaceutically acceptable salts; wherein the cancer is selected from breast cancer, colon cancer, lung cancer, male breast cancer, pancreatic cancer, Non-Hodgkin's lymphoma, melanoma skin cancer, and prostate cancer.

22. The method of claim 21 further comprising the step of administering to a patient in need thereof a therapeutically effective amount of motexafin gadolinium or a pharmaceutically acceptable texaphyrin derivative.

* * * * *